(12) United States Patent
Grout et al.

(10) Patent No.: US 11,078,945 B2
(45) Date of Patent: Aug. 3, 2021

(54) COUPLER TO ATTACH ROBOTIC ARM TO SURGICAL TABLE

(71) Applicant: Verb Surgical Inc., Mountain View, CA (US)

(72) Inventors: Wayne Grout, San Francisco, CA (US); David James Cagle, Belmont, CA (US); Richard William Timm, Palo Alto, CA (US); Brendan C. Reese, San Francisco, CA (US); Michael P. Schaller, Redwood City, CA (US); Robert J. Campbell, Nashua, NH (US)

(73) Assignee: VERB SURGICAL INC., Santa Clara, CA (US)

( * ) Notice: Subject to any disclaimer, the term of this patent is extended or adjusted under 35 U.S.C. 154(b) by 482 days.

(21) Appl. No.: 15/934,709

(22) Filed: Mar. 23, 2018

(65) Prior Publication Data

US 2018/0271604 A1 Sep. 27, 2018

Related U.S. Application Data

(60) Provisional application No. 62/476,816, filed on Mar. 26, 2017.

(51) Int. Cl.
*F16B 21/16* (2006.01)
*A61B 34/30* (2016.01)
(Continued)

(52) U.S. Cl.
CPC ............ *F16B 21/165* (2013.01); *A61B 34/30* (2016.02); *A61B 90/57* (2016.02); *B25J 9/0009* (2013.01);
(Continued)

(58) Field of Classification Search
CPC ..... A61B 34/30; A61B 90/57; B23B 31/1071; B25J 9/0009; B25J 9/0096; B25J 11/008;
(Continued)

(56) References Cited

U.S. PATENT DOCUMENTS 3,430,305 A 3/1969 Geffner
3,741,573 A * 6/1973 Treer .................. B23B 31/1071
279/81

(Continued)

FOREIGN PATENT DOCUMENTS

DE 10154876 C1 * 2/2003 ......... B23B 31/1071
DE 102005031784 A1 * 1/2007 ......... B23B 31/1071
(Continued)

OTHER PUBLICATIONS

International Preliminary Report on Patentability (Chapter 1 of PCT) dated Oct. 1, 2019, for PCT application No. US2018/024393.
(Continued)

*Primary Examiner* — Josh Skroupa
(74) *Attorney, Agent, or Firm* — Womble Bond Dickinson (US) LLP

(57) ABSTRACT

An apparatus can include a coupler for coupling a robotic arm to a surgical table having a table top on which a patient can be disposed. The coupler can include a first portion configured to couple to a surgical table and a second portion configured to couple to a robotic arm. The second portion may include a post that may translate into the first portion. The first portion may comprise a locking mechanism having one or more stages to constrain movement of the second portion relative to the first portion in six degrees of freedom. The coupler can thus provide secure coupling of the robotic arm to the surgical table.

20 Claims, 48 Drawing Sheets

(51) Int. Cl.
*A61B 90/57* (2016.01)
*B25J 9/00* (2006.01)

(52) U.S. Cl.
CPC ....... *B25J 9/0096* (2013.01); *A61B 2090/571* (2016.02)

(58) Field of Classification Search
CPC ...... B25J 11/0085; B25J 11/009; B25J 17/00; B25J 19/0041; F16B 21/16; F16B 21/165; Y10T 74/20335; Y10T 74/20341; Y10T 403/592; Y10T 403/602; Y10T 403/7045
USPC ........... 901/27, 28, 29; 403/322.2, 327, 364; 74/490.05, 490.06
See application file for complete search history.

(56) References Cited

U.S. PATENT DOCUMENTS

| | | | |
|---|---|---|---|
| 4,636,135 A * | 1/1987 | Bancon | B25J 15/0491 901/28 |
| 4,655,630 A | 4/1987 | Rhinehart | |
| 4,759,686 A | 7/1988 | Kirst | |
| 4,875,275 A | 10/1989 | Hutchinson et al. | |
| 5,243,264 A * | 9/1993 | Takada | B25J 15/04 318/567 |
| 6,451,027 B1 | 9/2002 | Cooper et al. | |
| 6,491,701 B2 | 12/2002 | Tierney et al. | |
| 6,788,018 B1 | 9/2004 | Blumenkranz | |
| 6,840,895 B2 | 1/2005 | Perry et al. | |
| 7,008,362 B2 | 3/2006 | Fitzgibbon | |
| 7,048,745 B2 | 5/2006 | Tierney et al. | |
| 7,331,967 B2 | 2/2008 | Lee et al. | |
| 7,379,790 B2 | 5/2008 | Toth et al. | |
| 7,524,320 B2 | 4/2009 | Tierney et al. | |
| 7,559,265 B2 | 7/2009 | Mizuno | |
| 7,654,285 B2 * | 2/2010 | Stark | B23Q 1/0072 137/614.03 |
| 7,748,690 B2 * | 7/2010 | Stark | B23B 31/1071 269/309 |
| 7,789,874 B2 | 9/2010 | Yu et al. | |
| 7,789,875 B2 | 9/2010 | Brock et al. | |
| 7,955,322 B2 | 6/2011 | Devengenzo et al. | |
| 7,983,793 B2 | 7/2011 | Toth et al. | |
| 8,062,288 B2 | 11/2011 | Cooper et al. | |
| 8,126,114 B2 | 2/2012 | Naylor et al. | |
| 8,142,447 B2 | 3/2012 | Cooper et al. | |
| 8,147,173 B2 * | 4/2012 | Goetz | B23B 31/1071 408/204 |
| 8,256,319 B2 | 9/2012 | Cooper et al. | |
| 8,469,947 B2 | 6/2013 | Devengenzo et al. | |
| 8,506,555 B2 | 8/2013 | Ruiz Morales | |
| 8,562,594 B2 | 10/2013 | Cooper et al. | |
| 8,634,957 B2 | 1/2014 | Toth et al. | |
| 8,747,288 B2 | 6/2014 | Strotzer et al. | |
| 8,761,337 B2 | 6/2014 | Naylor et al. | |
| 8,777,230 B2 * | 7/2014 | Ronald | B23B 31/1071 279/2.12 |
| 8,888,764 B2 | 11/2014 | Devengenzo et al. | |
| 8,968,333 B2 | 3/2015 | Yu et al. | |
| 8,992,113 B2 | 3/2015 | Campagna et al. | |
| 9,078,686 B2 | 7/2015 | Schena | |
| 9,254,572 B2 | 2/2016 | Strotzer | |
| 9,295,524 B2 | 3/2016 | Schena et al. | |
| 9,345,546 B2 | 5/2016 | Toth et al. | |
| 9,827,615 B2 * | 11/2017 | Chuang | B23B 31/1071 |
| 9,863,456 B2 * | 1/2018 | Canuto | B23B 31/1071 |
| 10,661,449 B2 * | 5/2020 | Zachary | B23B 31/1071 |
| 2001/0043841 A1 | 11/2001 | Wienhold | |
| 2006/0202480 A1 | 9/2006 | Cassel et al. | |
| 2007/0228670 A1 | 10/2007 | Norton et al. | |
| 2008/0223169 A1 | 9/2008 | Mizuno | |
| 2009/0044655 A1 | 2/2009 | Delouis et al. | |
| 2014/0171965 A1 | 6/2014 | Loh et al. | |
| 2015/0032126 A1 | 1/2015 | Nowlin et al. | |
| 2015/0045812 A1 | 2/2015 | Seo | |
| 2015/0265356 A1 | 9/2015 | Schena | |
| 2015/0321355 A1 | 11/2015 | Kishi | |
| 2016/0059424 A1 * | 3/2016 | Zachary | B23B 31/1071 483/1 |
| 2016/0250989 A1 | 9/2016 | Morrell et al. | |
| 2017/0021431 A1 | 1/2017 | Wong et al. | |

FOREIGN PATENT DOCUMENTS

| | | |
|---|---|---|
| JP | 60-155387 A | 8/1985 |
| JP | 62-100889 U | 6/1987 |
| JP | 07-328014 A | 12/1995 |
| JP | 3053042 U | 10/1998 |
| JP | 2001-129038 A | 5/2001 |
| JP | 2008-221390 A | 9/2008 |
| JP | 2010-264130 A | 11/2010 |
| JP | 2015-198933 A | 11/2015 |
| WO | 2009/027734 A2 | 3/2009 |

OTHER PUBLICATIONS

Examination Report of the Australian Patent Office dated Aug. 5, 2020 for related Australian Patent Application No. 2018243738.
International Search Report dated Jul. 16, 2018, for PCT application No. US2018/024393.
Written Opinion of the International Searching Authority dated Jul. 16, 2018, for PCT application No. US2018/024393.
Examination Report No. 2 of the Australian Patent Office dated Nov. 17, 2020 for related Australian Patent Application No. 2018243738.
Examination Search Report of the Canadian Patent Office dated Nov. 13, 2020 for related Canadian Patent Application No. 3054431.
Notice of Reasons for Rejection of the Japanese Patent Office dated Oct. 5, 2020 for related Japanese Patent Application No. 2019-551299.
Supplementary European Search Report and Search Opinion of the European Patent Office dated Nov. 13, 2020 for related European Patent Application No. 18774510.4.
Notice of Office Action of the Korean Patent Office dated Jan. 29, 2021 for related Korean Patent Application No. 10-2019-7027941.
Examination Report for Australian Application No. 2018243738 dated Mar. 17, 2021, 5 pages.

* cited by examiner

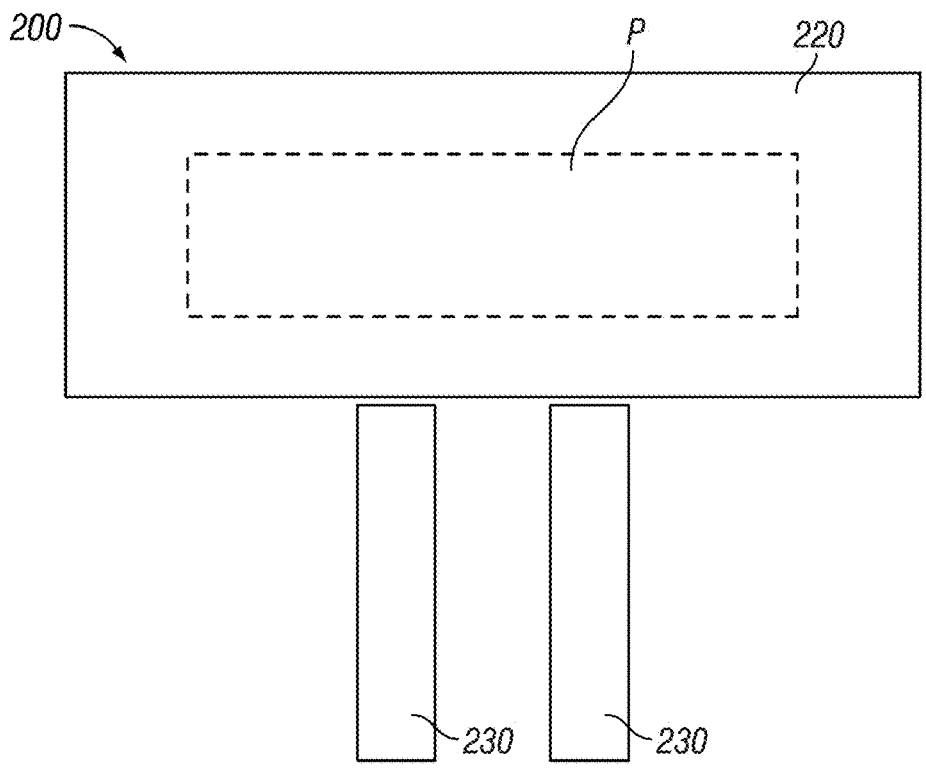
FIG. 2A
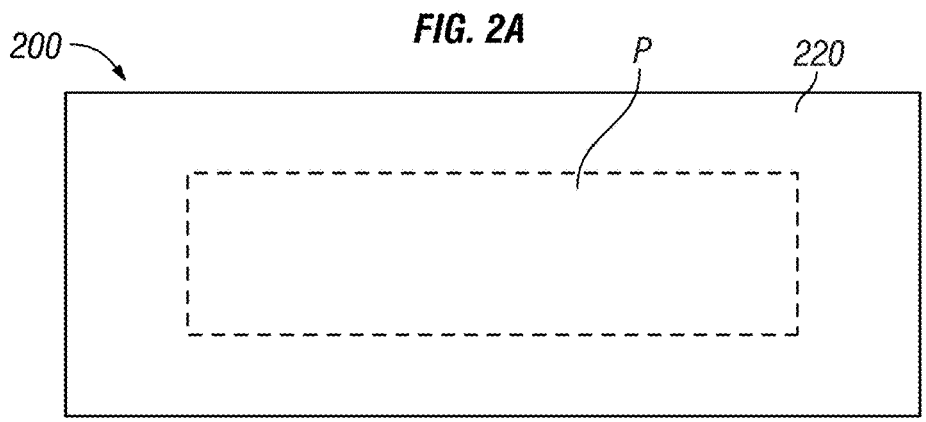
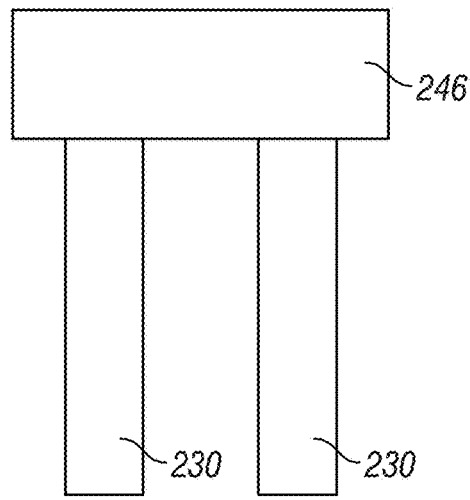
FIG. 2B

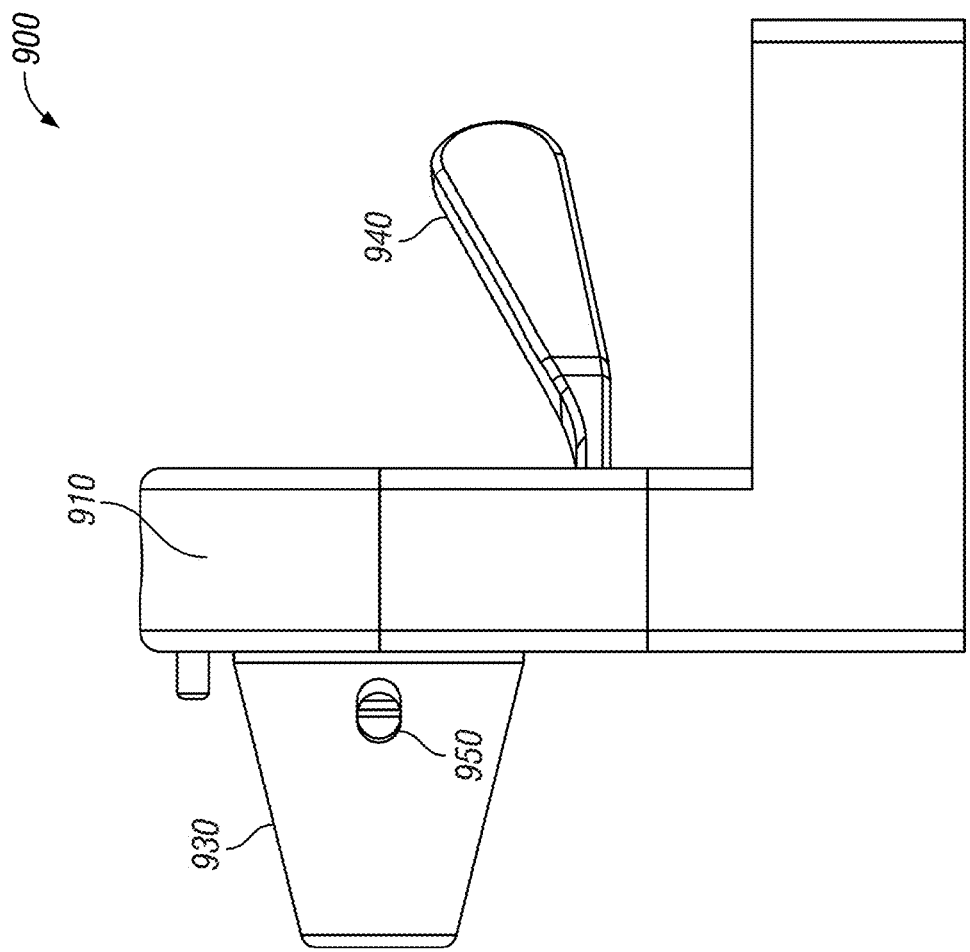
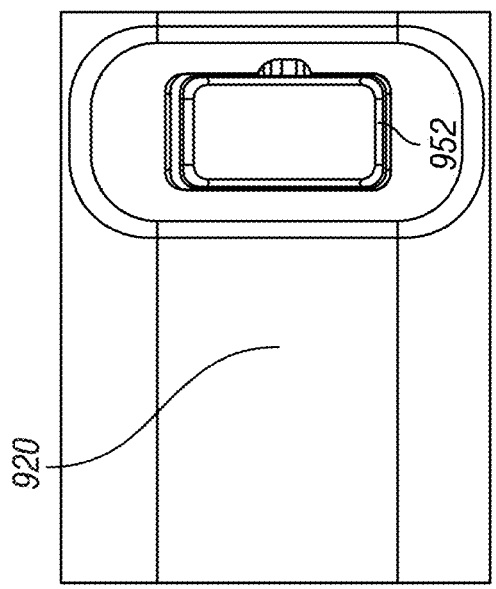
FIG. 9C

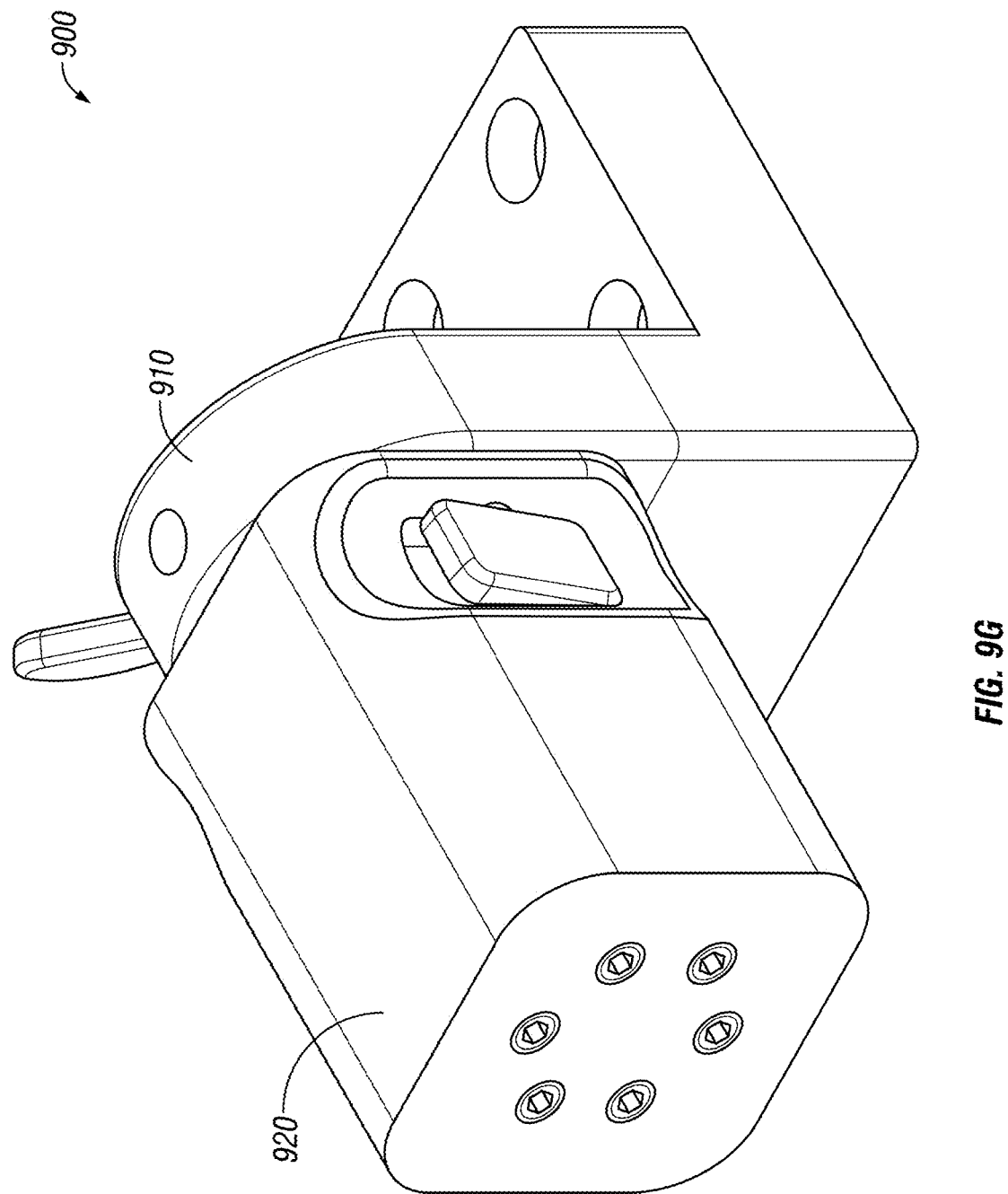

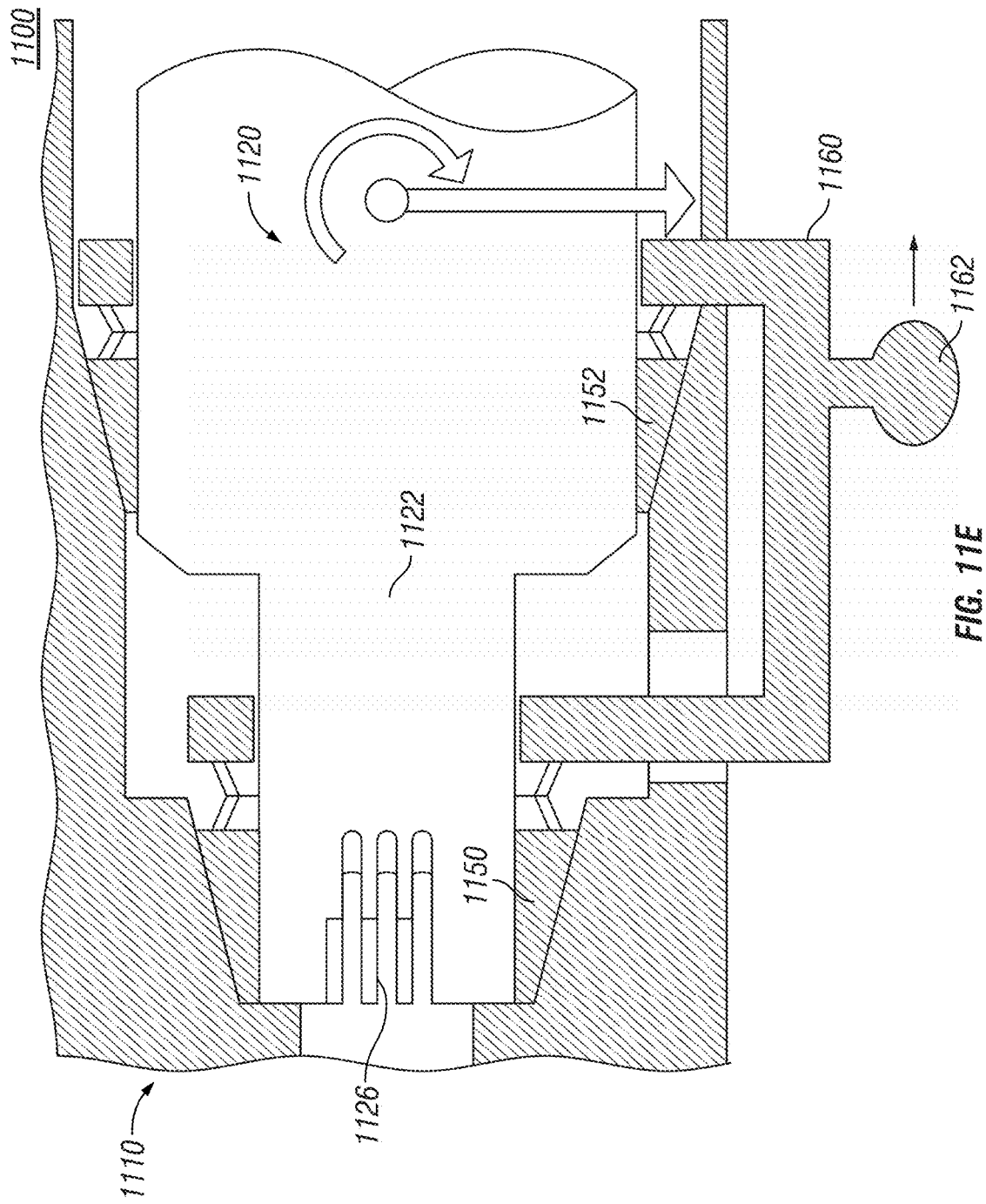

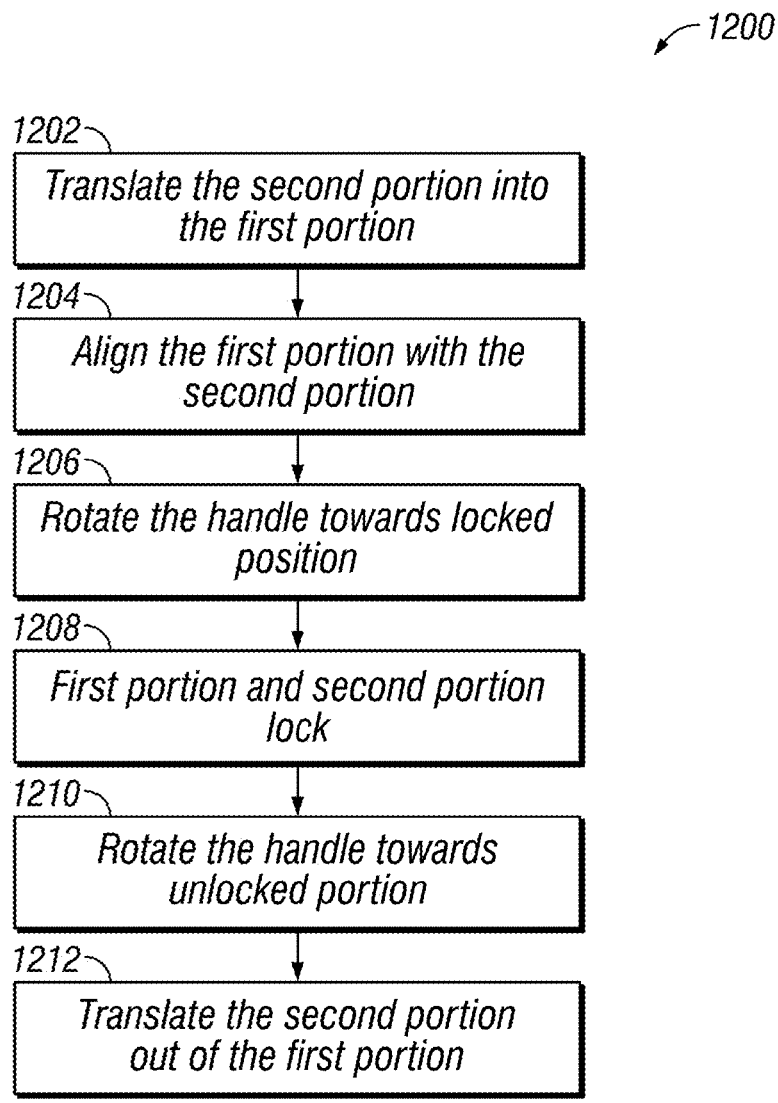

COUPLER TO ATTACH ROBOTIC ARM TO SURGICAL TABLE

CROSS-REFERENCE TO RELATED APPLICATION

The application is a non-provisional application of U.S. Provisional Patent Application No. 62/476,816, filed Mar. 26, 2017 and incorporated herein by reference.

FIELD

An apparatus and methods for coupling a robotic arm to a surgical table. Other embodiments are also described herein.

BACKGROUND

Robotic arms may be coupled to a surgical table to provide power, data, and mechanical support to the arms. The functionality of the surgical table coupled to one or more robotic arms can be limited by the volume of space occupied by the robotic arms and which are generally fixed to the table and difficult to remove. Some conventional robotic arms require a technician having specialized training to connect and disconnect the robotic arms to the table such that changing and/or servicing a robotic arm is a time-consuming and expensive task. However, even trained technicians may drop and damage a robotic arm during a coupling or decoupling operation because they do not force a user to support the arm during coupling or decoupling. For these and other reasons, robotic arms coupled to a surgical table are considered generally fixed to each other. For example, robotic arms coupled to a surgical table should adhere to IPX4 requirements related to ingress protection against foreign objects (e.g., liquids). Adhering to this regulatory standard further complicates the design and cost of a robotic surgical arm.

Removal and reattachment of a robotic arm may introduce misalignment between the robotic arm and surgical table. In other words, conventional coupling mechanisms between a robotic arm and a surgical table do not register and/or provide confirmation that the robotic arm is positioned at a precise set of coordinates relative to the surgical table. Furthermore, some conventional robotic arm coupling mechanisms use removable components (e.g., bolts) that may be misplaced and result in misalignment and/or failure of an arm to table coupling. Additional apparatus and methods for coupling a robotic arm to a surgical table are desirable.

SUMMARY

The present invention is directed to an apparatus and methods for coupling robotic arms to a surgical table having a table top on which a patient can be disposed are described herein. In some embodiments, the apparatus and methods may allow a robotic arm to be securely coupled to and aligned with a surgical table.

In some embodiments, the robotic arm may be quickly released from the surgical table (e.g., quick release, bail-out) such as for an emergency situation where access to the surgical table top is necessary. The robotic arm may include a first portion of a coupler and the surgical table may include a second portion of the coupler where the first portion complements the second portion. After inserting the first portion having a post into a ball bearing holder of the second portion, a user may rotate a handle to secure the coupling between the first and second portion. In some embodiments, the coupler can include kinematic mounts configured to precisely and repeatably align the first and second portions.

In some embodiments, a motorized locking mechanism of a coupler may generate high forces to ensure the coupling is constrained and maintained in six degrees of freedom even in the presence of external loads. The robotic arm may include a first portion of a coupler and the surgical table may include a second portion of the coupler where the first portion complements the second portion. After inserting the first portion having a lead screw into a corresponding threaded portion of a collet, a motor may rotate the collet to bring the first portion into the second portion and secure the coupling between the first and second portion.

In some embodiments, a coupler may include a first portion having a cone with a conical taper and a second portion having corresponding conical hole that may constrain translational and rotational movement of the first and second portions along multiple axes. The coupler may include a multi-stage locking mechanism actuated by a handle and/or switch to couple and decouple the first and second portions from each other.

In some embodiments, a coupler may include a multi-stage locking mechanism including a radial clamp configured to secure a coupling between a first portion and a second portion using rotational and/or translational motion.

In some embodiments, a coupler may include a catch mechanism configured as a locking mechanism. The mechanism may include a linearly driven dual sided rack with a set of rotating cam claws. The coupling mechanism can be manually back driven. In some embodiments, the apparatus and methods can allow a robotic arm to be quickly released from a surgical table (e.g., quick release, bail-out) using a pin release mechanism such as for an emergency situation where access to the surgical table top is necessary.

The above summary does not include an exhaustive list of all aspects of the present invention. It is contemplated that the invention includes all apparatuses that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments disclosed herein are illustrated by way of example and not by way of limitation in the figures of the accompanying drawings in which like references indicate similar elements. It should be noted that references to "an" or "one" embodiment in this disclosure are not necessarily to the same embodiment, and they mean at least one.

FIG. 2A is a schematic top view of a surgical table with robotic arms coupled thereto, according to an embodiment.

FIG. 2B is a schematic top view of a surgical table with robotic arms and an arm adapter coupled thereto, according to an embodiment.

FIGS. 4A and 4E are side views, FIGS. 4B-4D are perspective views, FIGS. 4F and 4H-4L are cross-sectional side views, and FIG. 4G is a cross-sectional perspective view.

FIGS. 6A-6B are cross-sectional perspective views and FIG. 6C is a perspective view.

FIG. 7A is a cross-sectional perspective view and FIGS. 7B-7D are cross-sectional side views.

FIGS. 9A-9M illustrate a coupler, according to an embodiment. FIGS. 9A-9B, 9D, 9G, and 9L are perspective views, FIGS. 9C and 9I-9J are side views, FIGS. 9E-9F and 9K are top views, and FIGS. 9H and 9M are cross-sectional top views.

FIGS. 11A-11F and FIG. 11H are cross-sectional side views, and FIGS. 11G and 11I are perspective views.

FIG. 12 is a flowchart of a method of attaching a robotic arm to a surgical table, according to an embodiment.

DETAILED DESCRIPTION

In this section we shall explain several preferred embodiments with reference to the appended drawings. Whenever the shapes, relative positions and other aspects of the parts described in the embodiments are not clearly defined, the scope of the embodiments is not limited only to the parts shown, which are meant merely for the purpose of illustration. Also, while numerous details are set forth, it is understood that some embodiments may be practiced without these details. In other instances, well-known structures and techniques have not been shown in detail so as not to obscure the understanding of this description.

Apparatus and methods for providing a coupler to attach robotic arms to a surgical table having a table top on which a patient can be disposed are described herein. These apparatus and methods can be used to securely attach and align and/or quickly detach one or more robotic arms to a surgical table in a consistent manner, thereby increasing flexibility in configuring and customizing a surgical table with one or more robotic arms. For example, the coupling mechanisms described herein can be oriented and constrained in six degrees of freedom with high mechanical stiffness in the presence of external loads (e.g., robotic arm static and inertial loads during a surgical procedure).

Surgical Table and Robotic Arms

Figure 1A:
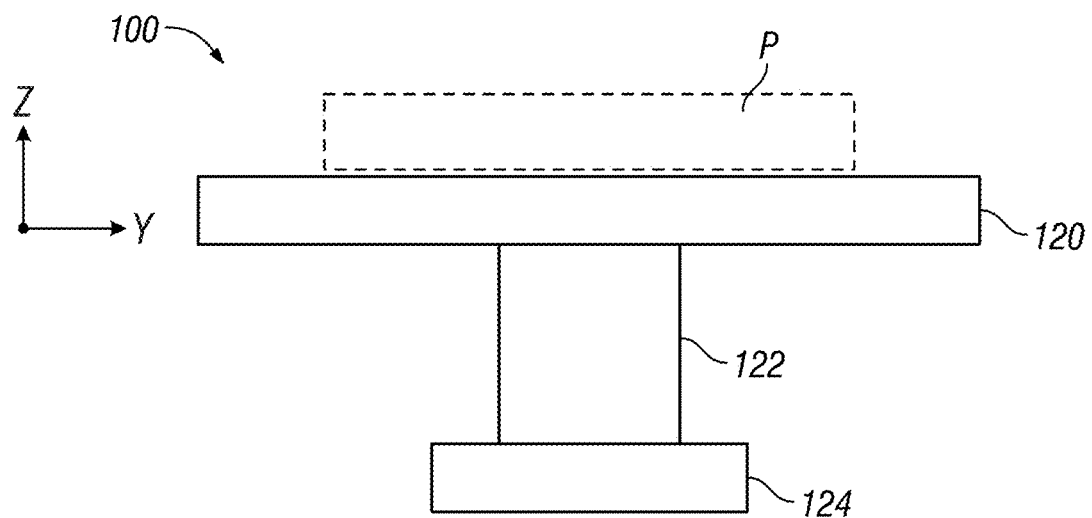
FIGS. 1A and 1B are a schematic side view and a schematic top view, respectively, of a surgical table, according to an embodiment.
Figure 1B:
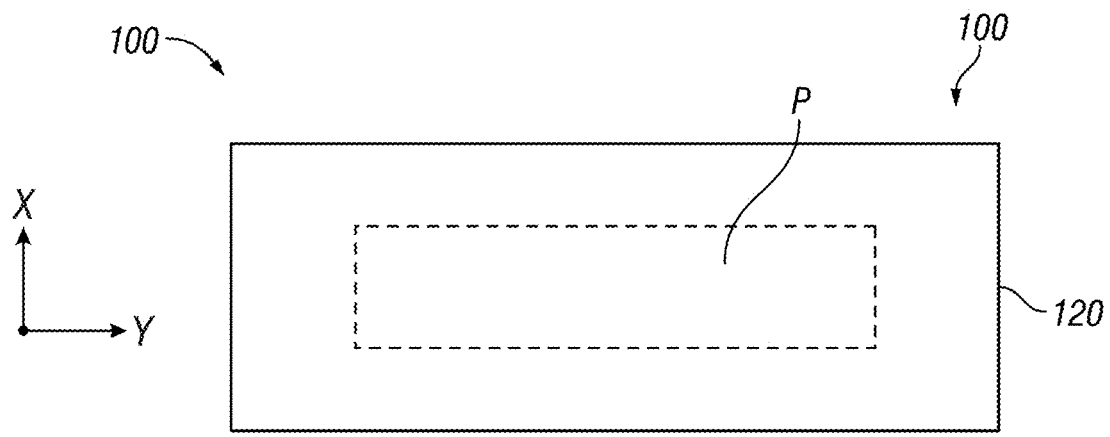

As shown schematically in FIGS. 1A-1B, a surgical table 100 includes a table top 120, a table support 122 and a table base 124. The table top 120 has an upper surface on which a patient P can be disposed during a surgical procedure, as shown schematically in FIG. 1A. The table top 120 is disposed on the support 122, which can be, for example, a pedestal, at a suitable height above the floor. The support 122 (also referred to herein as a pedestal) may provide for movement of the table top 120 in a desired number of degrees of freedom, such as translation in the Z-axis (height above the floor), Y-axis (along the longitudinal axis of the table), and/or X-axis (along the lateral axis of the table), and/or rotation about the Z, Y, and/or X-axes. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, or through any other suitable means. The support 122 for the table top may be mounted to the base 124, which can be fixed to the floor of the operating room, or can be movable relative to the floor, e.g., by use of wheels on the base 124. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the support 120. This also can allow robotic arms (e.g., arms 130 discussed below) coupled to the table 100 to reach a desired treatment target on a patient P disposed on the table top 120.

In a robotically-assisted surgical procedure, one or more robotic arms 130 (shown schematically in FIGS. 1C and 1D) can be disposed in a desired operative position relative to a patient disposed on the table top 120 of the surgical table 100 (also referred to herein as "table"). The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function.

Figure 1C:
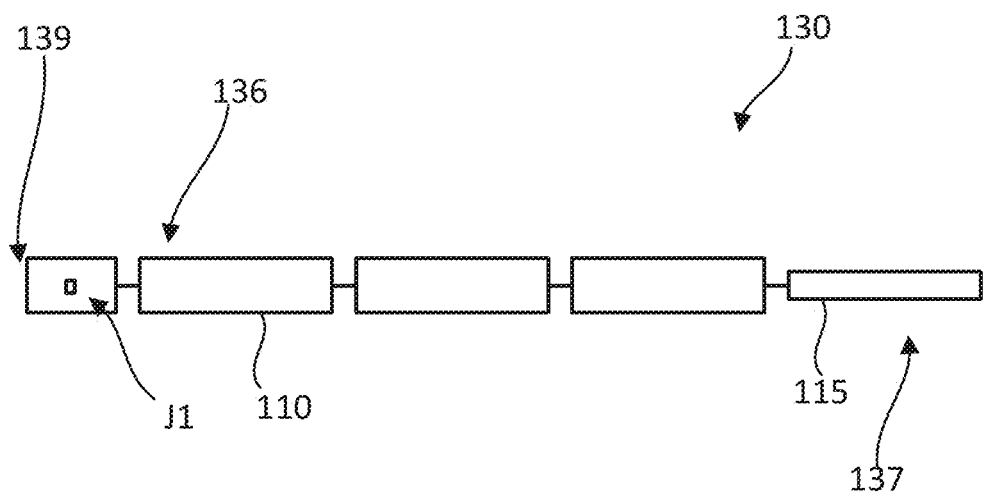
FIG. 1C is a schematic side view of a robotic arm, according to an embodiment, shown in an extended or use configuration.
Figure 1D:
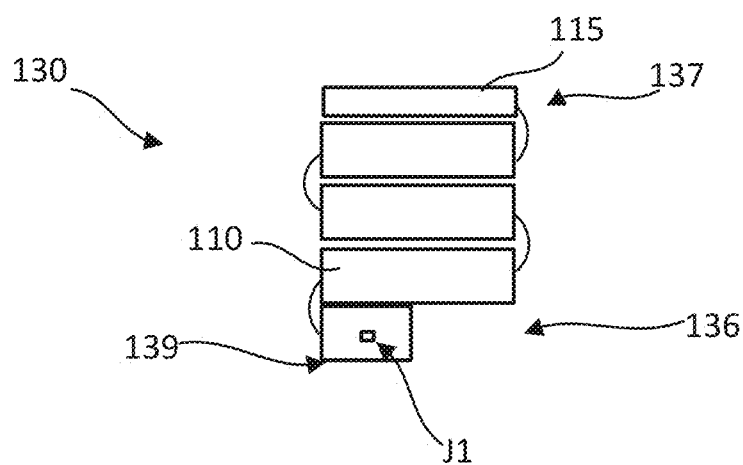
FIG. 1D is a schematic side view of the robotic arm of FIG. 1C, shown in a collapsed or folded configuration.

As shown schematically in FIGS. 1C and 1D, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the table 100. The robotic arm 130 can include two or more link members or segments 110 coupled together at joints that can provide for translation along and/or rotation about one or more of the X, Y and/or Z-axes (shown, for example, in FIGS. 1A and 1B). The coupling portion of the robotic arm 130 can include a coupling mechanism 139. The coupling mechanism 139 can be disposed at the mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling mechanism 139 and/or the coupling portion or can be disposed on a link or segment 110 of the robotic arm 130 that is coupled to the coupling portion. The target joint J1 can provide a pivot joint to allow a distal segment of the robotic arm 130 to pivot relative to the table 100. The robotic arm 130 can be moved between various extended configurations for use during a surgical procedure, as shown in FIG. 1C, and various folded or collapsed configurations for storage when not in use, as shown in FIG. 1D.

Various embodiments illustrating and describing apparatus and methods for coupling a robotic arm to a surgical table are disclosed herein. As described above and in accordance with various embodiments disclosed in more detail below, a robotic arm for use in performing a surgical procedure may be releasably coupled to a surgical table. In some embodiments, robotic arms can be coupled at a fixed location on the table or can be coupled such that the robotic arms can be movable to multiple locations relative to the table top. For example, as shown schematically in FIG. 2A, robotic arms 230 can be coupled to a table top 220 of a surgical table 200. The surgical table 200 can be the same or similar in structure and function to the surgical table 100 described above. For example, the table top 220 has an upper surface on which a patient P can be disposed during a surgical procedure. In some embodiments, the robotic arms 230 can be permanently or releasably coupled, in a fixed or movable location, to an arm adapter that is coupled to or separate from the surgical table. For example, as shown schematically in FIG. 2B, an arm adapter 246 can be coupled to or separate from but engageable with or couplable to the table top 220. The robotic arms 230 can be coupled to the arm adapter 246.

Arm Base Connection

Figure 3:
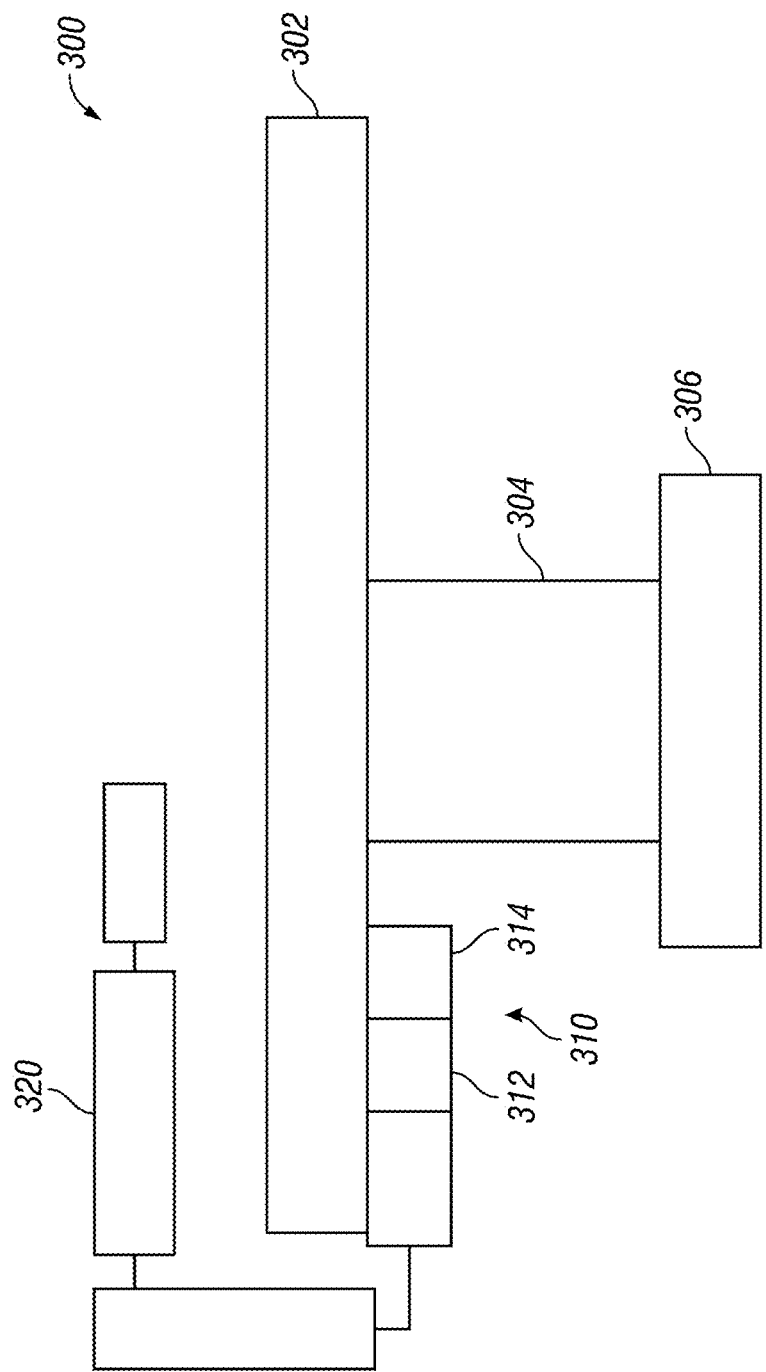
FIG. 3 is a schematic illustration of a coupler for attachment of a robotic arm to a surgical table, according to an embodiment.

As shown schematically in FIG. 3, a coupler 310 may be provided to couple a robotic arm 320 to a surgical table 300. The coupler 310 as described herein is usable with any of the surgical tables and robotic arms (e.g., surgical table 100, 200, robotic arms 130, 230), and methods described herein. The coupler 310 can include a first portion 312 (e.g., arm adapter) such as a terminal base portion A for a robotic arm. The coupler 310 can include a second portion 314 such as a base portion B for mounting to the surgical table 300. The robotic arm 320 can be coupled to the first portion 312 and the table top 302 can be coupled to the second portion 314 prior to coupling of the first portion 312 to the second portion 314. The coupling of the robotic arm 320 to the surgical table 300 can allow the robotic arm coupled to the table 300 to reach a desired treatment target on a patient disposed on the table top 302. The first portion 312 and the second portion 314 may further include electrical power and data connectors. It should be appreciated that the first portion 312 and second portion 314 may be reversed such that the first portion 312 couples to the table 300 and the second portion 314 couples to the robotic arm 320.

A surgical table 300 includes a table top 302, a table support 304 and a table base 306. The table top 302 has an upper surface on which a patient can be disposed during a surgical procedure, as shown schematically in FIG. 1A. The table top 302 is disposed on the support 304, which can be, for example, a pedestal, at a suitable height above the floor. The support 302 may provide for movement of the table top 302 in a desired number of degrees of freedom, such as translation in the Z-axis (height above the floor), Y axis (along the longitudinal axis of the table), and/or X-axis (along the lateral axis of the table), and/or rotation about the Z, Y, and/or X axes. The support 304 for the table top 302 may be mounted to the base 306, which can be fixed to the floor of the operating room, or can be movable relative to the floor, e.g., by use of wheels on the base 306. In a robotically-assisted surgical procedure, one or more robotic arms 320 (shown schematically in FIGS. 1C and 1D) can be disposed in a desired operative position relative to a patient disposed on the table top 302 of the surgical table 300.

Kinematic Mount Arm Base Connection

Figure 4A:
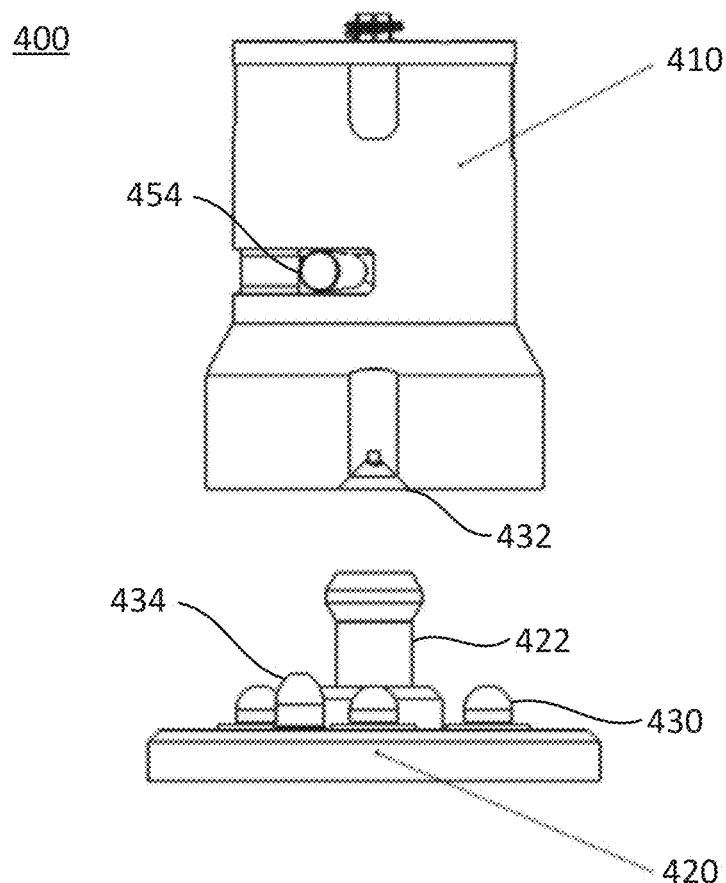
FIGS. 4A-4L illustrate a coupler, according to an embodiment.
Figure 4B:
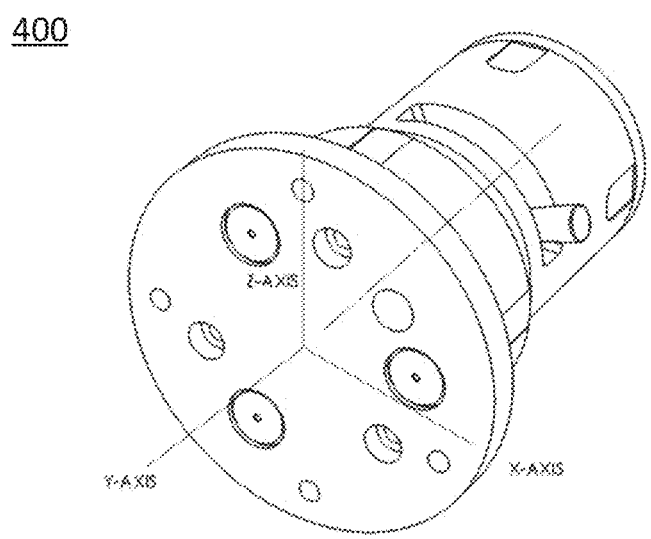

FIG. 4A is a side view of an embodiment of a coupler 400 including a first portion 410 and a second portion 420. Coupling of the first portion 410 and second portion 420 forms a secure mating connection where six degrees of freedom are constrained. For example, the secure mating connection y-axis constrains a translation in the Z-axis, a Y axis, and/or X-axis, and/or rotation about the Z, Y, and/or X-axes, of the first portion 410 with respect to the second portion 420. The first portion 410 includes a handle 454 configured to lock and secure the coupling between the first portion 410 and second portion 420, and a set of V-grooves 432 configured to contact a corresponding kinematic mount 430, as described herein. The second portion 420 includes a post 422 (e.g., locking post) that may be translated along a Y axis to mate with the first portion 410. Coupling the post 422 to the first portion 410 may constrain translation along the Y axis. FIG. 4B illustrates the X-axis, Y axis, and Z-axis relative to the coupler 400.

The second portion 420 may further include a set of kinematic mounts 430 that may include at least three kinematic mounts that protrude from a surface of the second portion 420 and are configured to slide into and mate with a corresponding V-groove 432. The kinematic mounts 430 and V-grooves 432 are configured to locate, constrain, and support the coupling between the first portion 410 and second portion 420. The kinematic mounts 430 may include a spherical or semi-spherical shape. The kinematic mounts 430 may be equally spaced apart around the post 422 of the second portion 420. The V-grooves 432 may form a V-shaped cut-out in the first portion 410 and may further include a groove at a vertex of the "V". The sphere-in-groove mating connection between the kinematic mounts 430 and V-grooves 432 may constrain translation in the X-axis and Z-axis and constrain rotation about the X-axis, Y axis, and Z-axis.

Figure 4C:
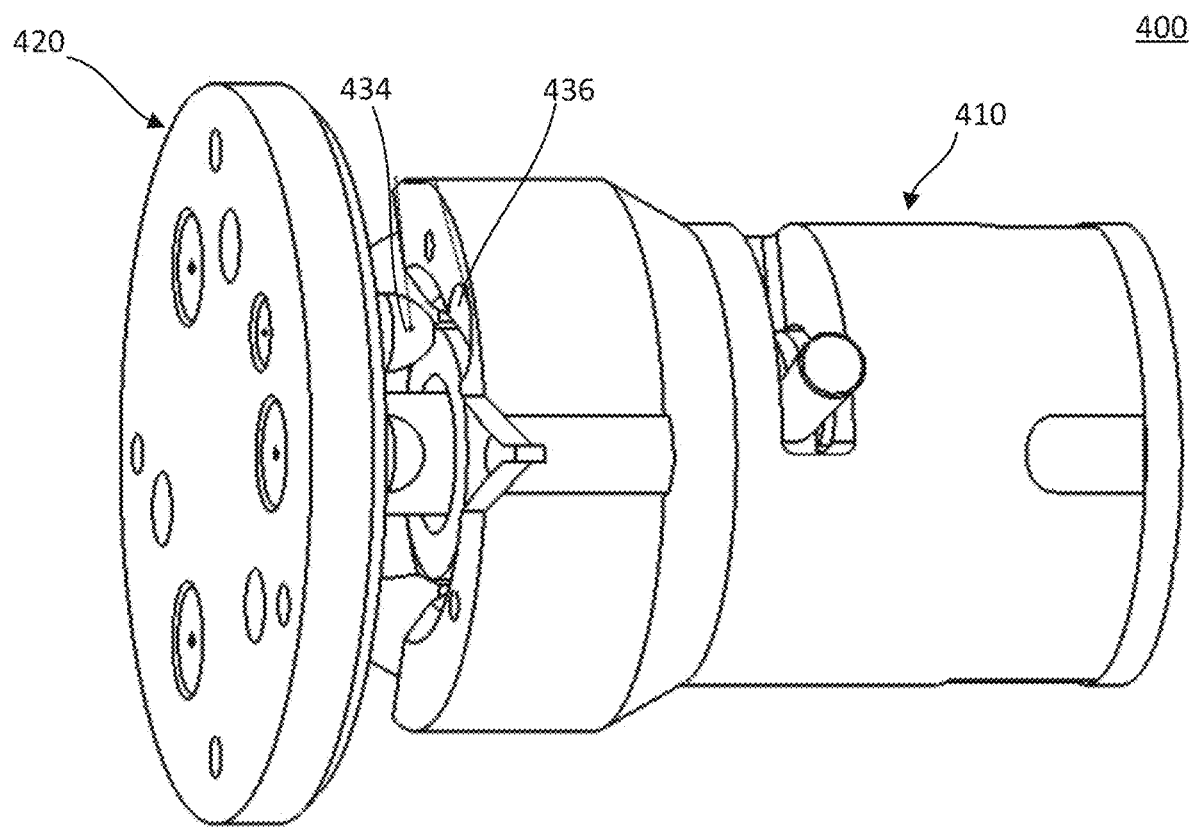

Some embodiments of the second portion 420 may include one or more alignment protrusions 434 configured to contact and slide into and mate with a corresponding hole (not shown) in the first portion 410. The alignment protrusion 434 is asymmetrical in that alignment of the protrusion 434 with the first portion 410 is configured to prevent a user from inserting the first portion 410 incorrectly into the second portion 420. This process may be referred to herein as registration. The shape of the alignment protrusion 434 shown is having a semispherical end, but is not particularly limited. The post 422 of the second portion 420 will not be translated along the Y axis sufficiently into the first portion 410 to engage coupling and locking of the first portion 410 to the second portion 420 when the alignment protrusion 434 is misaligned. For example, FIG. 4C illustrates the second portion 420 partially inserted into the first portion 410. The alignment protrusion 434 and alignment hole 436 are oriented so as to permit the post 422 of the second portion 420 to be fully translated into the first portion 410. Otherwise, the alignment protrusion 434 contacts the housing of the first portion 410 to create a gap between the first portion 410 and the second portion 420 that prevents their coupling.

Figure 4D:
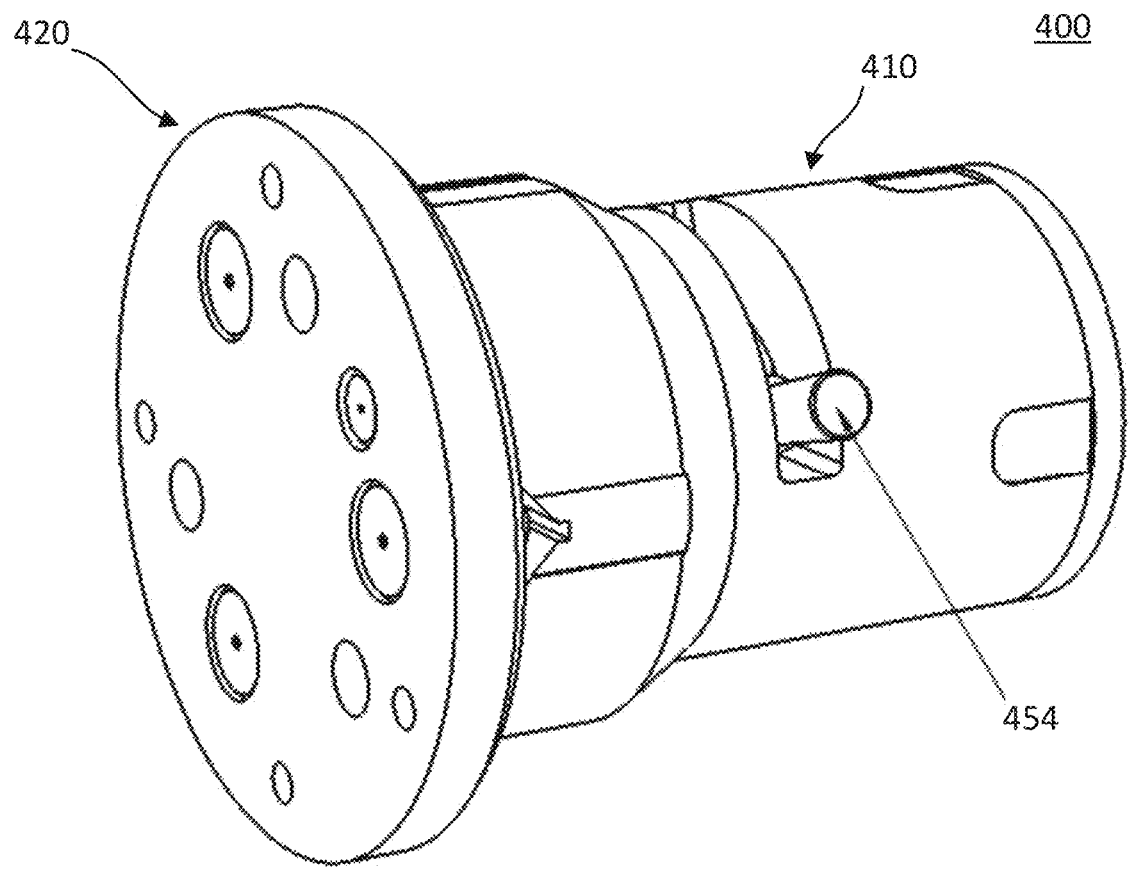
Figure 4E:
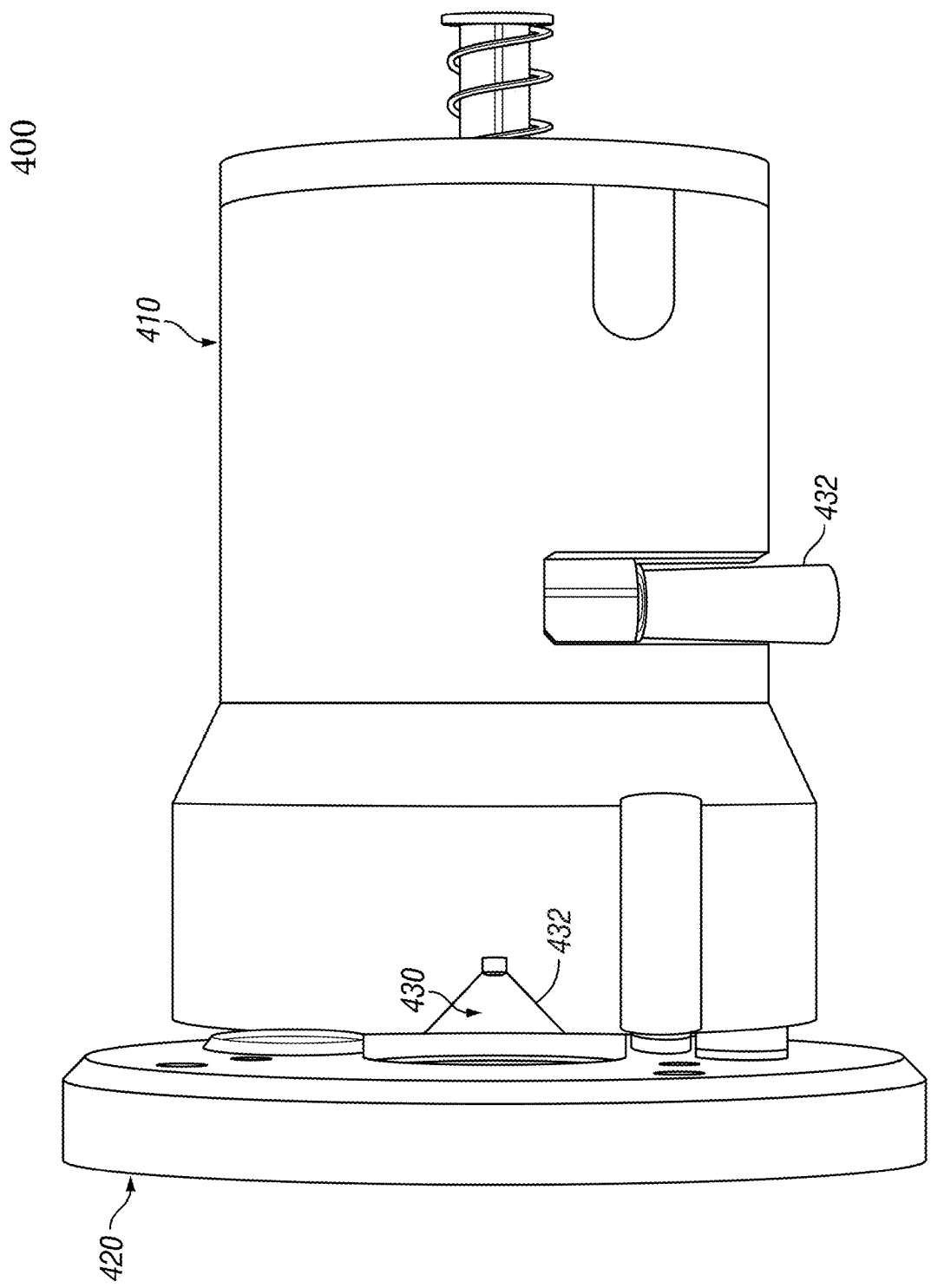

FIG. 4D illustrates a perspective view of the first portion 410 aligned and having an initial engagement with the second portion 420. The handle 454 (e.g., lock handle) is in a first position corresponding to a first position (e.g., unlocked position) of the coupler 400. A user may rotate the handle 454 into a second position (e.g., locked position) to transition the coupler 400 from a first configuration (e.g., unlocked state or position) to a second configuration (e.g., locked state or position). FIG. 4E illustrates an alignment state of the first configuration where the post 422 is translated into first portion 410, and the first portion 410 and second portion 420 are aligned, but without engaging a locking mechanism between the first portion 410 and the second portion 420. In particular, each of the kinematic mounts 430 are aligned with and engaged to contact and mate with a corresponding V-groove 432.

Figure 4F:
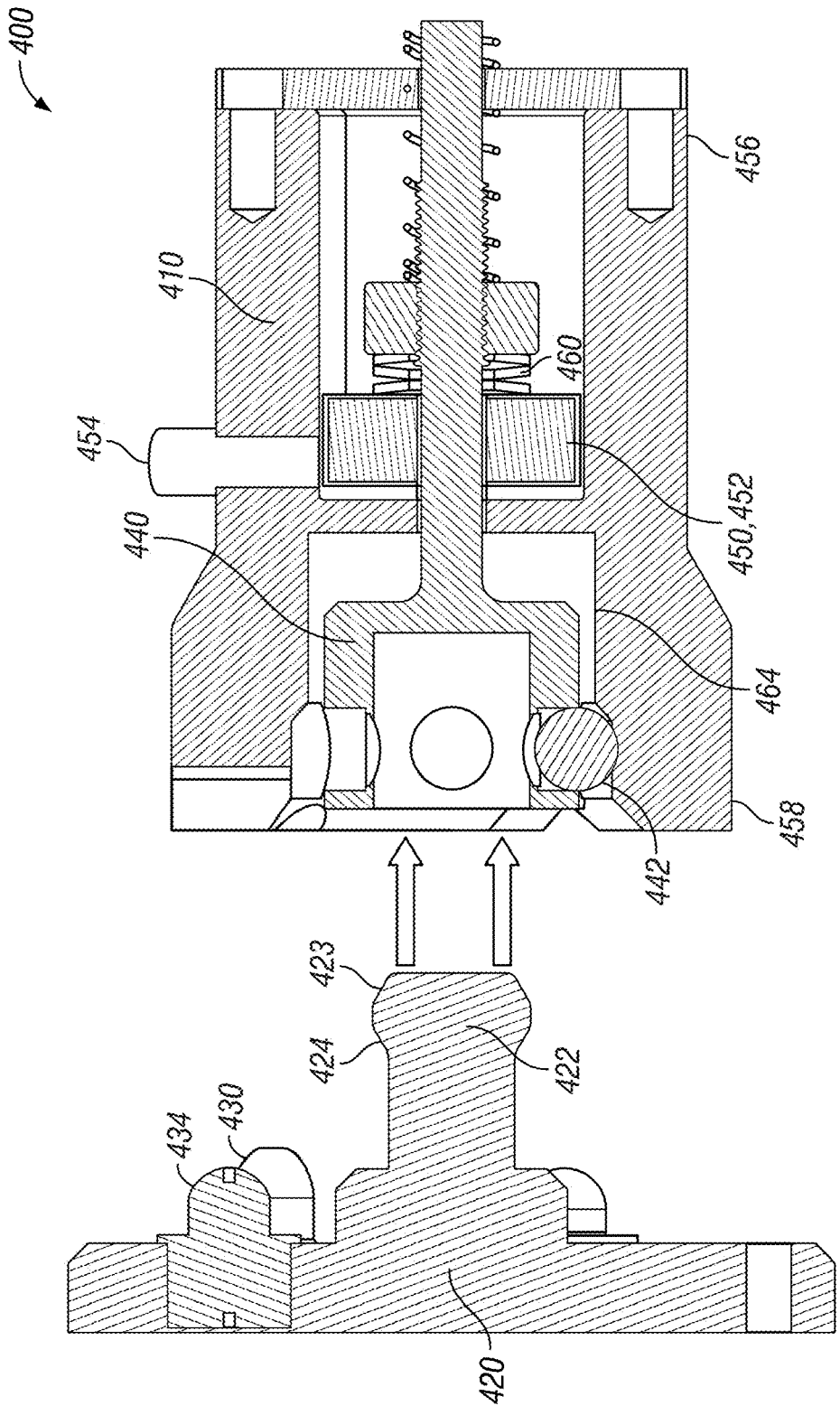

FIG. 4F is a cross-sectional side view of the initial translation of the second portion 420 into the first portion 410. From this view, it can be seen that first portion 410 includes a first end 456 (the end that attaches to the robotic arm) and a second end 458 (the end that attaches to second portion 420), and an interior cavity 464 formed within first portion 410, between the first and second ends. An opening to the interior cavity is formed through the second end 458. The first portion 410 further includes a ball bearing holder 440 (e.g., draw bar) coupled to a set of ball bearings 442, which are positioned within interior cavity 464. The set of ball bearings 442 may include four or more ball bearings equally spaced apart along a circumference of the ball bearing holder 440. The handle 454 may be coupled to a pair of cams including a first face cam 450 and a second face cam 452. A set of Belleville washers 460 may be coupled a shaft of the ball bearing holder 440. The post 422 of the second portion 420 may include a first surface 423 (e.g., lead in taper) configured to permit misalignment during translation and sliding of the post 422 into the ball bearing holder 440. The post may further include a second surface 424 (e.g., angled face) configured to press against the ball bearings 442 when the mating connection is locked. The first surface 423 and second surface 424 experience Hertzian stresses based on the curvature of the surfaces. The curvature and material properties, along with the ball bearing 442 diameter and material may be configured to generate contact conditions that do not deteriorate the surfaces.

The ball bearing holder 440 is configured to hold the ball bearings 442 and surround the post 422. The ball bearing holder 440 is configured to translate along the Y axis relative to a housing of the first portion 410 when the face cams are rotated by the handle 454. The translation of the ball bearing holder 440 into the first portion 410 presses the ball bearings 442 into surfaces in the first portion 410, surfaces in the ball bearing holder 440, and surfaces in the post 422. As illustrated herein, the ball bearing holder 440 may include a lip on each ball bearing pocket configured to retain the ball bearing 442 within the holder 440 when the ball bearings 442 are not in contact with the post 422. These surfaces experience Hertzian stresses based on the curvature of the surfaces. The curvature and material properties, along with the ball bearing 442 diameter and material may be configured to generate contact conditions that do not deteriorate the surfaces. The ball bearings 442 move within a predetermined range within the ball bearing holder 440 and serve as a locking mechanism to apply forces to both the first portion 410 and second portion 420 to securely lock them together and form a coupling between the first portion 410 and the second portion 420.

Figure 4G:
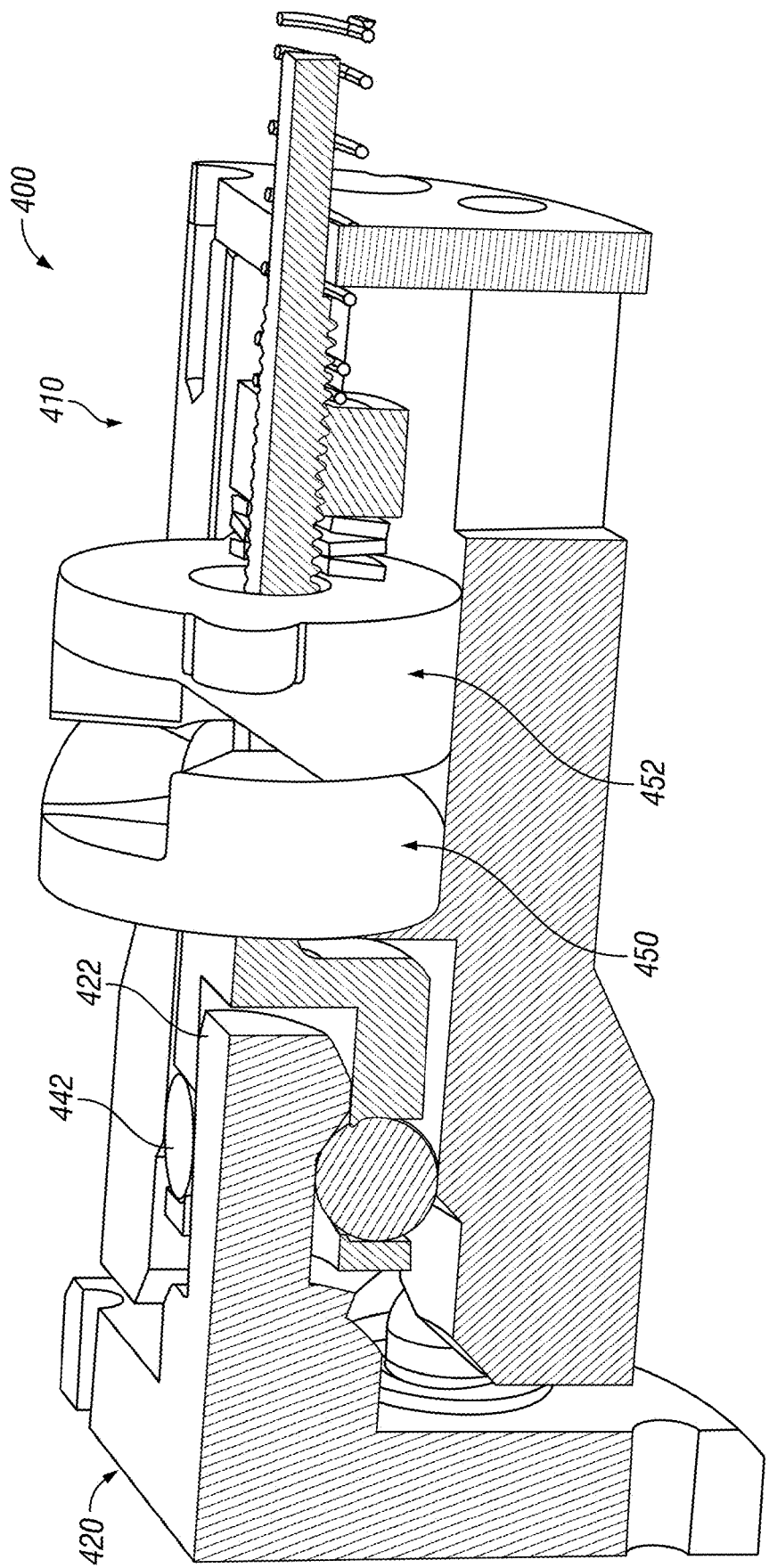

FIG. 4G is a cross-sectional perspective view of the coupler 400 in a locked state (or locked position) illustrating the first face cam 450 and second face cam 452 in a maximally separated position where the ball bearing holder 440 is maximally translated into the first portion 410 and the ball bearings 442 have engaged the post 442 and housing 410 to securely lock and couple the first portion 410 to the second portion 420 (e.g., the locked position). The first face cam 450 and second face cam 452 are coupled to the ball bearing holder 440 such that translation of the face cams along the Y-axis also translates the ball bearing holder 440 along the Y-axis. Each of the face cams may include a profile that converts rotational motion (e.g., from motion of handle 454) about the Y-axis into translational motion about the Y-axis. The handle 454 may be threaded directly into one of the face cams, thereby allowing for a torque advantage when the face cams are rotated into the locked position. The face cams may include a variable cam profile having a first and second profile. A first profile may be configured to permit relatively greater translation and a relatively lower axial force advantage. A second profile may be configured to permit a relatively lower translation and a relatively greater axial force advantage. For example, the first profile may be steep and a second profile may be shallow. In some embodiments, the varying cam profile may configured to permit a large translation (e.g., 0.25") followed by a very small (e.g., 0.04") translation. In some embodiments, the face cams may include a compound profile that decreases the pitch as the ball bearing holder reaches full engagement (e.g., as the ball bearing holder translates towards a lock position. In some embodiments, the face cams may include a thrust bearing to reduce friction on the outer surfaces of the face cam. In some embodiments, the face cams may include lobes configured to distribute pressure evenly. In some embodiments, different portions of the face cams may be made of different materials in order to variably change friction and/or strength of the face cams.

Figure 4H:
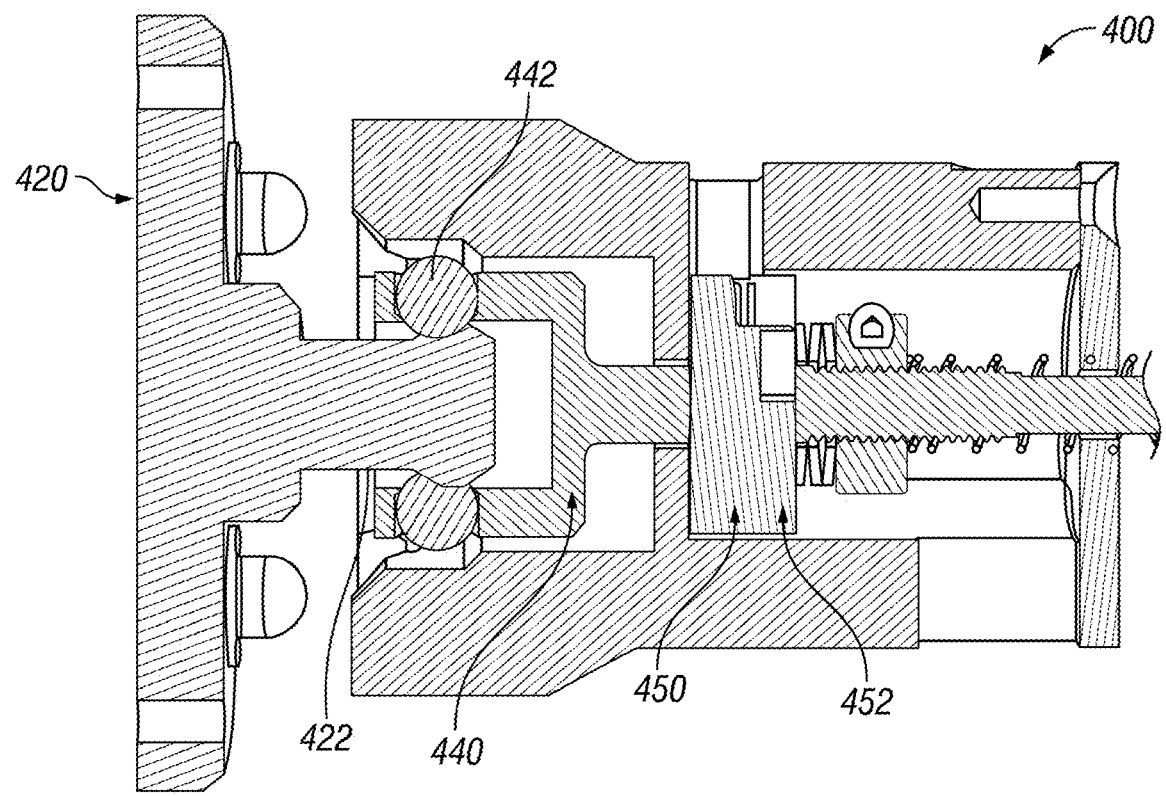
Figure 4I:
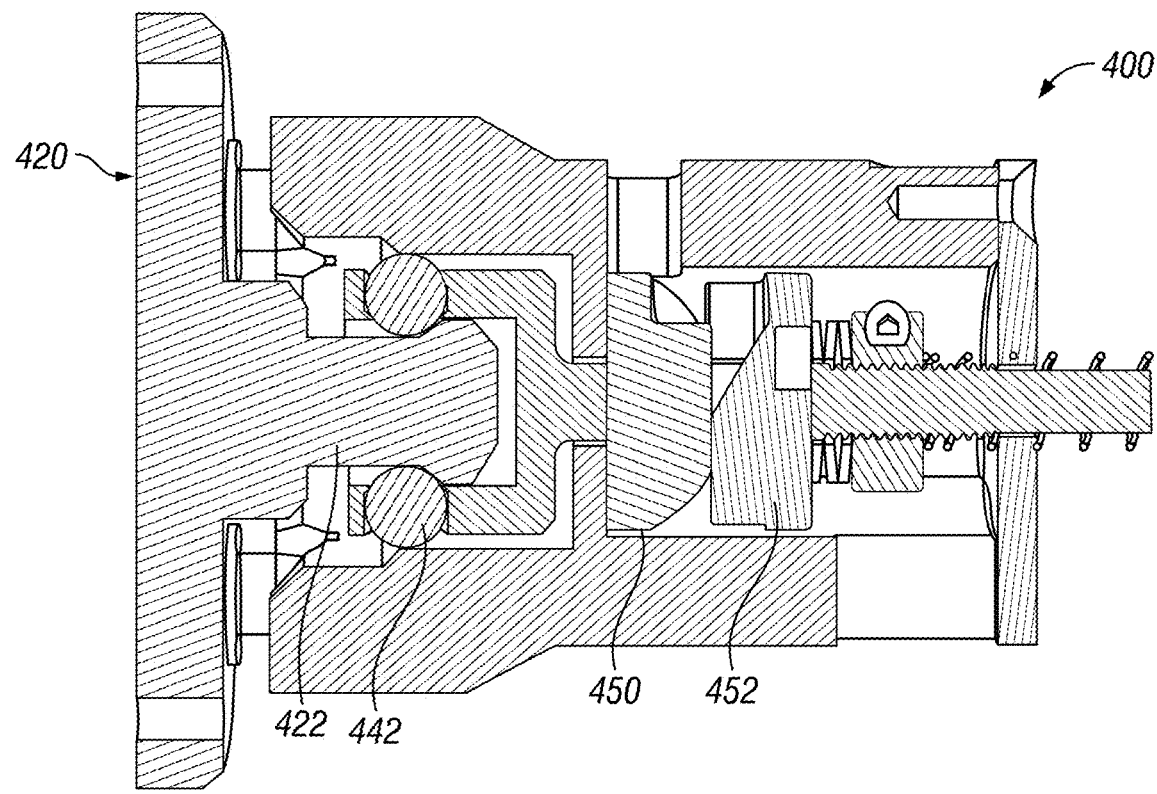
Figure 4J:
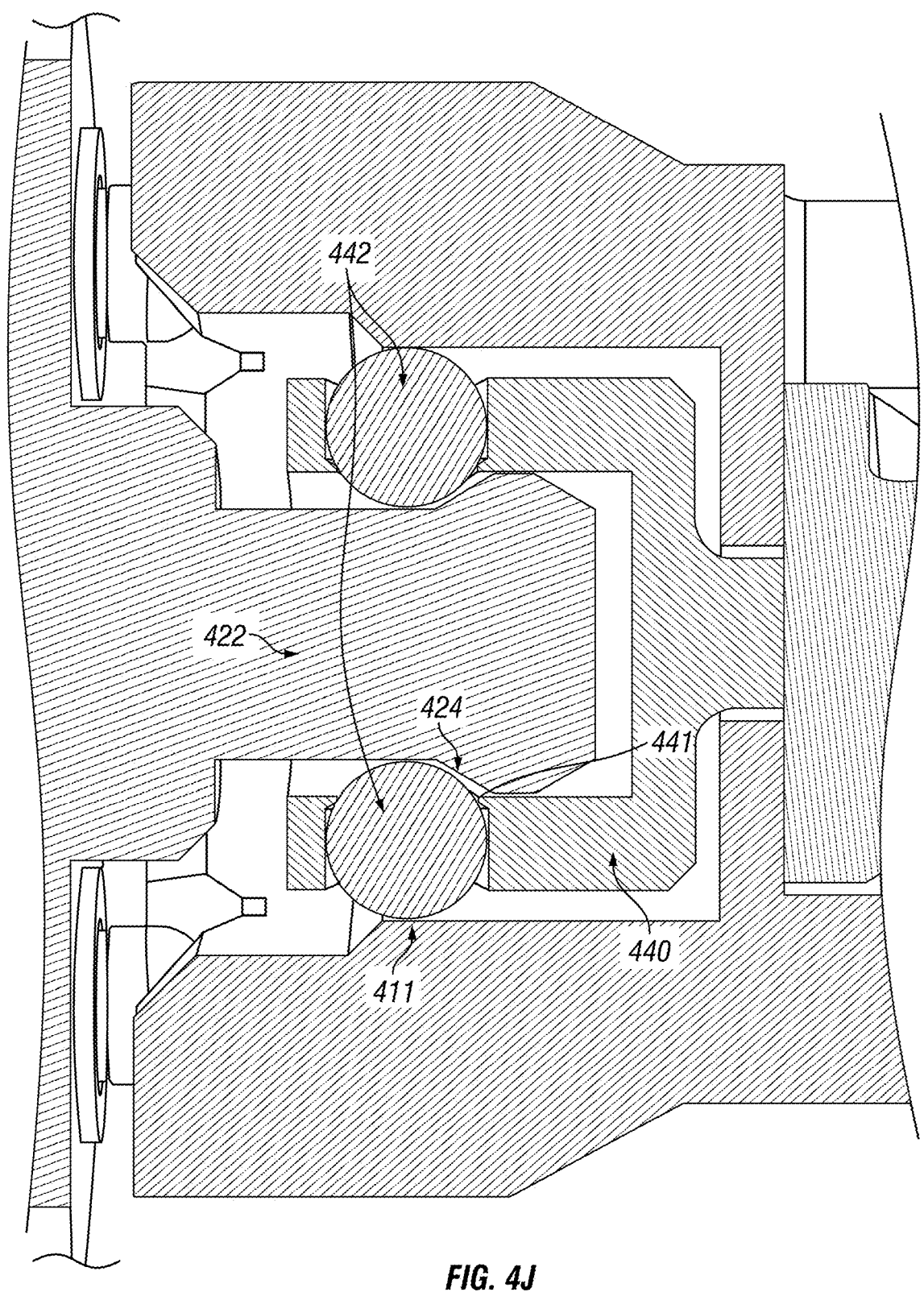

FIGS. 4H-4L are cross-sectional side views of the coupler 400 in various states (e.g., unlocked and locked). FIG. 4H illustrates an initial engagement state where surfaces of the post 422 are in contact with the ball bearing 442 within the ball bearing holder 440. The handle 454 (not shown) and the face cams 450, 452 are in an unlocked position. FIG. 4I illustrates a locked position of the coupler 400 after rotation of the handle 454 (not shown) to a locked position. The rotation of the handle 454 is converted into translational motion of the face cams 450, 452 along the Y-axis such that the first face cam 450 and the second face cam 452 are maximally separated. The ball bearing holder 440 coupled to the face cams 450, 452 is thereby translated along the Y-axis to bring the ball bearings 442 and second portion 420 further into the first portion 410. The contact between the ball bearings 442 and the surfaces of the first portion 410 and the second portion 420 securely engage and lock the first portion 410 to the second portion 420. FIG. 4J is a detailed view of the locking mechanism of the coupler 400. The ball bearing holder 440 in a locked position translates the ball bearings 442 into the first portion 410 to make contact with a contact surface 411 of the first portion 410, a ball bearing lip 441 of the ball bearing holder 440, and a second surface 424 of the post 422. These contact forces are sufficient to constrain the translation of the first portion 410 and the second portion along the Y-axis until the handle 454 is rotated to an unlocked position. In other words, the coupler 400 is self-locking in that the coupling will not become disengaged without user input.

Figure 4K:
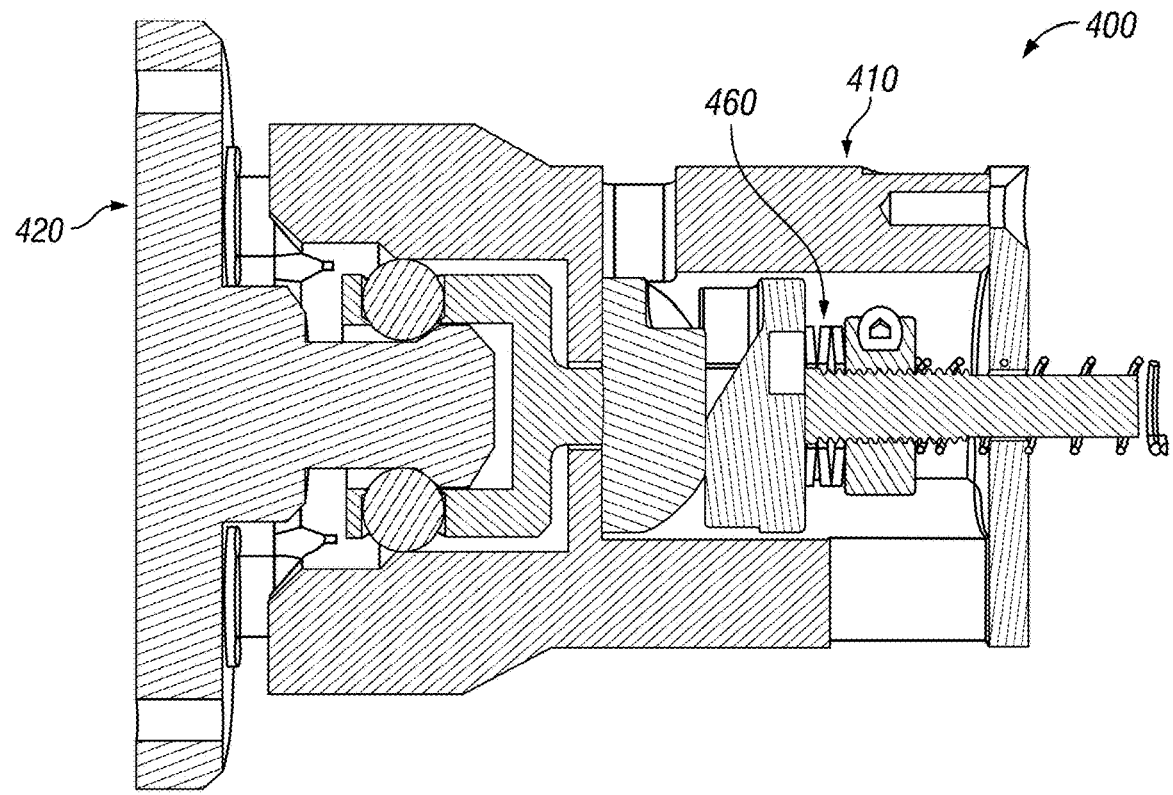
Figure 4L:
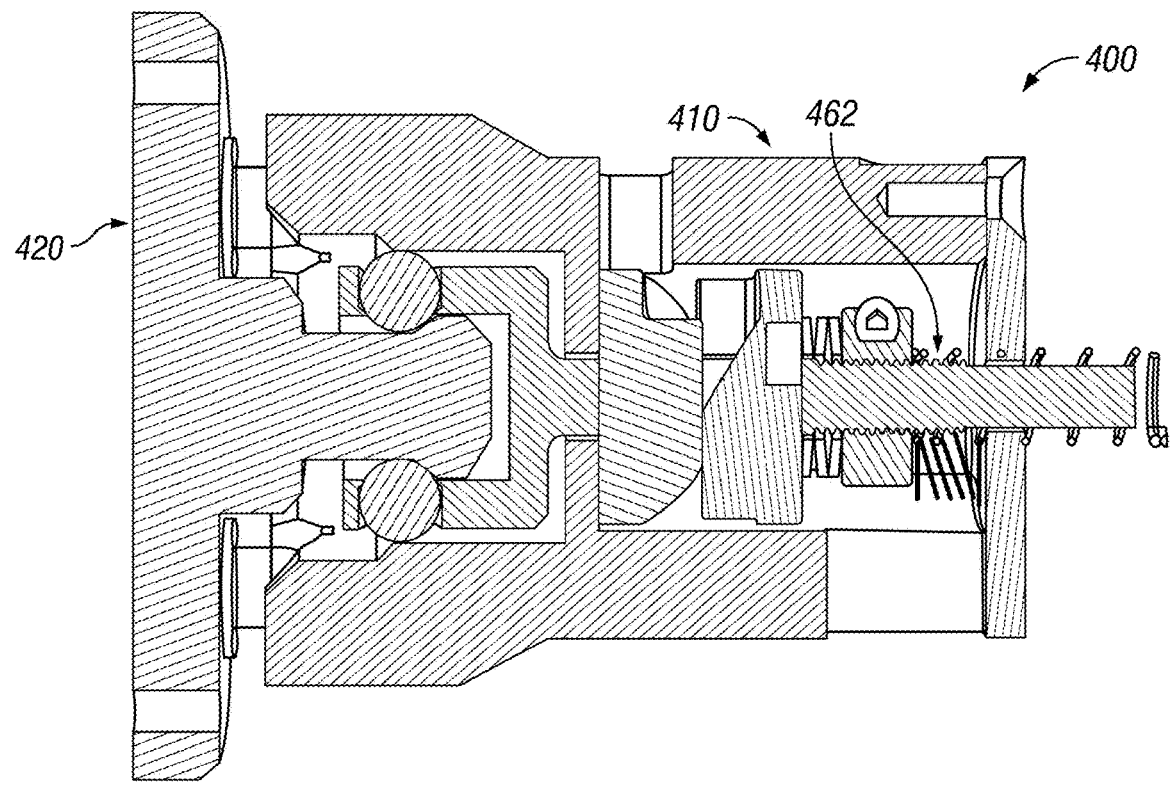

FIG. 4K illustrates a set of Belleville washers 460 coupled to a threaded shaft of the ball bearing holder 440. The Belleville washers 460 may be configured to apply a holding force to ball bearing holder 440. In some embodiments, the Belleville washers may apply between about 200 lb force and about 300 lb force. FIG. 4L illustrates a spring 462 (e.g., compression spring) coupled between an end of the housing of the first portion 410 and the Belleville washers 460. The spring 462 may be configured to provide the spring force to reset the position of the ball bearing holder 440 and hold the handle 454 in the unlocked position. The spring 462 may be configured to bias the ball bearing holder 440 into an unlocked position such that when a user rotates the handle 454 to an unlocked position, the ball bearing holder 440 will translate along the Y-axis towards an initial position such as shown in FIG. 4F. The Belleville washers 460 may be configured to vary a force of the lock.

Figure 5:
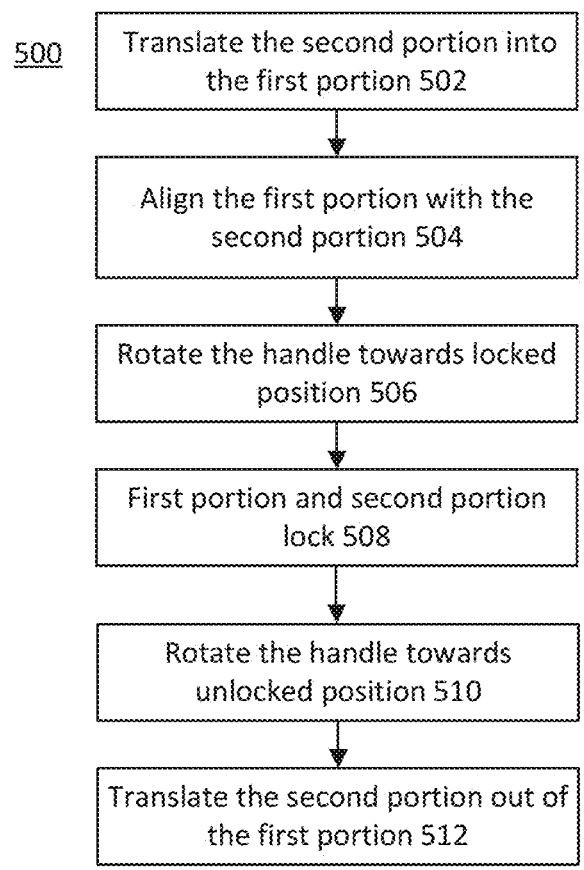
FIG. 5 is a flowchart of a method of attaching a robotic arm to a surgical table, according to an embodiment.

FIG. 5 is a flowchart of a method 500 of coupling a robotic arm to a surgical table, such as by using any of the couplers described herein. The method 500 includes translating at 502 a second portion (e.g., robotic arm base portion) of a coupler into a first portion of the coupler (e.g., mounting portion of a surgical table top) (FIG. 4F). A post of the second portion may begin to align at 504 as the post moves into the first portion (FIG. 4C). The locking mechanism of the first portion (e.g., ball bearing holder, ball bearings, face cams, handle) will not engage if the alignment element(s) of the second portion are not aligned with the first portion. When the post is in an initial engagement state with the ball bearing holder (FIG. 4H), the handle may be rotated at 506 to rotate the two face cams. In some embodiments, the lock may rotate about 90 degrees from an unlocked position to a locked position. As the lock travels through its arc, the face cams move apart and translate the ball bearing holder further into the first portion (FIG. 4I). The ball bearing holder engages the set of ball bearings so as to press the ball bearings against surfaces of the first portion and the second portion (FIG. 4J). The pressing force locks at 508 the first and second portions together. As the ball bearing holder is translated into the first portion in response to handle rotation into the locked position, a set of kinematic mounts engage with corresponding V-grooves to precisely align the first and second portions (FIG. 4E). In order to decouple the coupler 400, a user may rotate the handle at 510 towards the unlocked position. This rotates the face cams towards each other and translates the ball bearing holder towards the second portion, thereby releasing the force between the ball bearings and the housing of the first portion. With the lock disengaged, the second portion may be fully decoupled from the first portion by translating the second portion out of the first portion at 512.

Figure 6A:
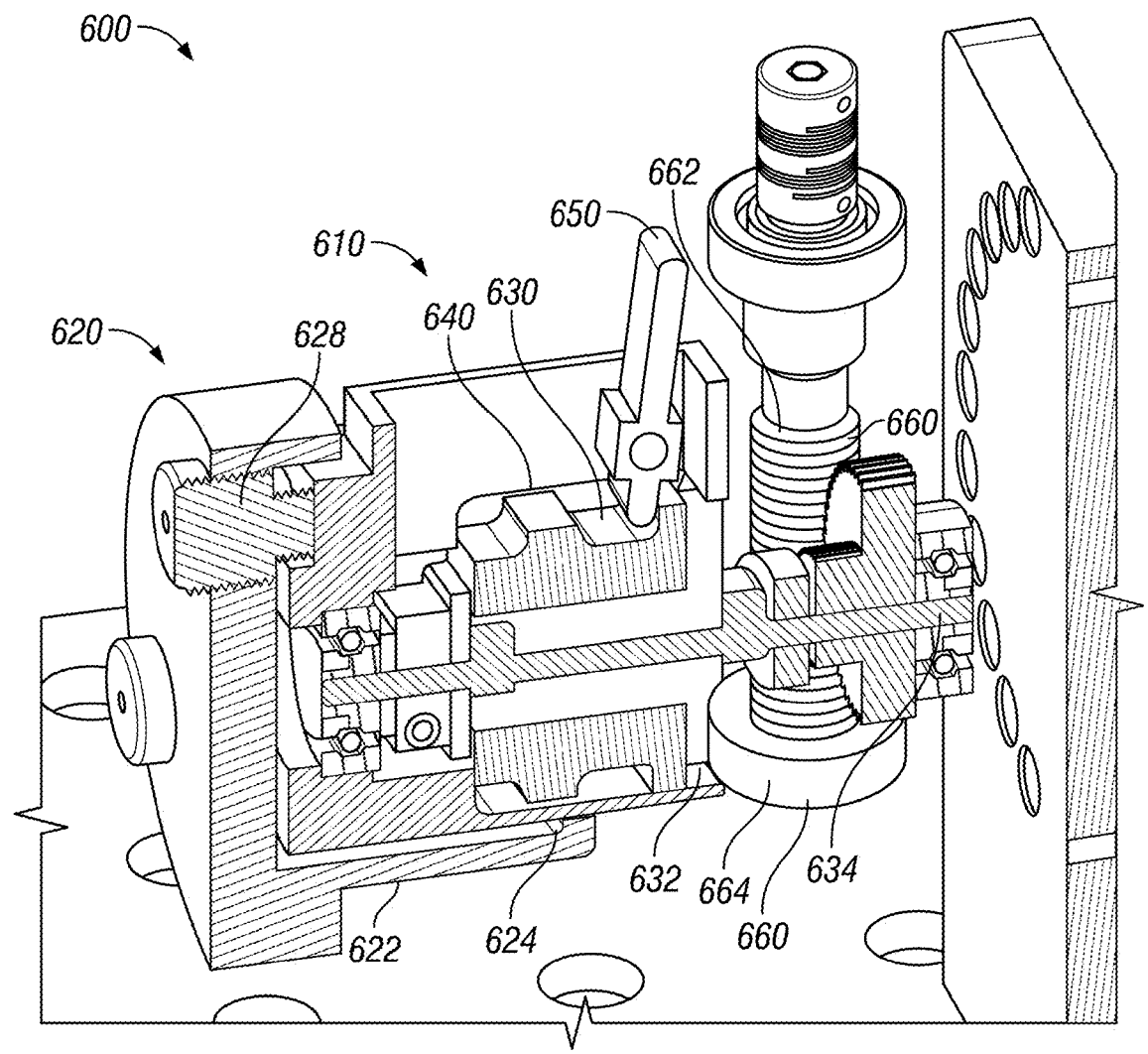
FIGS. 6A-6C illustrate a coupler, according to an embodiment.
Figure 6B:
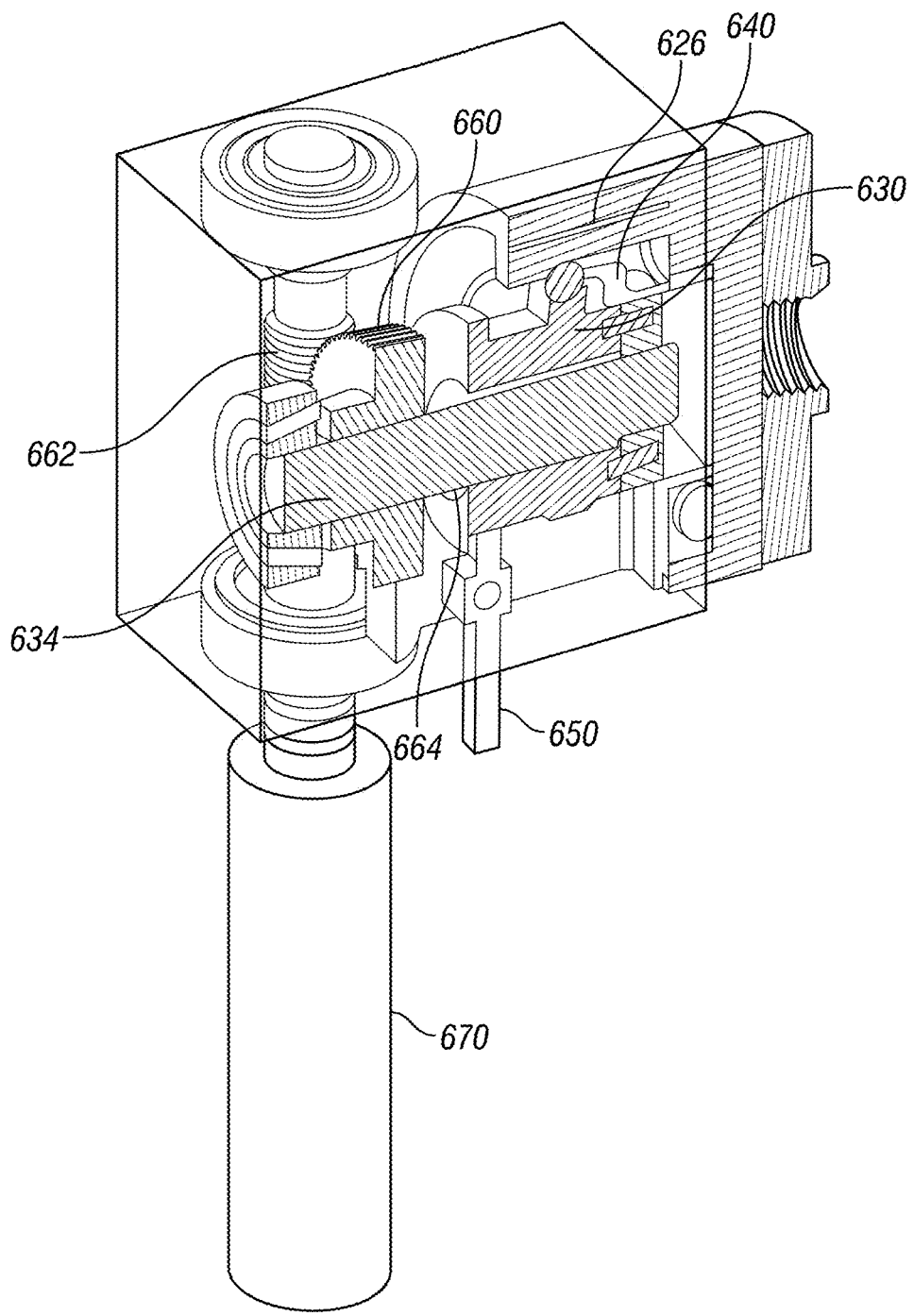
Figure 6C:
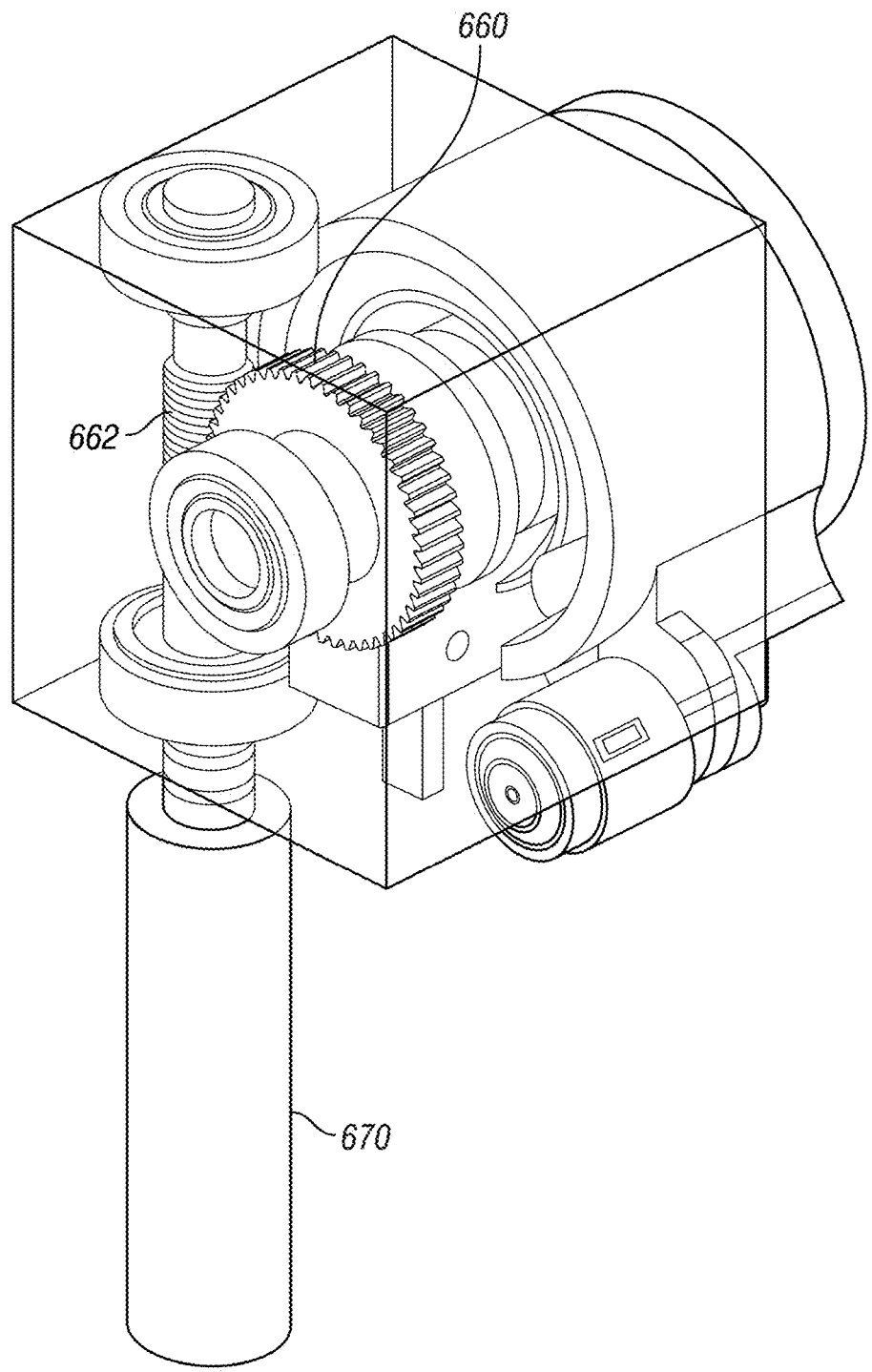

FIGS. 6A-6C are perspective views of an embodiment of a coupler 600 driven by a motor and having a manual coupling mechanism that may be used to couple and decouple in cases where power is lost and/or emergency operation. The coupler 600 may include a first portion 610 and a second portion 620. Coupling of the first portion 610 and the second portion 620 forms a secure mating connection where six degrees of freedom are constrained. The second portion 620 may include a post 622 configured to surround the first portion 610. The post 622 may be translated along a Y-axis to mate with the first portion 610 to constrain the translation along the Y-axis.

The first portion 610 may include a set of ball bearings 640, a cam 630 coupled to a bushing 632, and a shaft 634. The set of ball bearings 640 may include four or more ball bearings equally spaced apart along a circumference of the first portion 610. The set of ball bearings 640 may be moved by a locking mechanism configured to securely engage and lock the first portion 610 to the second portion 620. The cam 630 is configured to translate along the Y-axis relative to a housing of the first portion 610 when driven by a motor and/or handle 650. The post 622 and the cam 630 experience Hertzian stresses based on the curvature of those surfaces. The curvature and material properties, along with the ball bearing 640 diameter and material may be configured to generate contact conditions that do not deteriorate those surfaces. Movement of a cam 630 into a locked position will position the set of ball bearings 640 in holding contact force between surfaces of the post 622 of the second portion and surfaces of the cam 630. The cam 630 and the bushing 632 may be configured to be slidable along the shaft 634. Movement of the cam 630 along the shaft 634 may vary a contact force of the set of ball bearings 640 against a contact surface of the post 622 when the first portion 610 and the second portion 620 are translated into each other. A contact surface of the post 622 may include a post lip 624 configured to retain the ball bearings 640 within the second portion 620. The ball bearings 640 move within a predetermined range first portion 610 and serve as a locking mechanism to apply forces to both the first portion 610 and second portion 620 to securely lock them together and form a coupling between the first portion 610 and the second portion 620.

The cam 630 may be driven by a worm gear including a worm wheel 660 and worm 662) using a motor 670 to couple and decouple the first portion 610 and the second portion 620. The motor 670 may be, for example, a brushless DC motor. The first portion 610 may include a handle 650 configured to permit a user to actuate in order to slide the cam 630 along the shaft 634 and engage or release the set of ball bearings 640 from contact with a contact surface of the post 622. The handle 650 may rotate between a locked position and an unlocked position and transition the coupler 600 between a locked configuration and an unlocked configuration. FIG. 6A illustrates a locked position of the coupler 600. In the locked position, the contact between the ball bearings 640 and the post 622 of the second portion 620 and the cam 630 securely engage and lock the first portion 610 to the second portion 620.

Rotation of the handle 650 towards the unlocked position is converted into translational motion of the cam 630 along the Y-axis to disengage contact between the ball bearings 640 and surfaces of the post 622 and the cam 630. A spring 664 may be coupled between the bushing 632 and the worm wheel 660 and configured to provide the spring force to reset the position of the cam 630 into an unlocked position where the cam 630 is biased towards the worm gear.

As shown in FIG. 6B, the post 622 may include one or more relief cuts 626 that may be configured to provide a desired level of holding force between the first portion 610 and the second portion 620. For example, a wider and/or longer gap in the relief cuts 626 may reduce the maximum holding force between the first portion 610 and the second portion 620. The second portion 620 may further include a post lip 624. In some embodiments, the coupler 600 may include kinematic mounts, V-grooves, and/or alignment elements as described herein.

Figure 7A:
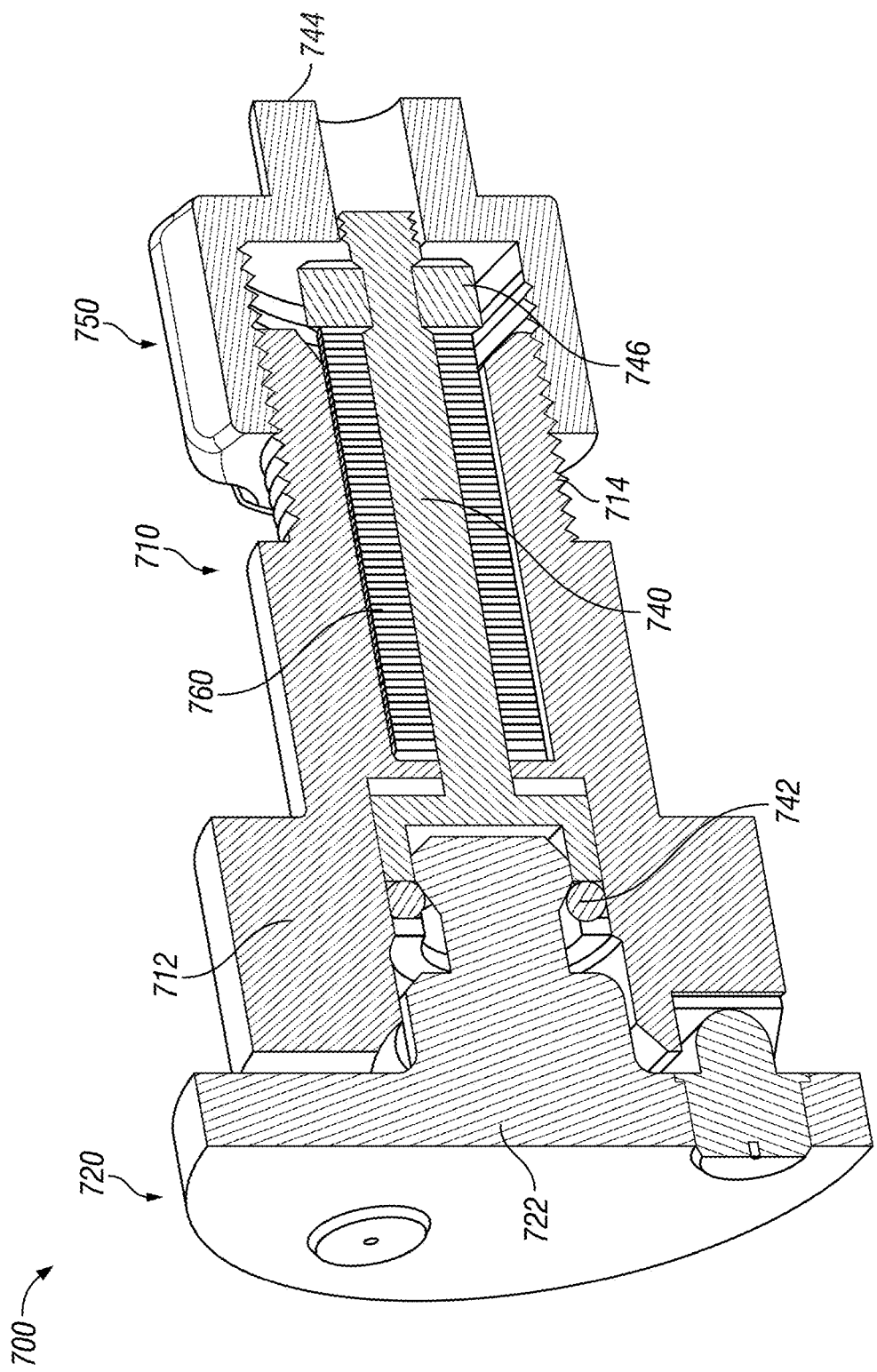
FIGS. 7A-7D illustrate a coupler, according to an embodiment.

In some embodiments, a rotational collet may be used to couple and decouple a first and second portion of a coupler. FIG. 7A is a cross-sectional perspective view of an embodiment of a coupler 700. The coupler 700 includes a first portion 710 having an outer housing 712 and a first portion threading 714. The coupler 700 also includes a second portion 720 having a post 722. That may be translated along a Y-axis to mate with the first portion 710 to constrain translation along the Y-axis. Coupling of the first portion 710 and the second portion 720 forms a secure mating connection where six degrees of freedom are constrained. The first portion 710 may include a collet 750 configured to lock and secure the coupling between the first portion 710 and the second portion 720. The first portion 710 includes a ball bearing holder 740 configured to receive, engage, and lock with the post 722. The ball bearing holder 740 is configured to hold the ball bearings 742 and surround the post 722. The ball bearing holder 740 is configured to translate along the Y-axis relative to a housing of the first portion 710 when the collet 750 is rotated. The translation of the ball bearing holder 740 into the first portion 710 presses the ball bearings 742 into the first portion 710, the ball bearing holder 740, and the post 722. As illustrated herein, the ball bearing holder 740 may include a lip on each ball bearing pocket configured to retain the ball bearing 742 within the holder 740 when the ball bearings 742 are not in contact with the post 722. These surfaces experience Hertzian stresses based on the curvature of the surfaces. The curvature and material properties, along with the ball bearing 742 diameter and material may be configured to generate contact conditions that do not deteriorate the surfaces. The ball bearings 742 move within a predetermined range within the ball bearing holder 740 and serve as a locking mechanism to apply forces to both the first portion 710 and second portion 720 to securely lock them together and form a coupling between the first portion 710 and the second portion 720.

A set of Belleville washers 760, a lock collar 746, and a thrust bearing 744 may be coupled to the ball bearing holder 740. The collet 750 may be configured to rotate about the first portion 710 so as to lock and unlock the post 722 from the ball bearing holder 740. An outer surface of the collet 750 may be a locking knob that the user can rotate to couple and decouple the first portion 710 and second portion 720.

Figure 7B:
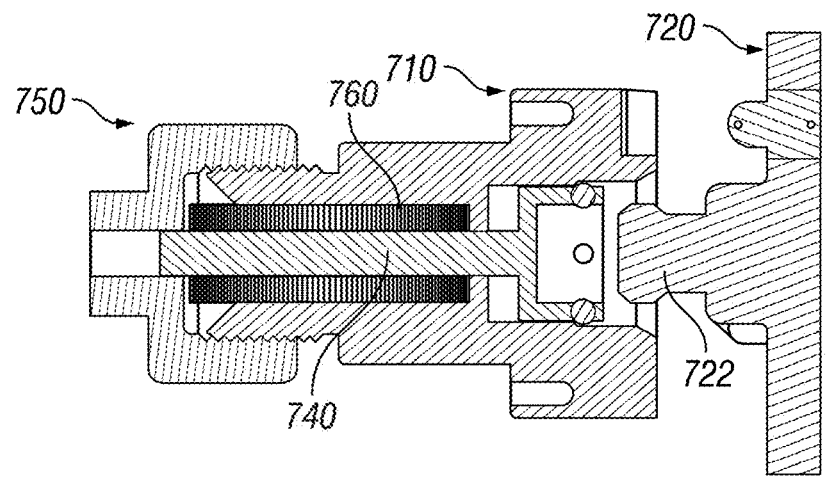
Figure 7C:
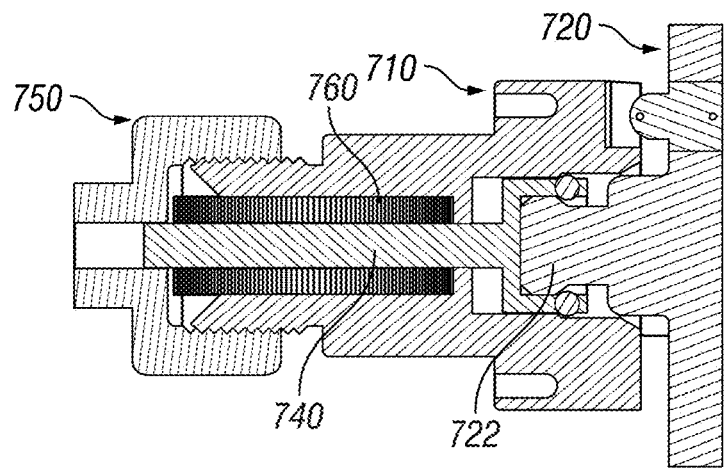
Figure 7D:
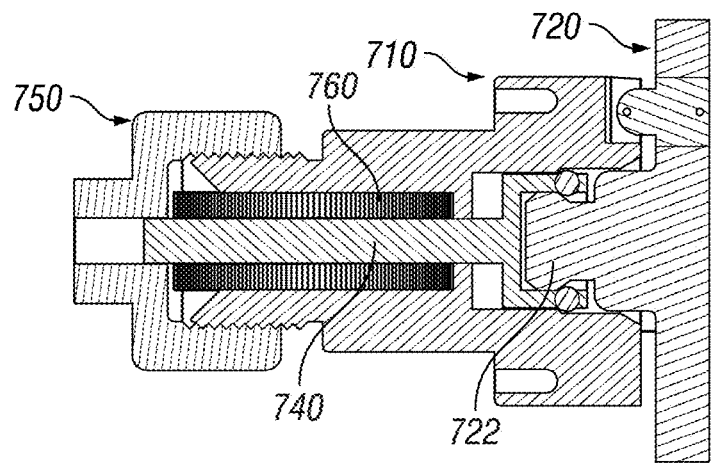

FIGS. 7B-7D are cross-sectional side views of the coupler 700 in different coupling states. In the decoupled state shown in FIG. 7B, the set of Belleville washers 760 are compressed and the knob portion (of the collet 750) is turned in. The second portion 720 is being translated into the first portion 710 but has not made contact with the ball bearing holder 740. In FIG. 7C, the first portion 710 and second portion 720 have made an initial engagement where the post 722 contacts the ball bearing holder 740. The collet 750 is in a first position corresponding to an unlocked position of the coupler 700. The set of Belleville washers 760 are fully compressed and the knob portion of the collet 750 is turned in. In FIG. 7D, the collet knob is rotated so as to be turned out so as to draw the ball bearing holder 740 into the first portion 710 and lock the post 722 to the first portion 710. The set of Belleville washers 760 are at a work load compression. Both the post 722 and the first portion 711 are held by a holding force using a set of ball bearings 742. The set of ball bearings 742 may include four or more ball bearings equally spaced apart along a circumference of ball bearing holder 740. In some embodiments, the coupler 700 may include kinematic mounts, V-grooves, and/or alignment elements as describe herein.

Kinematic Mount with Lead Screw Connection

Figure 8:
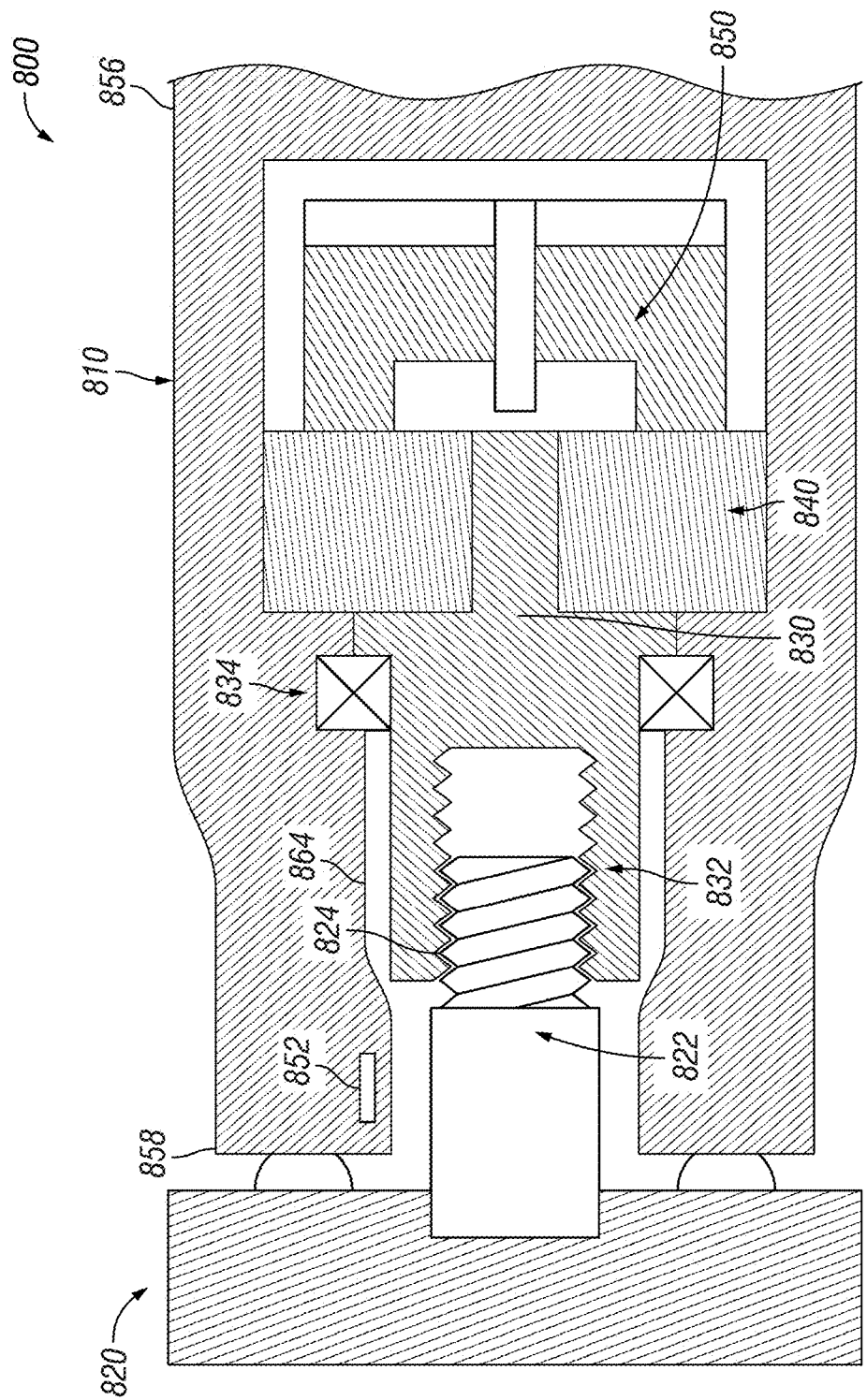
FIG. 8 is a cross-sectional side view of a coupler, according to an embodiment.

FIG. 8 is a cross-sectional side view of an embodiment of a coupler 800 driven by a motorized locking mechanism that may generate high forces to ensure the coupling is constrained and maintained in six degrees of freedom even in the presence of external loads (e.g., robotic arm static and inertial loads during a surgical procedure). The coupler 800 may include a first portion 810 and a second portion 820. Coupling of the first portion 810 and second portion 820 forms a secure mating connection where six degrees of freedom are constrained. From this view, it can be seen that first portion 810 includes a first end 856 (the end coupled to the robotic arm) and a second end 858 (the end coupled to second portion 820), and an interior cavity 864 formed within first portion 810, between the first and second ends.

An opening to the interior cavity 864 is formed through the second end 858. The first portion 810 may include a locking mechanism coupled to a drive mechanism configured to lock and secure the coupling between the first portion 810 and the second portion 820. The second portion includes a post 822 that may be translated along a Y-axis to mate with the first portion 810 to constrain translation along the Y-axis. The post 822 includes a lead screw 824 that may be coupled to a corresponding threaded portion 832 of a rotatable collet 830. A motor 850 may drive the collet 830 to rotate about the lead screw 924-824 in a first direction so as to translate the lead screw 824 into the first portion 810 along the Y-axis. In this manner, the collet 830 may be engaged with the post 822 to securely lock and couple the first portion 810 to the second portion 820. Rotation of the collet 830 in a second direction opposite the first direction may translate the lead screw 824 out of the first portion 810 along the Y-axis. In some embodiments, the pitch angle of the lead screw 824 may be between about 2 degrees and about 30 degrees. In some embodiments, the pitch angle of the lead screw 824 may be between about 10 degrees and about 15 degrees. In some embodiments, the pitch angle of the lead screw 824 may be configured to prevent the lead screw 824 from being backdriven.

The motor 850 may be coupled to a gearbox 840 and configured to rotate the collet 830. The collet 830 may be coupled to one or more bearings 834. The bearings 834 may be, for example, a deep groove ball bearing. The gearbox 840 may be, for example, a planetary or harmonic gear box and may have a gear ratio of about 20 to about 200. The motor 850 may be, for example, a brushless DC motor. In some embodiments, the motorized locking mechanism may generate a force of at least 500 N. In some embodiments, the motorized locking mechanism may generate a force of at least 1400 N.

The motor 850 may be coupled to a controller (not shown) configured to receive input commands from a user. For example, a robotic arm may include a switch that may input a coupling command to lock and unlock the first portion 810 from the second portion 820 by driving the lead screw in either direction, thereby attaching and detaching the robotic arm from a surgical table. The switch may be provided on a surgical table, medical cart, and/or portable computing device.

In some embodiments, the coupler 800 may include a connection sensor 852 configured to detect coupling and decoupling between the first portion 810 and the second portion 820. In some embodiments, the connection sensor may include one or more of a force sensor, Hall effect sensor, and electrical switch located on either the first portion 810 and the second portion 820 (e.g., at an interface between the first portion 810 and the second portion 820). In some embodiments, the connection sensor may include an encoder on the motor 850. A controller may be configured to drive the collet 830 using the motor 850 until a coupling or decoupling has been detected.

In some embodiments, the coupler 800 may include kinematic mounts, V-grooves, and/or alignment elements as described herein. The motorized locking mechanism of coupler 800 may reduce user error in coupling the first portion 810 to the second portion 820 including partial coupling and decoupling, usability risk (e.g., non-intuitive use), and increase safety (e.g., robotic arm falling to the floor on onto a user's foot or leg).

Conical Arm Base Connection

Figure 9A:
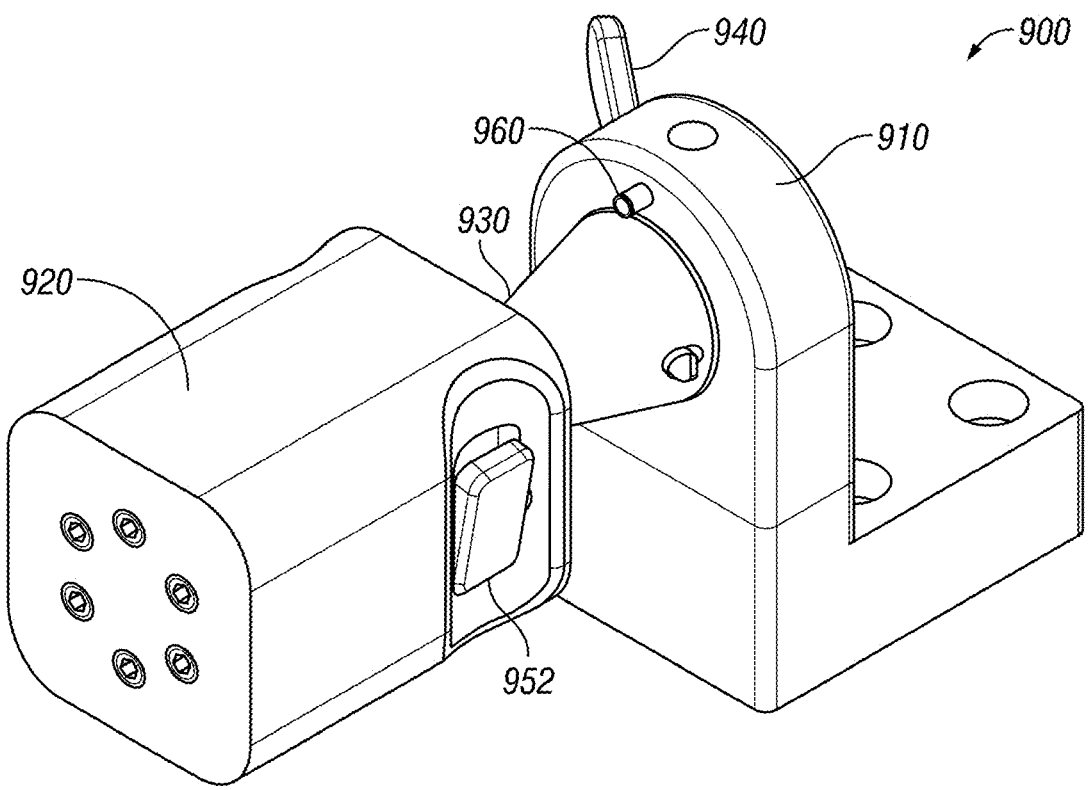
Figure 9B:
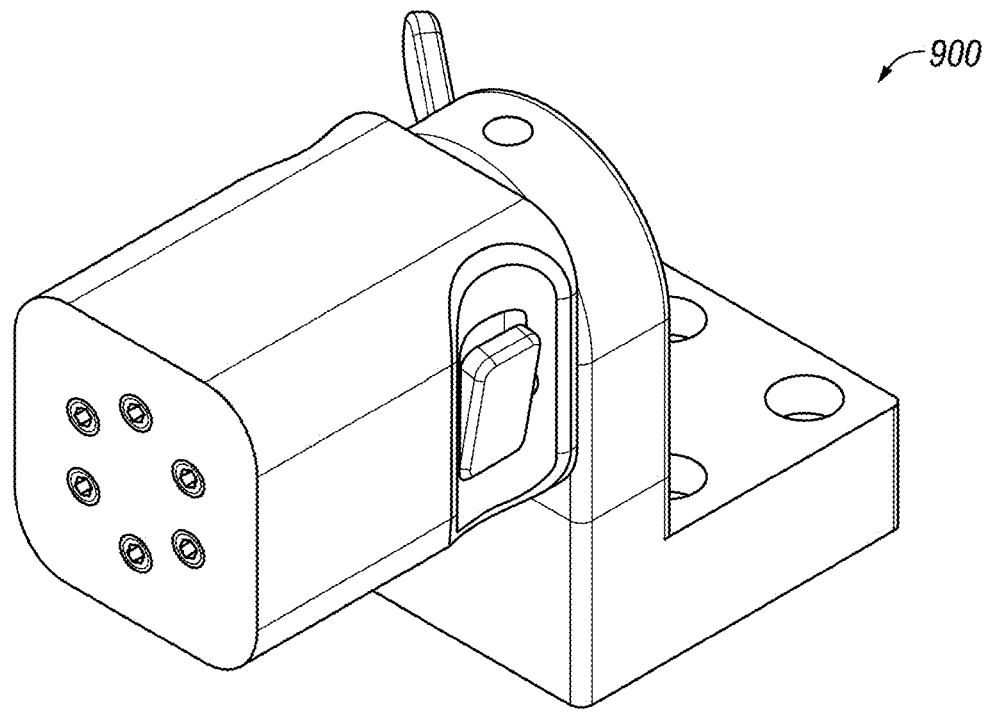

FIG. 9A is a perspective side view of an embodiment of a coupler 900. The coupler 900 can include a first portion 910 such as a base portion for mounting to a surgical table (e.g., surgical table 300). The coupler 900 can include a second portion 920 (e.g., arm adapter) such as a terminal base portion for a robotic arm. Coupling of the first portion 910 and second portion 920 forms a secure mating connection where six degrees of freedom are constrained. The first portion 910 includes a handle 940 configured to lock and secure the coupling between the first portion 910 and second portion 920, and an alignment protrusion 960 configured to contact a corresponding alignment hole (not shown), as described herein. The first portion 910 includes a cone 930 that may be translated along a Y-axis to mate with a conical receiving hole 912 (FIG. 9D) of the second portion 920 to constrain translation along the Y-axis. FIG. 9B illustrates the X-axis, Y-axis, and Z-axis relative to the coupler 900. It should be appreciated that the first portion 910 and second portion 920 may be reversed such that the first portion 910 couples to a surgical table and the second portion 920 couples to a robotic arm.

Figure 9D:
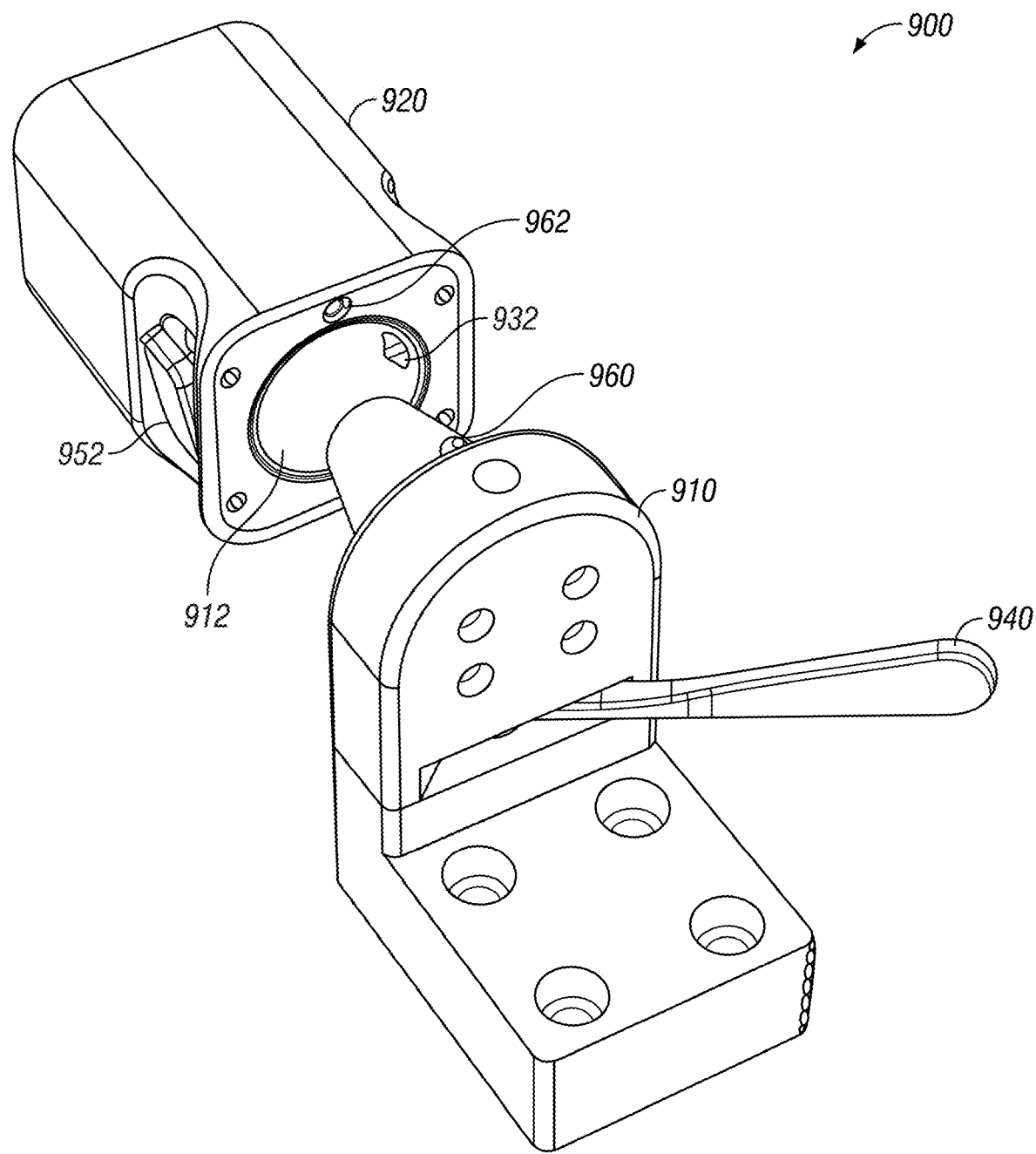

The first portion 910 may include one or more alignment protrusions 960 configured to contact and slide into and mate with a corresponding alignment hole 962 in the second portion 962. The alignment protrusion 960 is asymmetrical in that alignment of the protrusion 960 with the second portion 920 is configured to prevent a user from inserting the first portion 910 incorrectly into the second portion 920. This process may be referred to herein as registration. The shape of the alignment protrusion 960 is shown having a cylindrical shape, but is not particularly limited. For example, the alignment protrusion 960 may include a spring loaded/split pin. When the alignment protrusion 960 is misaligned with the alignment hole 962, the cone 930 of the first portion 910 will not be translated along the Y-axis sufficiently into the conical hole 912 of the second portion 920 to engage coupling and locking of the first portion 910 to the second portion 920. For example, FIG. 9D illustrates the alignment protrusion 960 of the first portion 910 aligned with the alignment hole 962 of the second portion 920 so as to permit the cone 930 to be fully translated into the second portion 920. Otherwise, the alignment protrusion 960 contacts the housing of the second portion 920 to create a gap between the first portion 910 and the second portion 920 that prevents their coupling.

The cone 930 is configured to provide a large surface area to form a mechanical coupling having rigidity. For example, the cone 930 is configured to couple the first portion 910 and second portion 920 so as to constrain translation in the X-axis and Y-axis, and constrain rotation about the X-axis and Z-axis. The surface of the cone 930 forms mating surfaces that may have tight tolerances and a surface finish ensuring proper contact with the second portion 920. In some embodiments, the contact surface may include a surface roughness configured to increase friction between the first portion 910 and the second portion 920. A taper angle of the cone 930 may be configured for low release forces while maintaining high rigidity of the coupling. In some embodiments, the cone 930 may have a taper angle of about 14 degrees.

In some embodiments, the cone 930 may include edges or planes that contact the alternating mating surface. In some embodiments, a pin 934 may be disposed at a nose of the cone 930 and may be configured to protrude from and recess into a surface of the cone 930. When the handle 940 is rotated to an unlock position, the pin may be configured to protrude from the cone 930 to aid in the release and translation of the second portion 920 away from the first portion 910 by pushing the first portion 910 and second portion 920 away from each other in the event that they remain in contact due to friction.

Figures 9E, 9F:
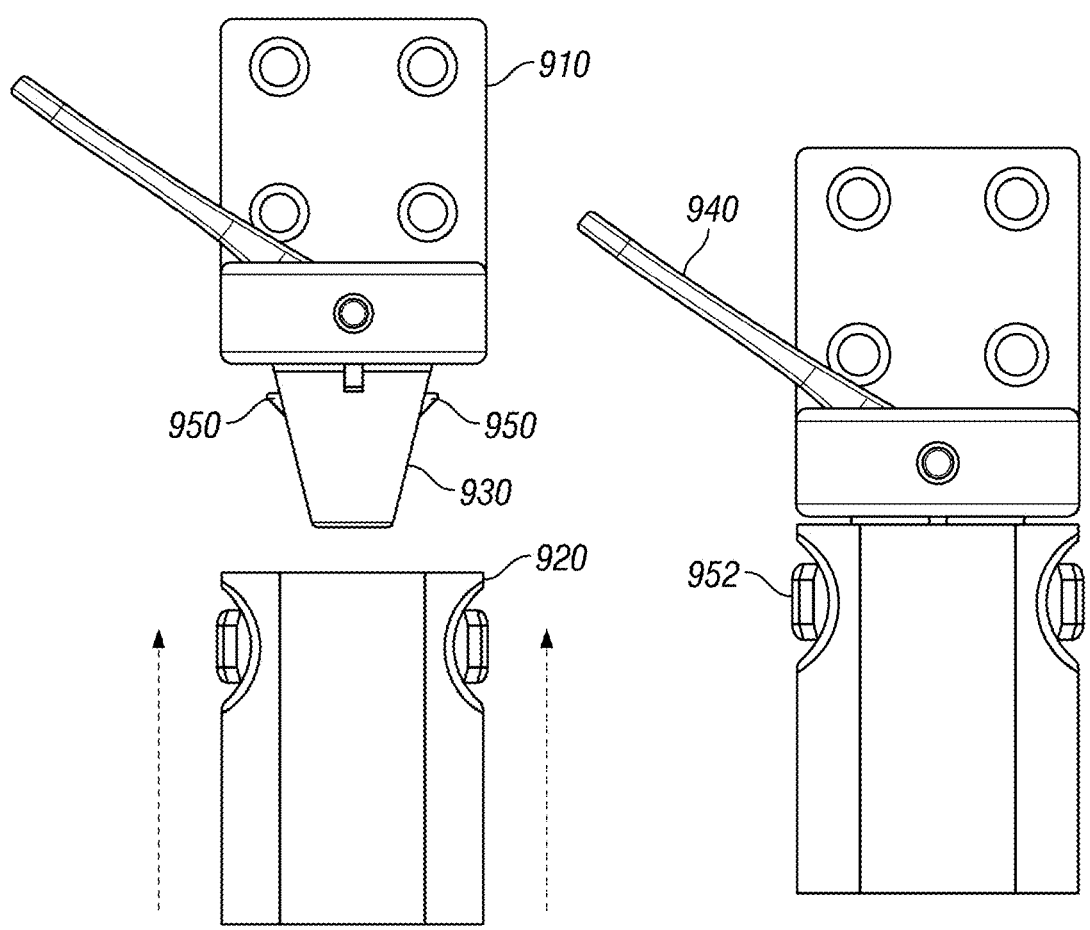

FIG. 9C illustrates a side view of the first portion 910 and second portion 920. The cone 930 may include two or more catches 950 configured to constrain translation of the second portion 920 along the Y-axis. For example, the catches 950 may be disposed along opposite lateral sides of the conical taper of the cone 930. The catches 950 may be configured as an initial locking mechanism (e.g., spring catch) to prevent a robotic arm attached to the second portion 920 from falling out and away from the cone 930 of the first portion 910. The catch 950 may include an angled, flat surface configured to slide easily over a surface of a conical hole 912. The catch 950 may include a tapered portion configured to hold the first portion 910 against the second portion 920. The second portion 920 includes a switch 952 having a corresponding catch 950 configured to move the catches 950 from a first configuration to a second configuration. The catches 950 may be biased to protrude from the cone 930 in the first configuration and be recessed into the cone 930 in the second configuration. FIG. 9E shows the second portion 920 being translated over the cone 930. When the second portion 920 is translated over the cone 930, the catches 950 make contact with the surface of the conical hole 912 and are recessed into the cone 930. The catches 950 advanced over corresponding axial grooves 932 (FIG. 9D) allows the catches 950 to protrude out in the first configuration to thereby couple and secure the first portion 910 to the second portion 920 in an initial lock state, as shown in FIG. 9F. FIG. 9G is a perspective view of the first portion 910 and second portion 920 in the initial lock state. The handle 940 is in an unlocked state throughout the steps shown in FIGS. 9D-9G.

Figure 9H:
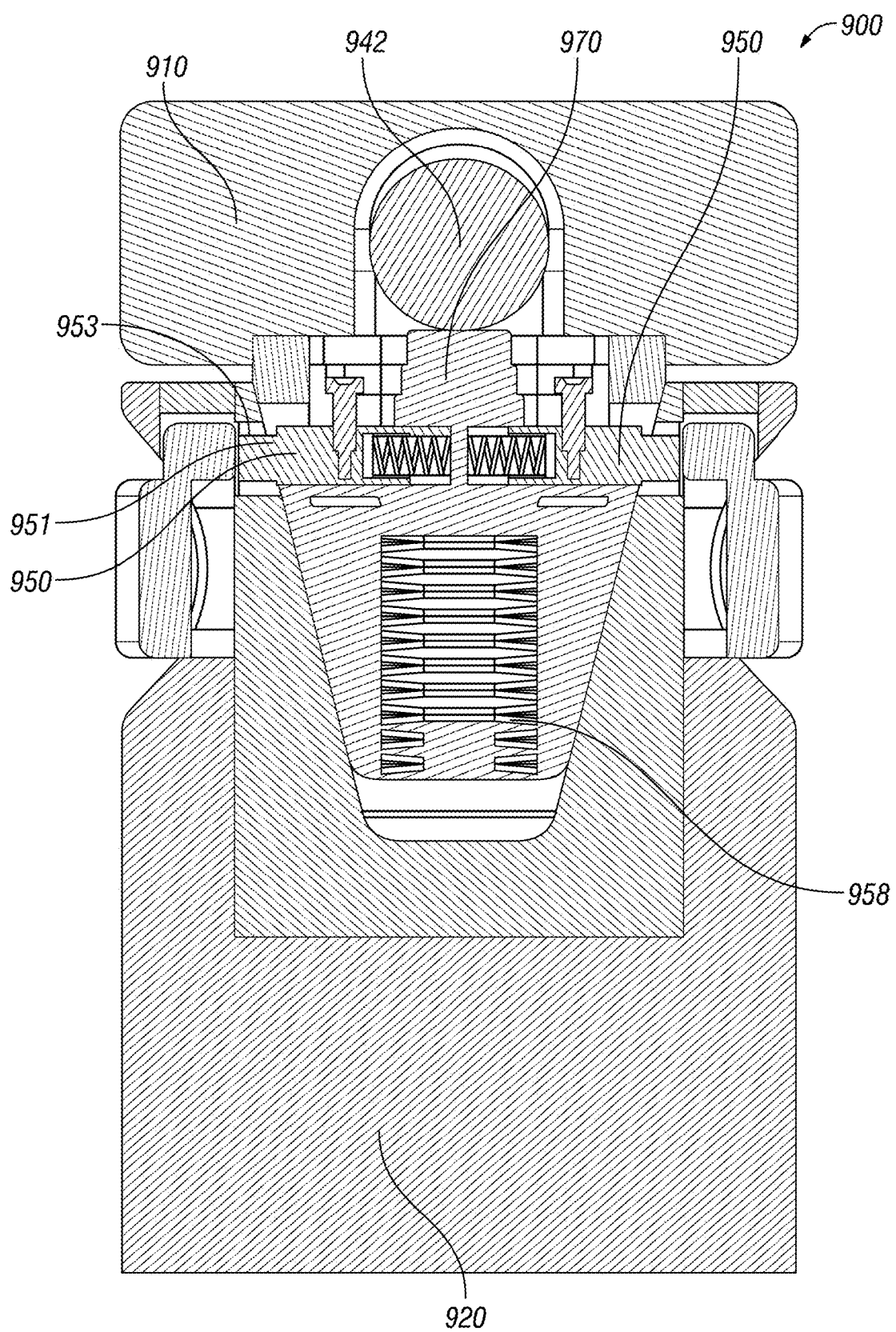
Figure 9I:
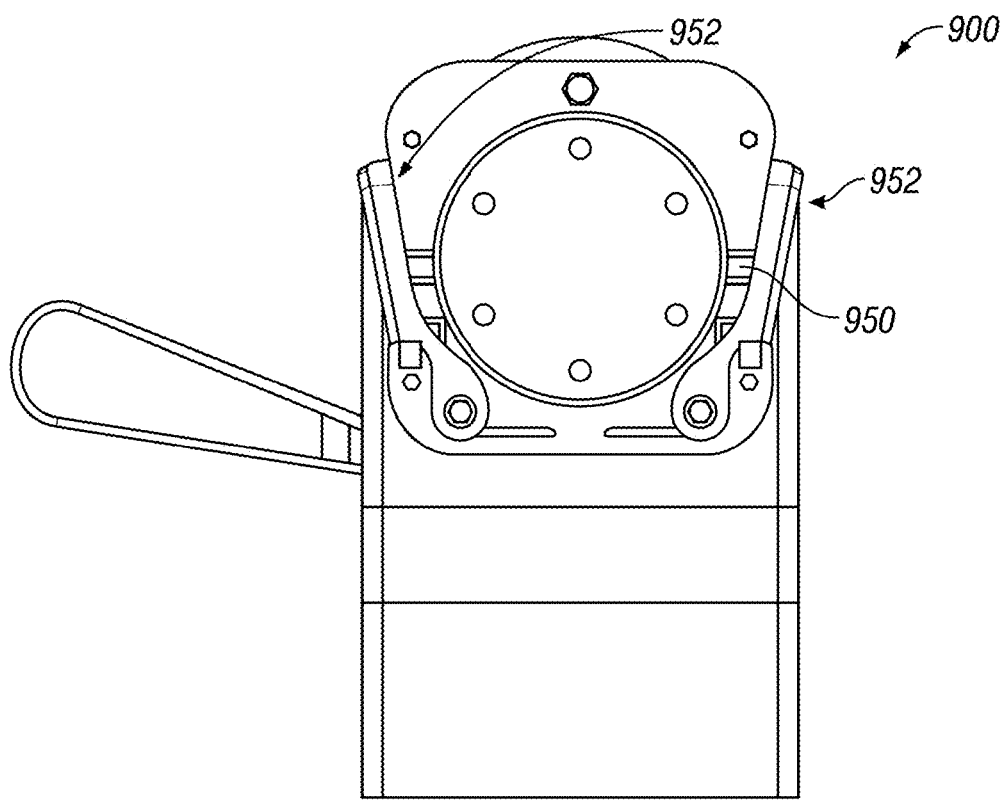
Figure 9J:
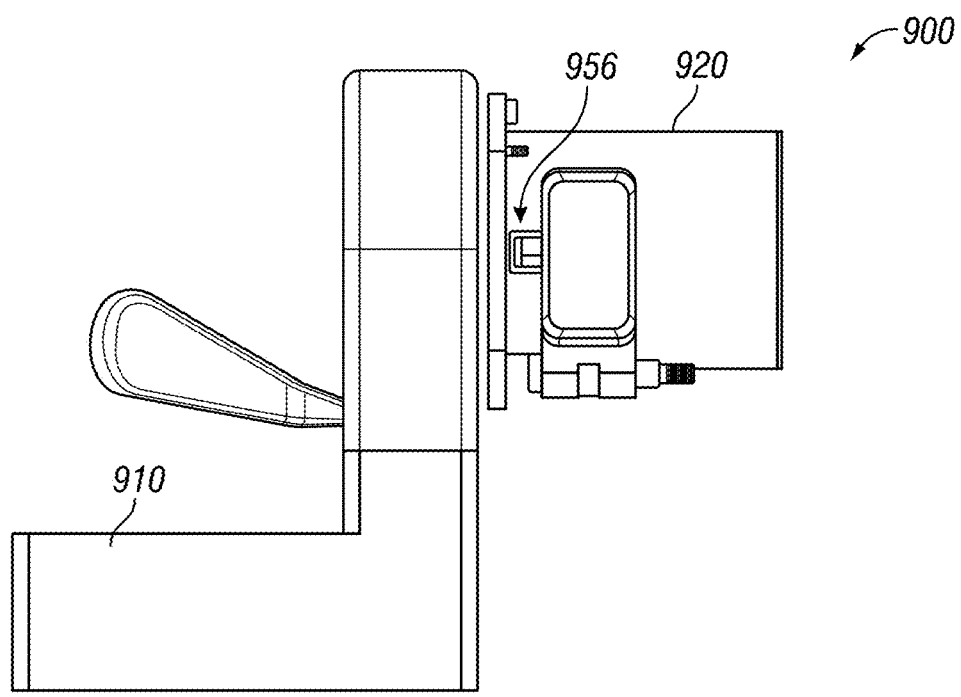
Figure 9K:
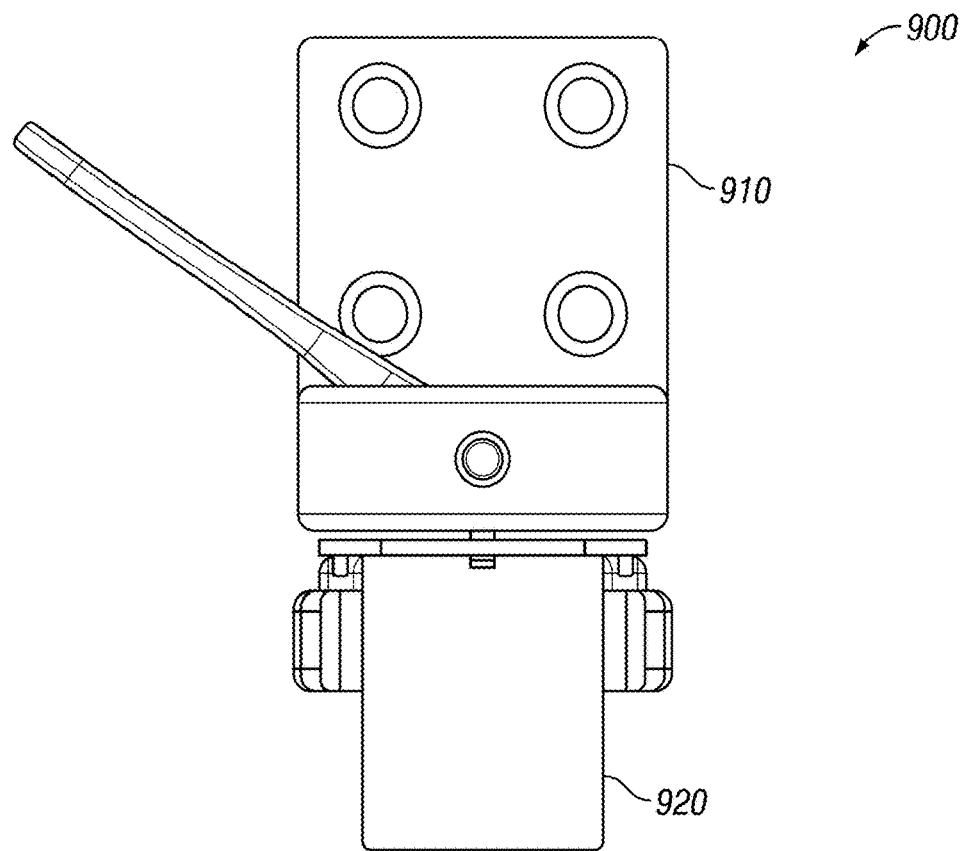
Figure 9L:
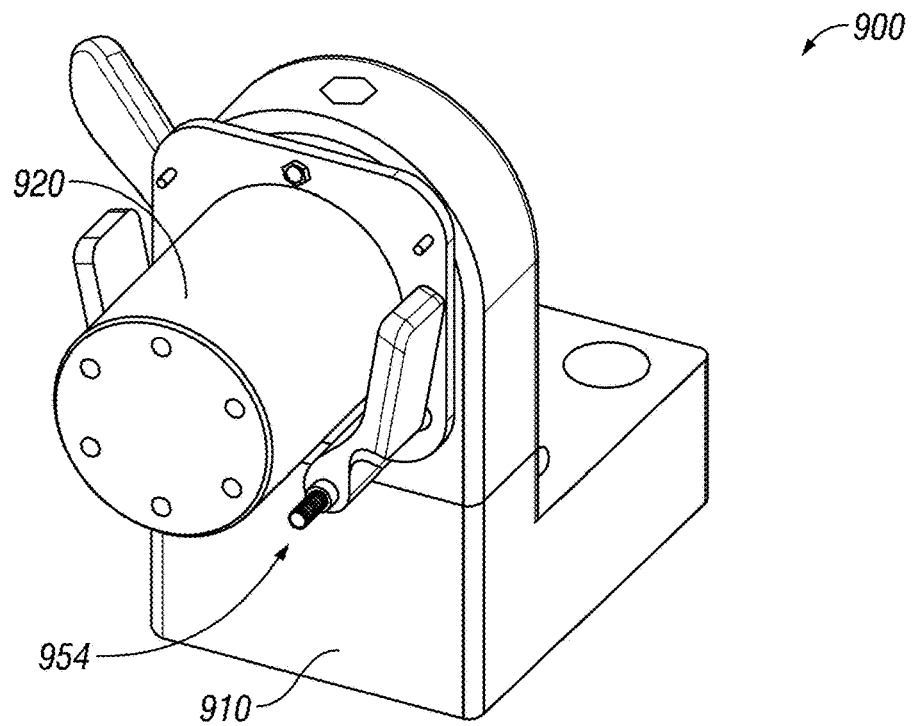
Figure 9M:
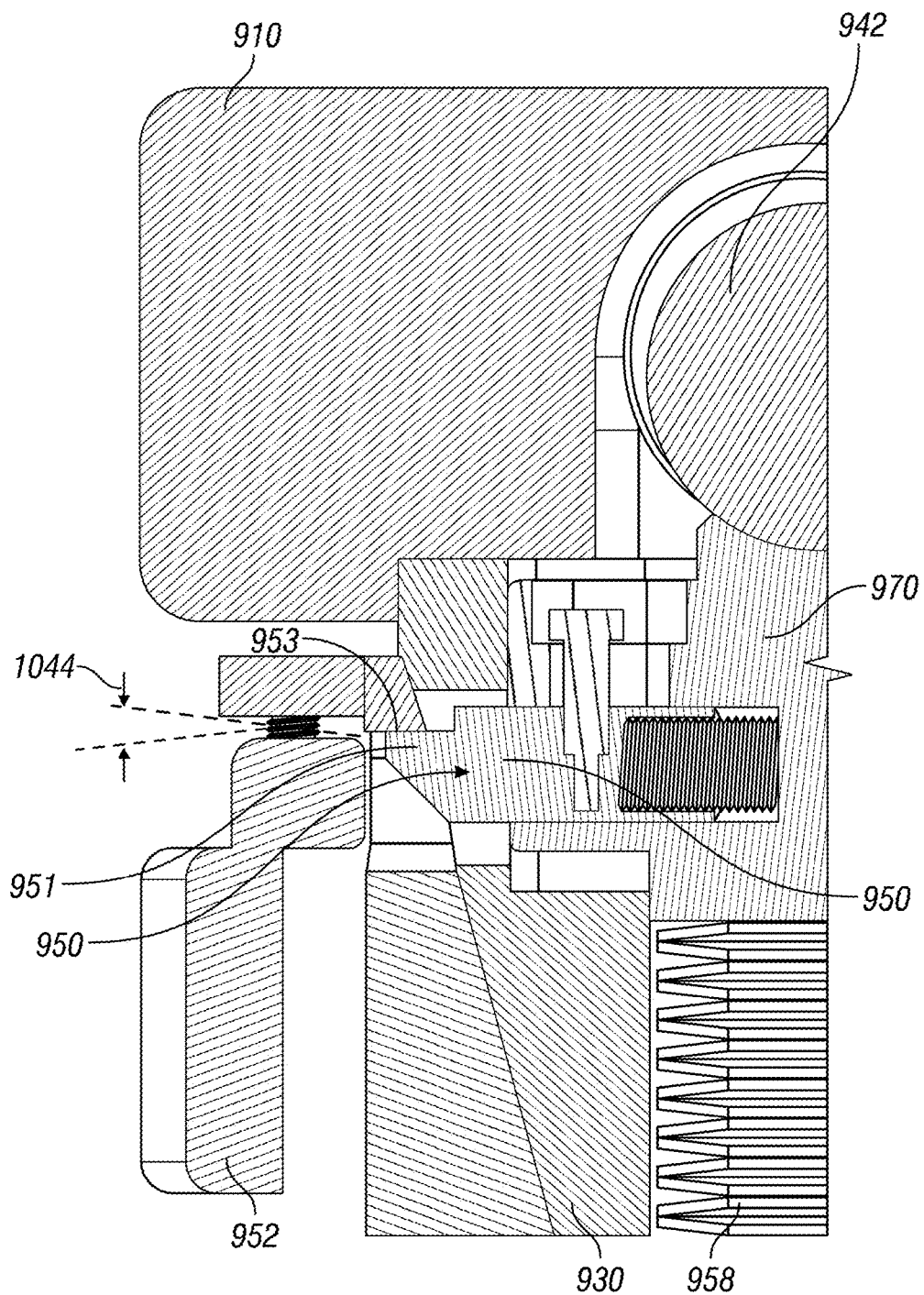

FIGS. 9H and 9M shows a first surface 951 and a second surface 953 of the catch 950. The first surface 951 may be an angled, flat surface having an angled similar to that of the taper angle of the cone 930. The first surface 951 may be configured to permit the catch 950 to slide easily over a surface of a conical hole 912. As the first surface 951 translates through the conical hole 912 of the second portion 920, the catch 950 is recessed into the cone 930. The second surface 953 may a tapered portion configured to hold the first portion 910 against the second portion 920. The second surface 953 of the catch 950 may include an anti-release angle 1044 configured to prevent the catch 950 from decoupling from the second portion 920 when the catch 950 is in a protruding configuration. The catches 950 may be configured to be biased towards the protruding configuration.

In some embodiments, the catches 950 may include a camming surface configured to contact a corresponding surface such that by wedging the catches outward rather than being pulled back, the first portion 910 and second portion 920 may be secured and locked together. For example, the camming surface may include an angle surface, a ball and socket surface, and/or the like.

FIG. 9H illustrates a set of Belleville washers 958 coupled to the catches 950 and shuttle 970. The Belleville washers 958 may be configured to apply a holding force to the catch 950. In some embodiments, the Belleville washers 958 may apply between about 130 lb force and about 230 lb force. The Belleville washers 958 may be configured to vary a force of the lock (e.g., handle 940, cam 942, and shuttle 970). In some embodiments, a precompression force of the Belleville washers 958 may be adjusted using an auxiliary input.

The handle 940 coupled to the cam 942 is illustrated in FIGS. 9H and 9M. The cam 942 is configured to rotate in response to rotation of the handle 940 between unlocked and locked positions. Rotation of the cam 942 towards a locked position applies contact forces to the shuttle 970 disposed within the cone 930. As the handle 940 rotates through its arc, the cam 942 applies force against the shuttle 970 of the first portion 910 to bring the first portion 910 and second portion 920 together and securely lock the first portion 910 to the second portion 920 with high rigidity. When the handle 940 is in the locked position, the first portion 910 and second portion 920 are securely engaged and locked to each other. In some embodiments, the first portion may include a motorized locking mechanism as described herein, in place of the handle 940 and cam 942. In some embodiments, the cam 942 may be rotated indirectly through, for example, a set of right angle gears or rotational motion about an axis separate from the cam 942 axis.

To release the second portion 920 from the initial lock state (where the handle 940 is in the unlocked position), the switch 952 may be actuated by being pressed in, thereby pressing in the catches 950 in a second configuration and allowing a user to translate the second portion 920 away from the first portion 910. FIG. 9I-FIG. 9L illustrates front, side, top, and perspective views, respectively, of the switches 952. A switch 952 may include a release point 956 configured to make contact with and push a corresponding axial switch 950 into the recessed second configuration. The switch 952 may rotate about a hinge 1054 when actuated. In some embodiments, the switches 952 may be spaced apart by about 3.5 inches. This allows a user to engage both switches 952 simultaneously using one hand wrapped around second portion 920, thereby naturally encouraging the placement of the user's hand in a position to support the arm (and reduce the likelihood of a dropped arm) when the second portion 920 is decoupled form the first portion 910. Each switch 952 may include a torsion spring configured to bias the switch 952 to an initial, reset position.

In some embodiments, the first portion 910 and the second portion 920 may each include an electrical interface 938 to provide a power and/or data connection between the first portion 910 and the second portion 920. The electrical interface may include one or more of a spring contact pin, wiping contacts, a fiber optic interface, transformers, or any other power and/or data connector. In some embodiments, the electrical interface of the first portion 910 may be disposed on the tapered surface of the cone 930 or on the base flange of the first portion 910 that supports the cone 930. In some embodiments, one or more of the catches 950 may include an electrical interface since the catches 950 contact the second portion 920.

In some embodiments, the coupler 900 may include one or more connection sensors 936, as described herein, and configured to detect coupling and decoupling between the first portion 910 and the second portion 920. For example, connection sensors may be configured to detect one or more of an amount of force the catches 950 are holding, a location of the catches 950 (e.g., amount that the catches have moved), and a contact state between the cone 930 and the second portion 920.

In some embodiments, one or more of the first portion 910 and second portion 920 may include a dampener configured to vibrationally isolate the first portion 910 from the second portion 920.

Figure 10:
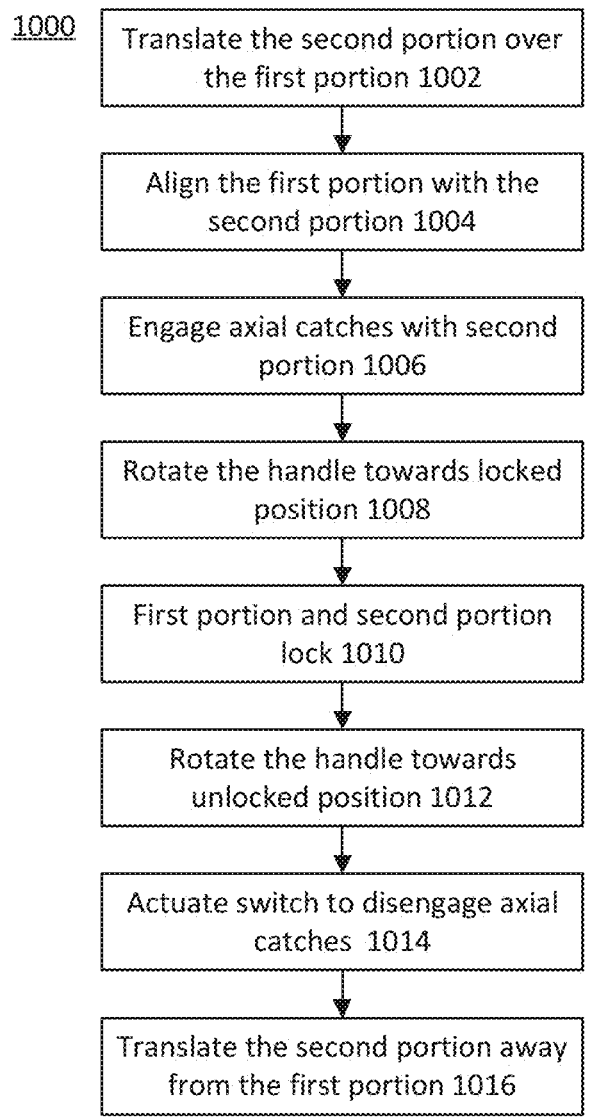
FIG. 10 is a flowchart of a method of attaching a robotic arm to a surgical table, according to an embodiment.

FIG. 10 is a flowchart of a method 1000 of coupling a robotic arm to a surgical table, such as by using any of the couplers described herein. The method 1000 includes translating at 1002 a second portion (e.g., robotic arm base portion) of a coupler over a first portion of the coupler (e.g., mounting portion of a surgical table top) (FIG. 9E). A conical taper of the first portion may provide initial alignment. The second portion at 1004 is further aligned with the first portion as the second portion is translated over a cone of the first portion by aligning corresponding alignment elements on each of the first and second portions. The locking mechanism of the first portion (e.g., catches) will not engage with the second portion if the alignment element(s) of the first portion are not aligned with the second portion. The catches are engaged with the second portion at 1006 (FIG. 9F). This initial coupling of the catches to the second portion is self-locking in that the coupling will not become disengaged (e.g., released) without user input (e.g., user actuation of a switch). At this point, the first portion and second portion are coupled in an initial engagement state such that the second portion is unable to fall away from the first portion if the second portion was unsupported by a user.

While in the initial engagement state, a handle may be rotated at 1008 to rotate a two position cam of the first portion to apply contact forces to a shuttle disposed within the cone. As the handle rotates through its arc, the cam applies force against the shuttle of the first portion to bring the first portion and second portion together and securely lock the first portion to the second portion with high rigidity. In some embodiments, the handle may rotate about 90 degrees from an unlocked position to a locked position. The first portion and second portion are locked at 1010.

To disengage the first portion from the second portion, the handle must be rotated to an unlock position before a catch switch is actuated. Accidental decoupling is reduced by required both locks to be decoupled by a user. The handle may be rotated at 1012 towards an unlocked position to rotate the cam and decouple it from the shuttle. Rotation of the handle to the unlocked position does not fully decouple the first portion and second portion, and permits the user to support the mass of a robotic arm coupled to the second portion. Actuation of one or more switches at 1014 recesses the catches into the cone and allows the second portion to translate at 1016 out and away from the cone of the first portion.

Radial Clamping Arm Based Connection

Figure 11A:
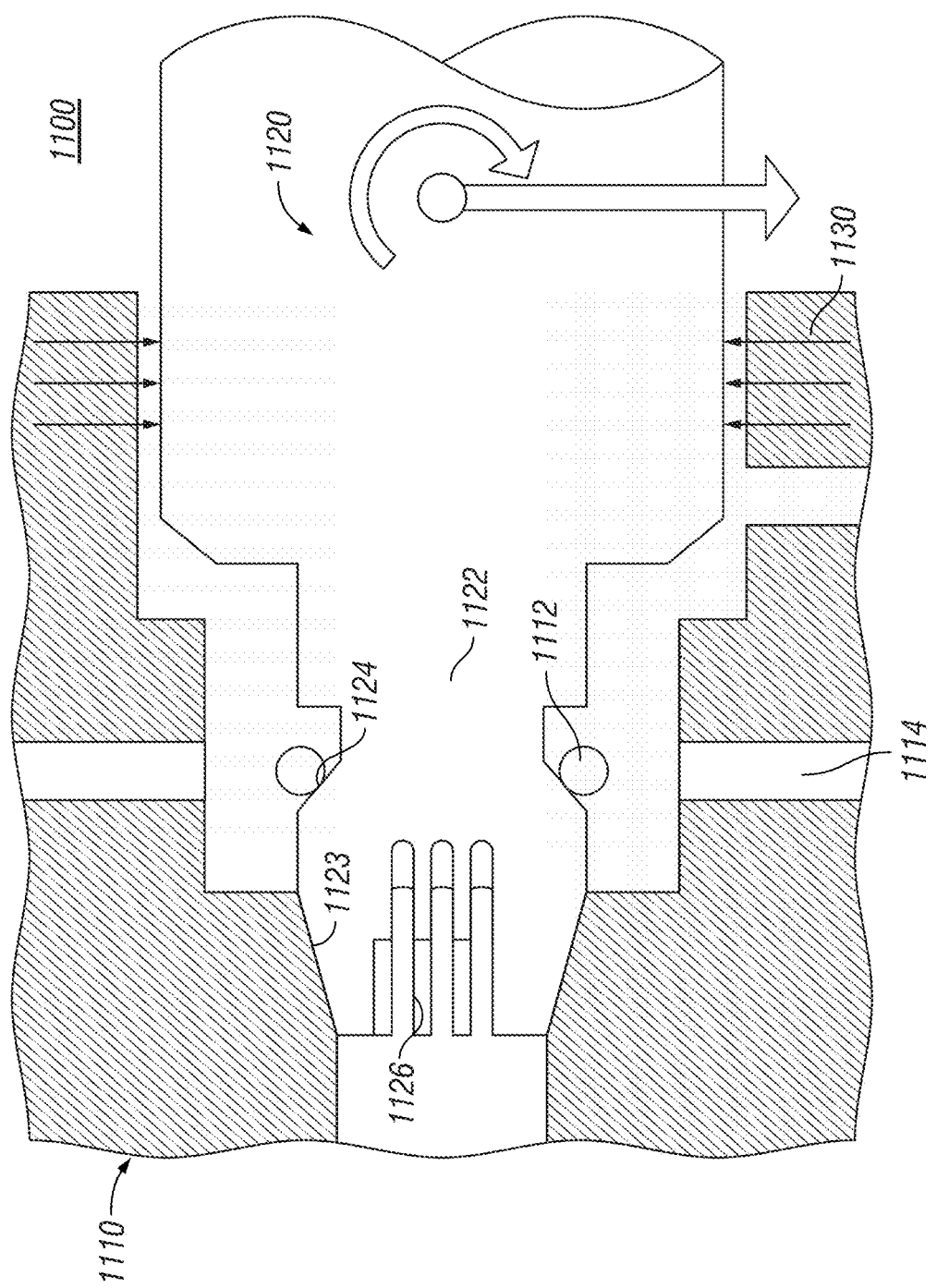
FIGS. 11A-11I illustrate a coupler, according to an embodiment.
Figure 11C:
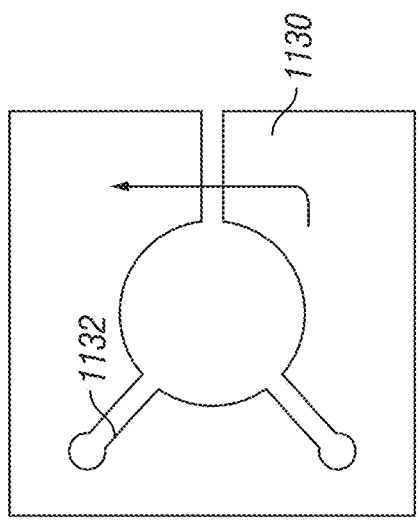
Figure 11D:
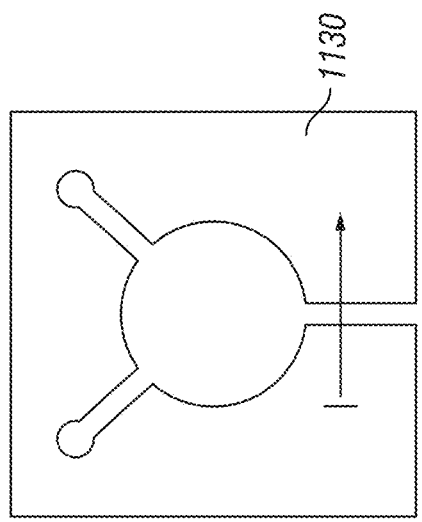
Figure 11B:
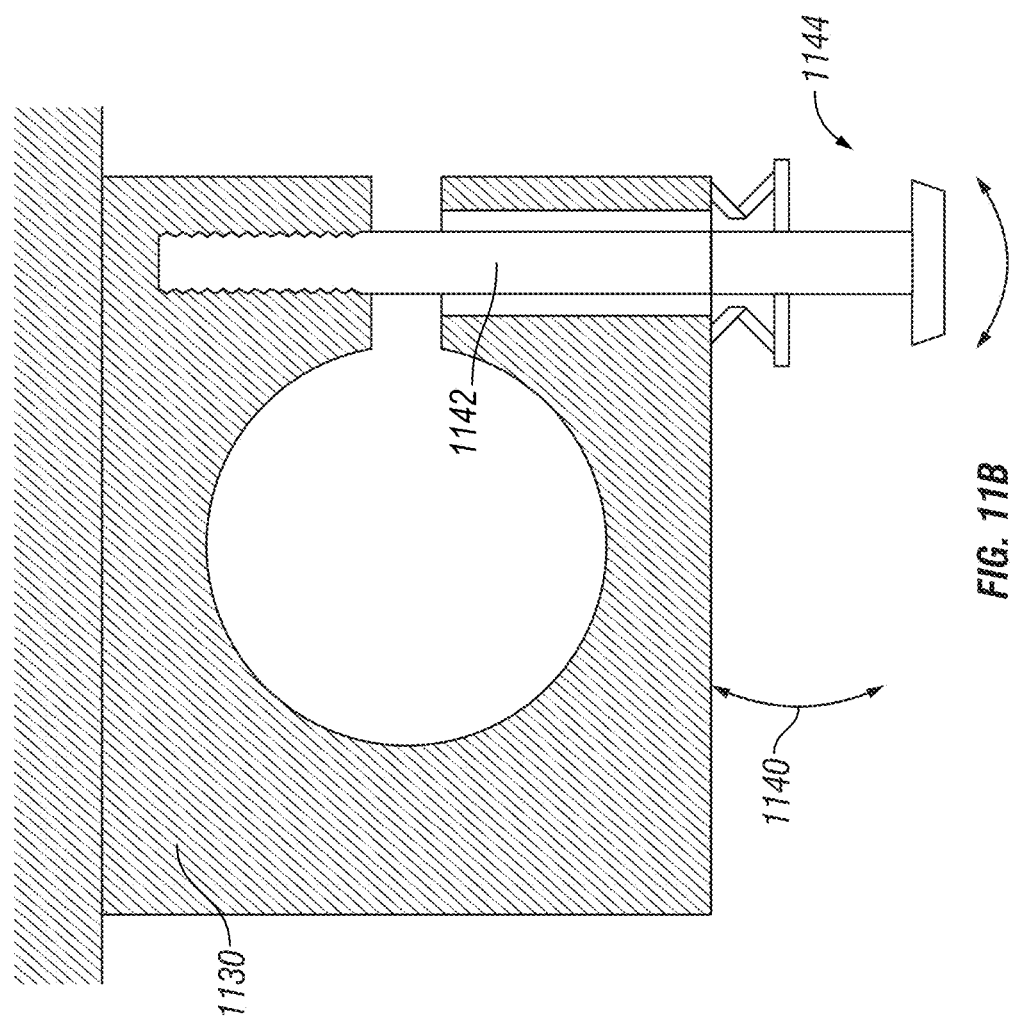
Figure 11F:
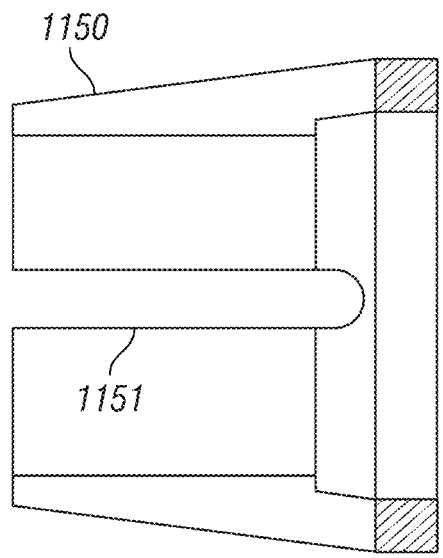
Figure 11G:
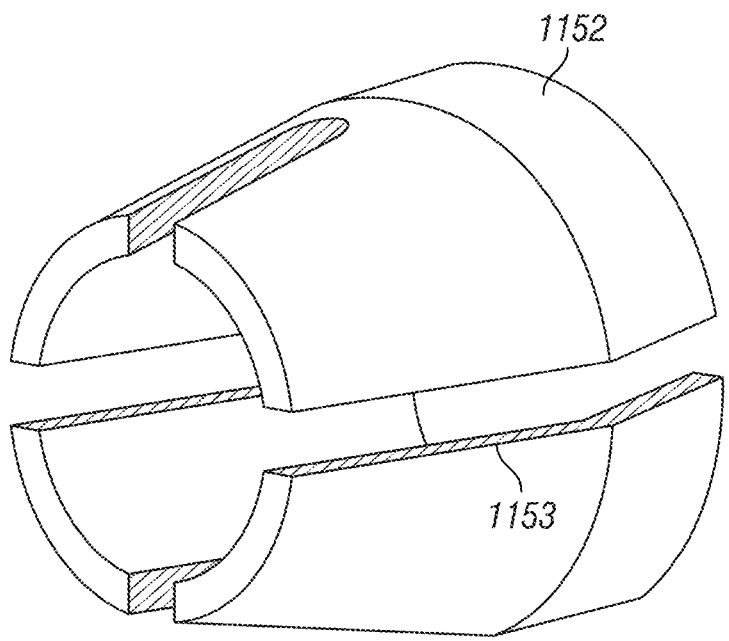
Figure 11H:
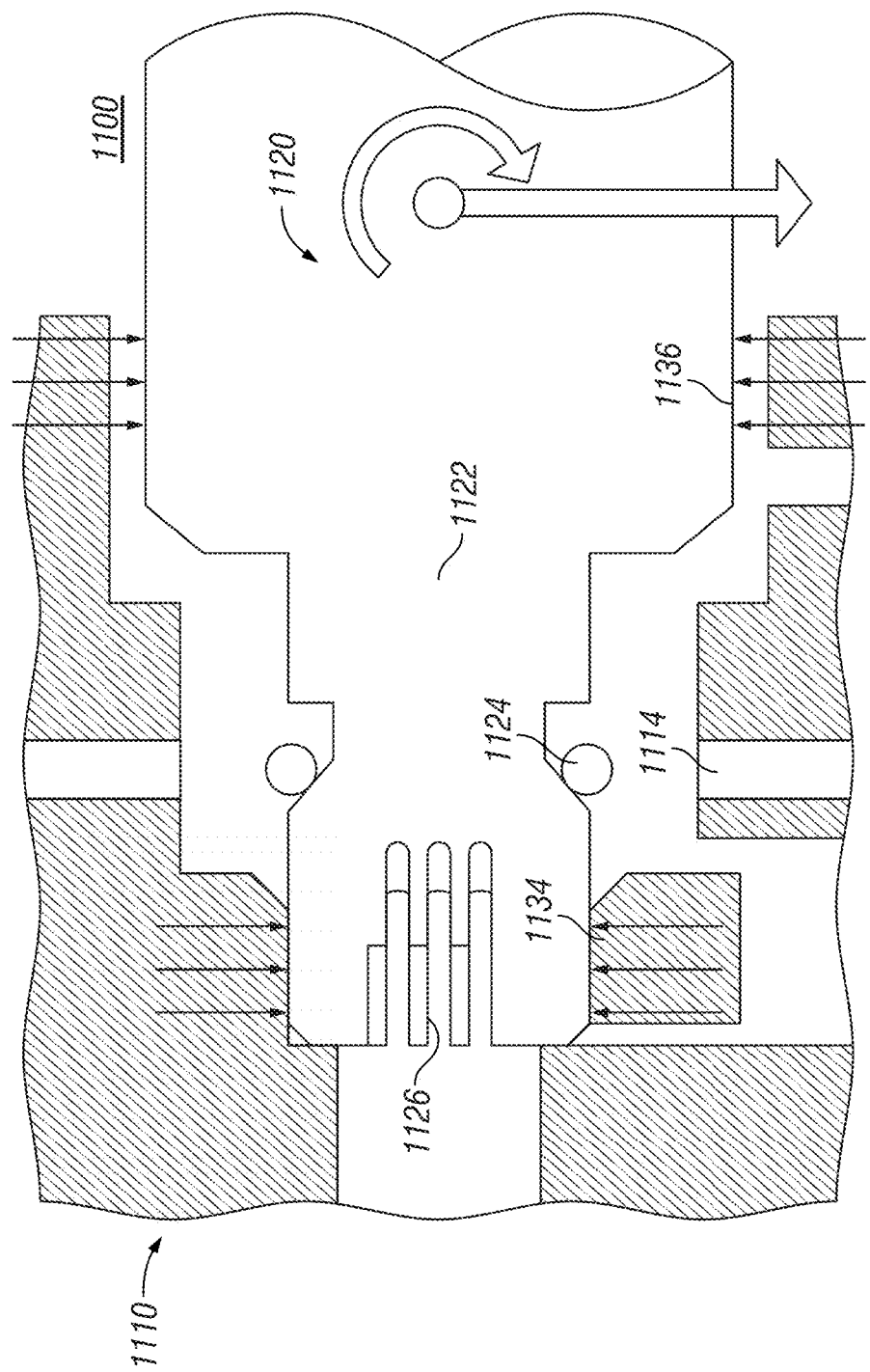
Figure 11L:
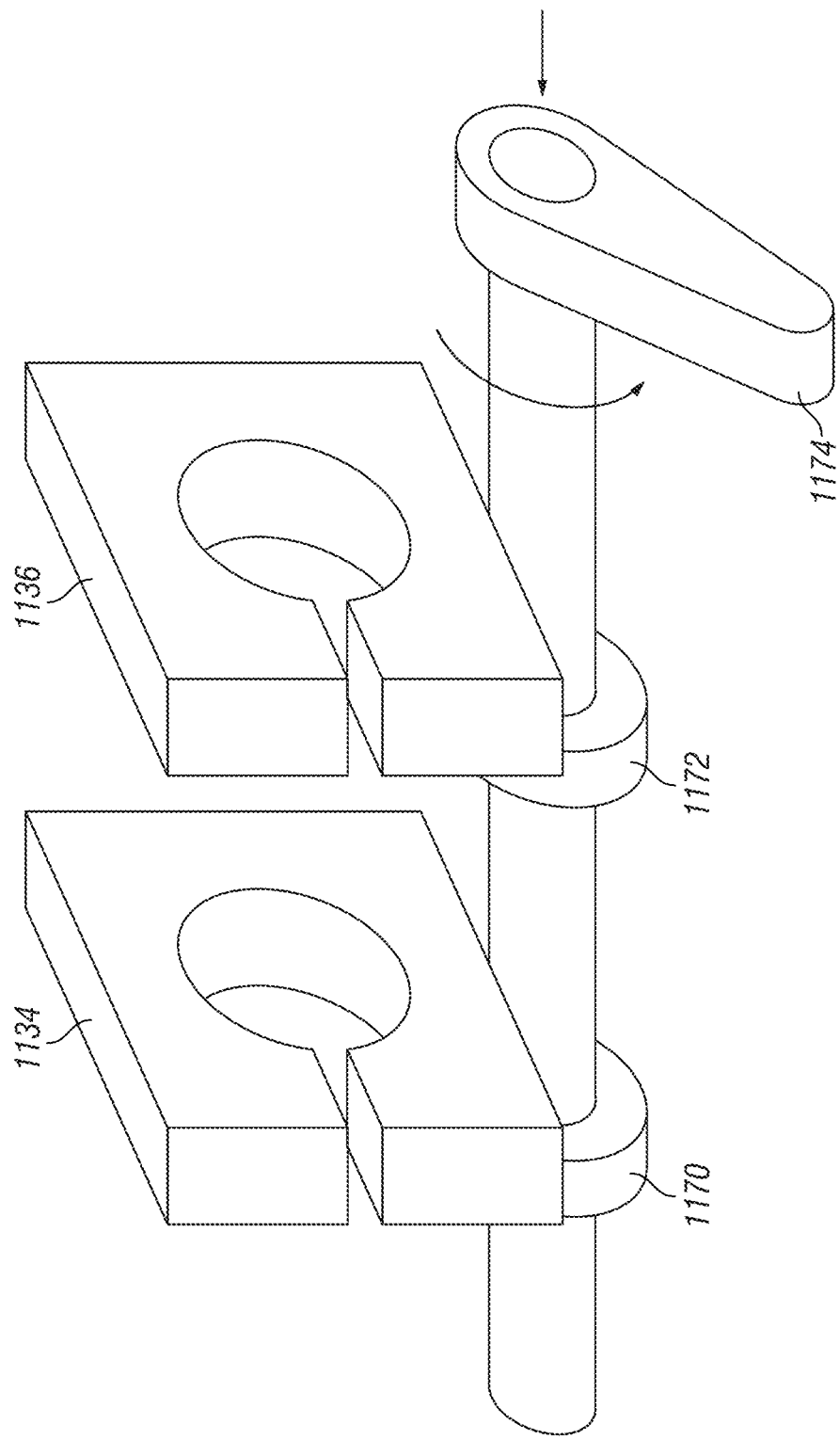
Figure 13A:
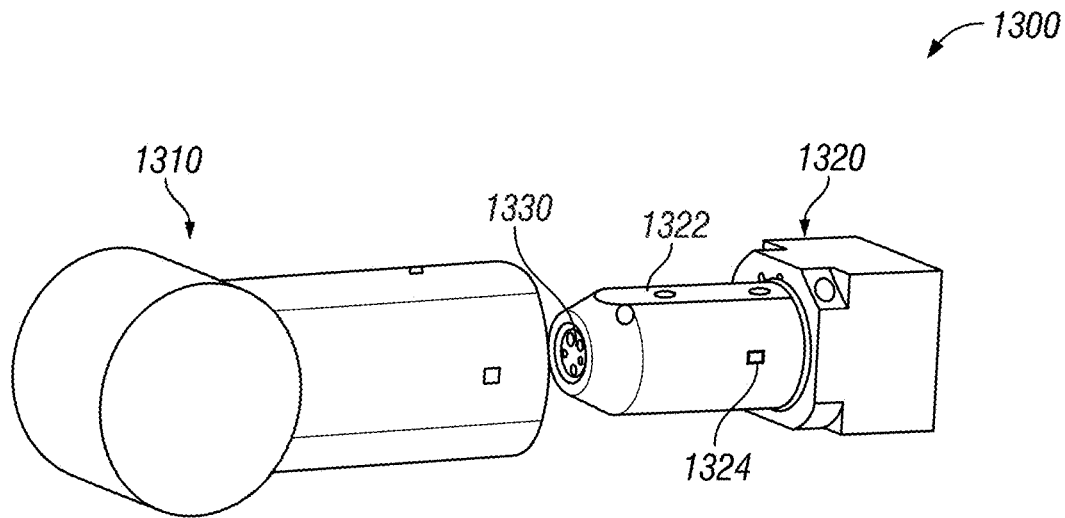
FIGS. 13A-13D are perspective views of a coupler, according to an embodiment.
Figure 13B:
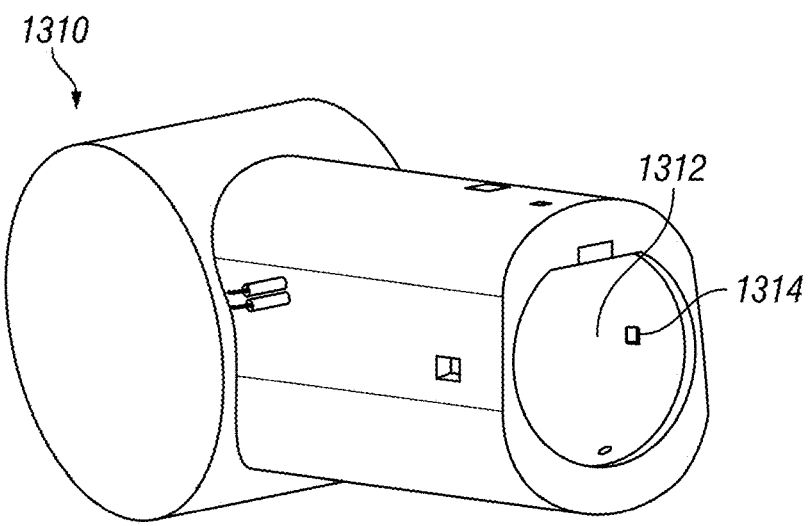
Figure 13C:
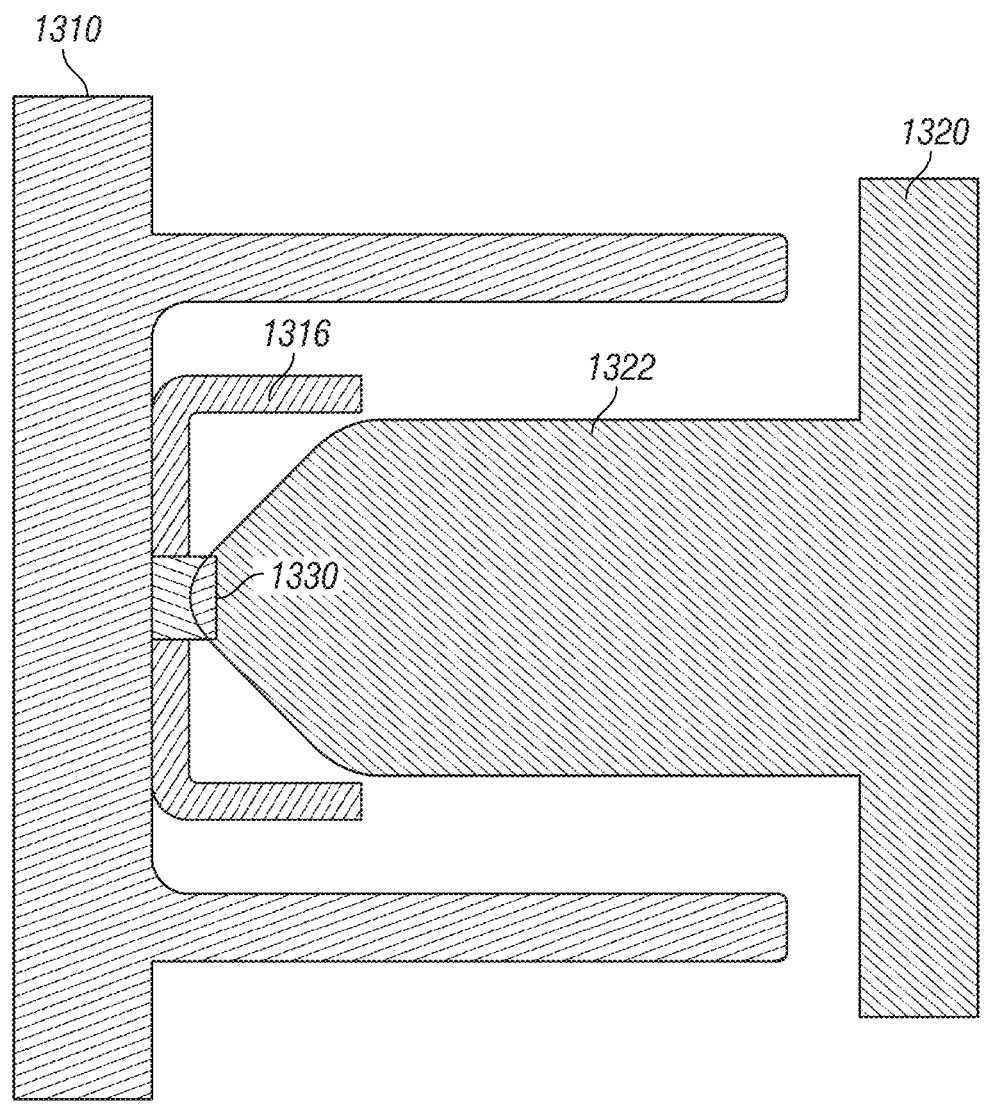
Figure 13D:
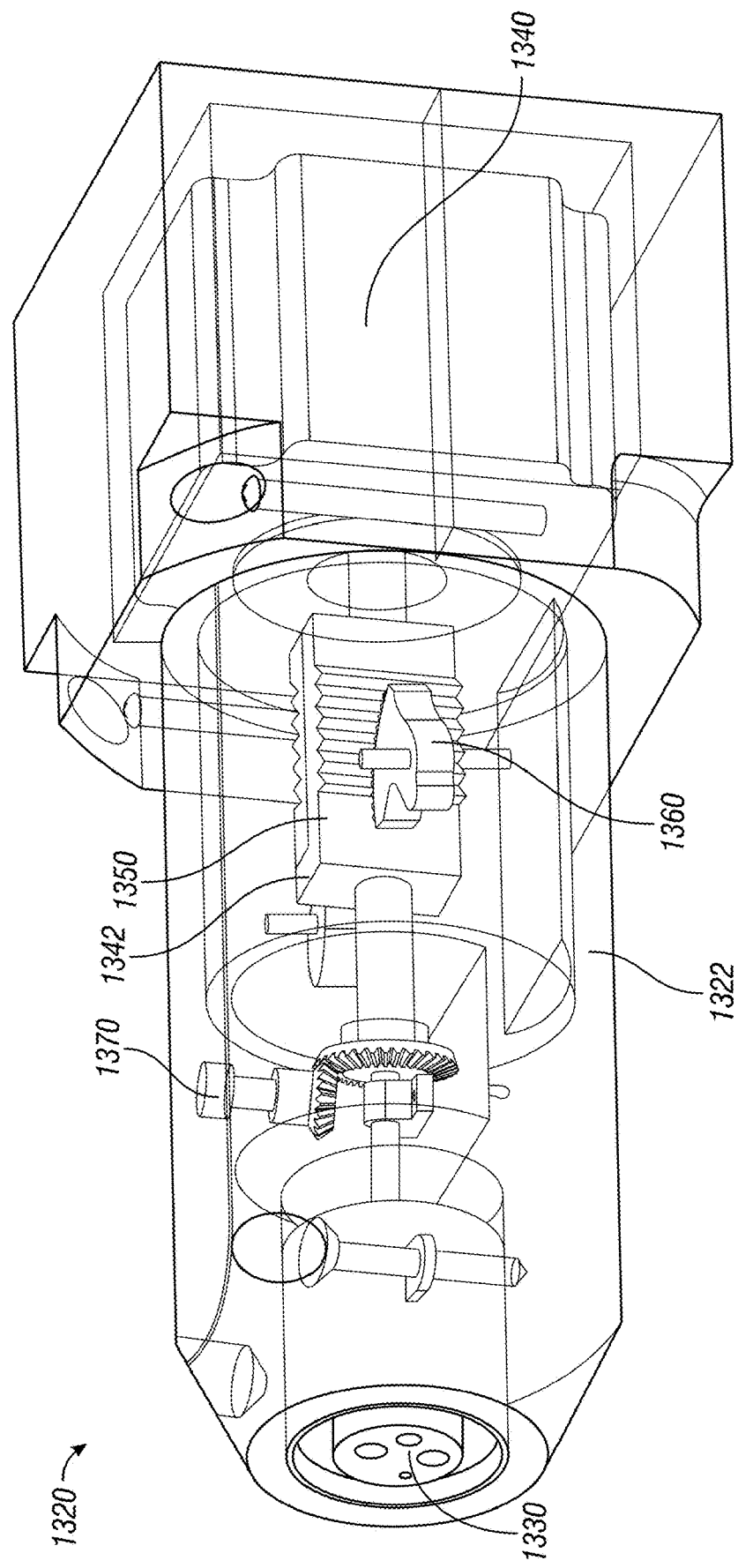

FIGS. 11A, 11E, and 11H are cross-sectional side views of embodiments of a coupler 1100 including a first portion 1110 and a second portion 1120. Coupling of the first portion 1110 and second portion 1120 forms a secure mating connection where six degrees of freedom are constrained. The first and second portion may each include an electrical interface 1126 to provide power and data through the coupler 1100. The first portion 1110 includes a ball bearing 1112 coupled to a spring 1114 configured to couple the first portion 1110 to the second portion 1120. In some embodiments, a positive lock may be further coupled to spring 1114 to prevent spring back. The second portion 1120 includes a post 1122 that may be translated along a Y-axis to mate with the first portion 1110. The second portion 1120 may include a first surface 1123 and a second surface 1124. The second surface 1124 may have a steeper angle relative to the first surface 1123. A radial clamp 1130 may be disposed around the second portion 1120. Coupling of the post 1122 to the first portion 1110 may constrain translation along the Y-axis.

FIG. 11A illustrates the first portion 1110 aligned and having an initial engagement with the second portion 1120. The post 1122 of the second portion 1120 may include the first surface 1123 (e.g., lead in taper) configured to permit misalignment during translation and sliding of the post 1122 into the first portion 1110. The post 1122 may further include a second surface 1124 (e.g., angled face) configured to press against the ball bearings 1124. The first surface 1123 and second surface 1124 experience Hertzian stresses based on the curvature of the surfaces. The curvature and material properties, along with the ball bearing 1124 diameter and material may be configured to generate contact conditions that do not deteriorate the surfaces.

The clamp 1130 may be tightened to lock the first portion 1110 to the second portion 1120. FIGS. 11B-11D are front cross-sectional view of the radial clamp 1130 coupled to an actuator 1140. The actuator 1140 may include a screw 1142 and handle 1144. A user actuating the handle 1144 may turn the screw 1142 to vary a radial compression force of the clamp 1130 on the second portion 1120. The actuator 1140 may be pivoted or rotated. In some embodiments, the actuator 1140 may be rotated a quarter turn to achieve a desired radial compression of clamp 1130. The clamp 1130 may also include one or more reliefs 1132 to distribute compression forces. The clamp compresses within a predetermined range and serve as a locking mechanism to apply forces to both the first portion 1110 and second portion 1120 to securely lock them together and form a coupling between the first portion 1110 and the second portion 1120.

FIG. 11E illustrates a coupler 1100 including a first collet 1150 and a second collet 1152. The first collet 1150 may be configured to couple to an end of the second portion 1120 between the first portion 1110 and the second portion 1120. The second collet 1152 may be configured to couple to a base portion of the second portion 1120 between the first portion 1110 and the second portion 1120. The first collet 1150 and second collet 1152 are both coupled to a toggle 1160 having a handle 1162 for a user to translate along a Y-axis. The outer and inner surfaces of the collets may match an angle of respective first and second portions such that the collets may translate and compress between the first and second portions. In some embodiments, the collets may be coupled to a set of Belleville washers to provide a predetermined compression force. The first collet 1150 and second collet 1152 may each include one or more slits 1151, 1153 (see FIGS. 11F-11G) such that translation of the toggle 1160 towards the first portion 1110 will compress the collets and secure the coupling between the first and second portions. The collets translate and compress within a predetermined range and serve as a locking mechanism to apply forces to both the first portion 1110 and second portion 1120 to securely lock them together and form a coupling between the first portion 1110 and the second portion 1120. In some embodiments, compression of the collets at a predetermined force forms an electrical interface connection.

FIG. 11H illustrates a coupler 1100 including a first clamp 1134 and a second clamp 1136. The first clamp 1134 may be configured to couple to and vary a radial compression force to an end of the second portion 1120. The second clamp 1136 may be configured to couple and vary a radial compression force. In some embodiments, the first clamp 1134 and second clamp 1136 may be coupled to a respective first cam 1170 and second cam 1172, as shown in FIG. 11I. Each of the cams may be coupled to a handle and actuated together to vary a radial compression force on the second portion 1120. The first cam 1170 and second cam 1172 may have different profiles and may be actuated using rotary or linear motion. In addition, cams 1170, 1172 may allow for different timing, different compression and/or linear motion and clamping of the clamps 1134, 1136. Each of the clamps compresses within a predetermined range and serve as a locking mechanism to apply forces to both the first portion 1110 and second portion 1120 to securely lock them together and form a coupling between the first portion 1110 and the second portion 1120. In some embodiments, compression of the radial clamp at a predetermined force forms an electrical interface connection.

FIG. 12 is a flowchart of a method 1200 of coupling a robotic arm to a surgical table, such as by using any of the couplers described herein. The method 1200 includes translating at 1202 a second portion (e.g., robotic arm base portion) of a coupler into a first portion of the coupler (e.g., mounting portion of a surgical table top). A post of the second portion may begin to align at 1204 as the post moves into the first portion. The locking mechanism of the first portion (e.g., radial clamp, handle, actuator, knob) will not engage if the alignment element(s) of the second portion are not aligned with the first portion. When the post is in an initial engagement state against a set of ball bearings, the handle may be rotated at 1206 to compress the radial clamp. The pressing force of the radial clamp locks at 1208 the first and second portions together. In order to decouple the coupler 1200, a user may rotate the handle at 1210 towards the unlocked position. This decompresses the radial clamp, thereby releasing the force between the ball bearings and the housing of the second portion. With the lock disengaged, the second portion may be fully decoupled from the first portion by translating the second portion out of the first portion at 1212.

Other Arm Base Connections

FIGS. 13A-13D are perspective views of embodiments of a coupler 1300 including a first portion 1310 and a second portion 1320. Coupling of the first portion 1310 and second portion 1320 forms a secure mating connection where six degrees of freedom are constrained. The first and second portion may each include an electrical interface to provide power and data through the coupler 1300. The post hole 1312 may include a first electrical connector 1316 shown in FIG. 13C configured to couple to a second electrical connector 1330 shown in FIG. 13A-13C.

The second portion 1320 includes a post 1322 that may be translated along a Y-axis to mate with the first portion 1310. The post 1322 may include a set of catches 1324 biased to protrude from the post 1322 in the first configuration and be recessed into the post 1322 in the second configuration. The first portion 1320 includes a post hole 1312 and a set of catch holes 1314 corresponding to the set of catches 1324 of the second portion 1320. The catches 1324 may be driven by a lead screw 1342 coupled to a motor 1340. As the lead screw 1342 is translated along a Y-axis, a linear rack 1350 coupled to the lead screw 1342 translates along a Y-axis and rotates a catch 1360 between the first and second configurations. This motorized locking mechanism may ensure a secure coupling between the first portion 1310 and second portion 1320. The second portion 1320 may include an access port 1370 (see FIG. 13D) for a user to manually insert a tool (e.g., Allen wrench) to manually backdrive the linear rack 1350 and enable decoupling of the robotic arm from the surgical table. The motor 1340 may be, for example, a brushless DC motor.

Figure 14A:
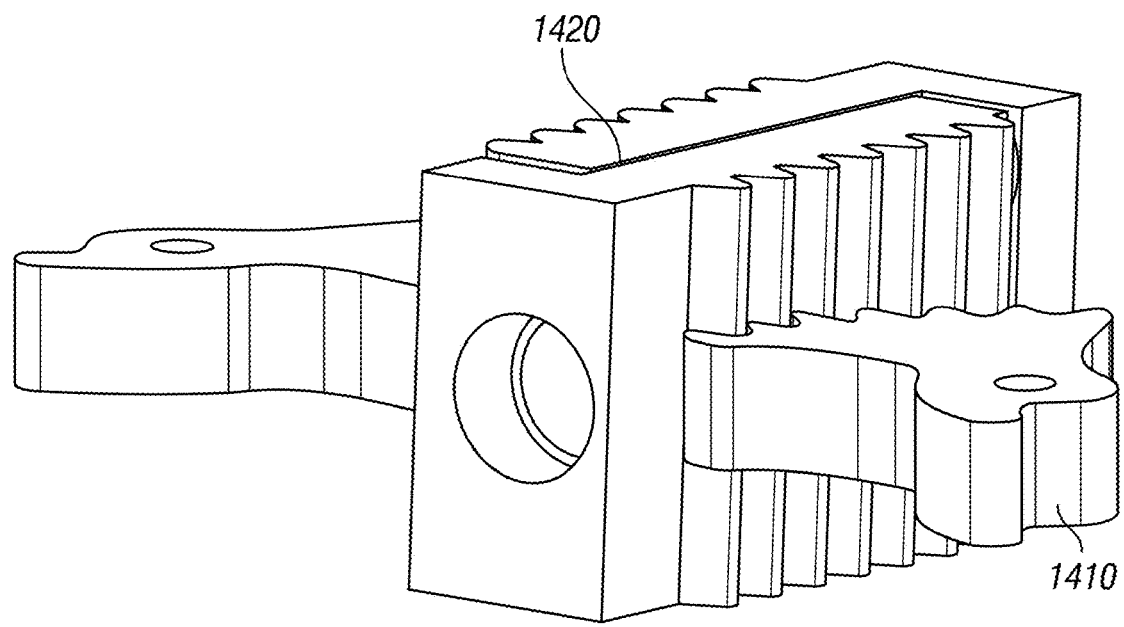
FIGS. 14A-14E are exterior perspective views of a linear rack and cam, according to an embodiment.
Figure 14B:
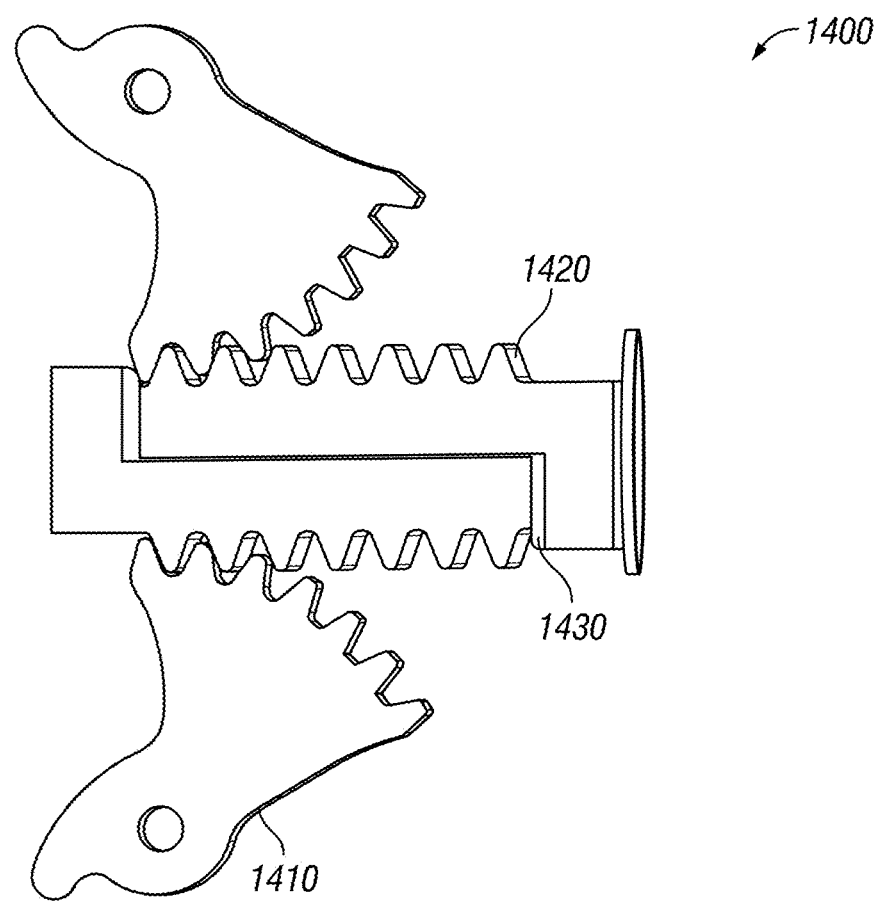
Figure 14C:
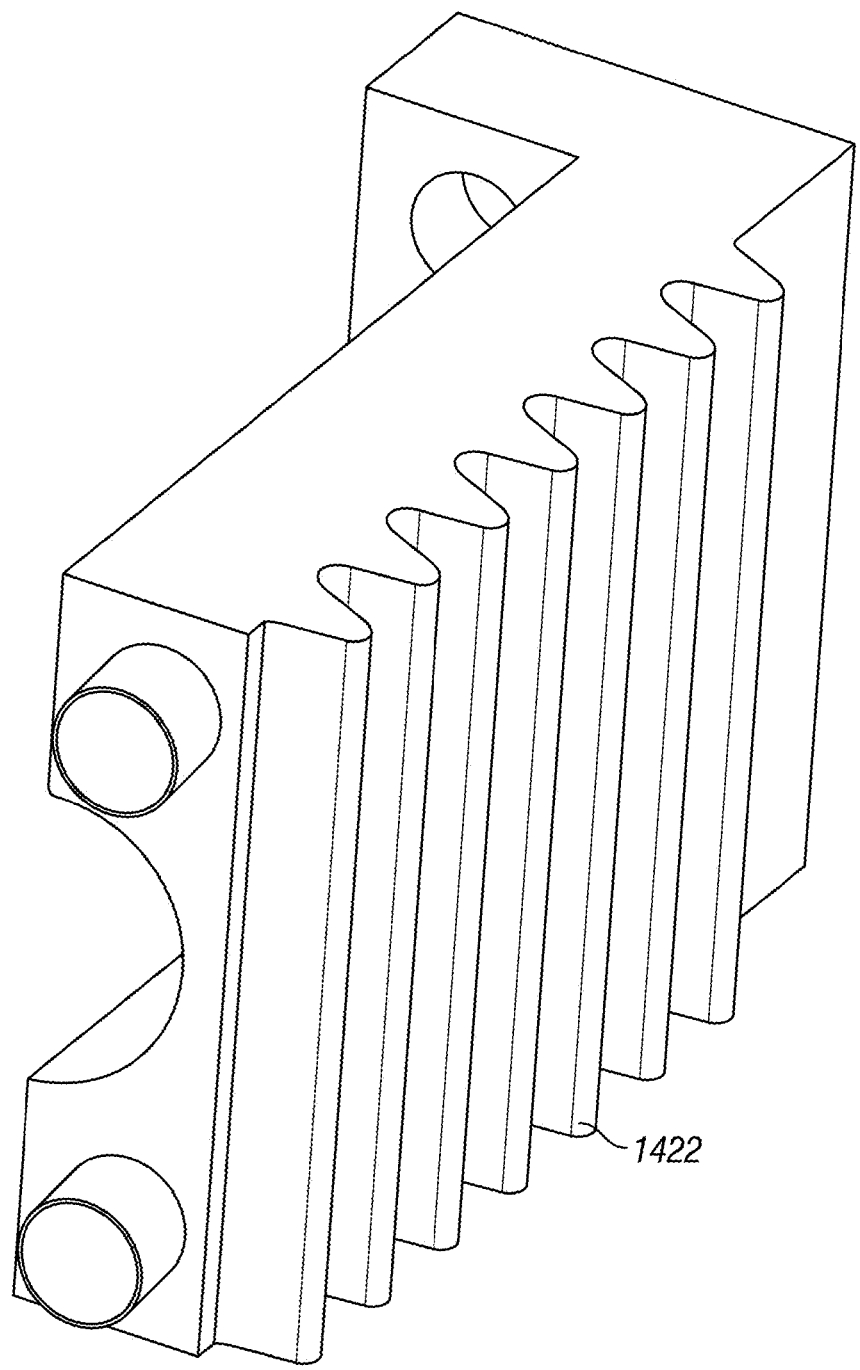
Figure 14D:
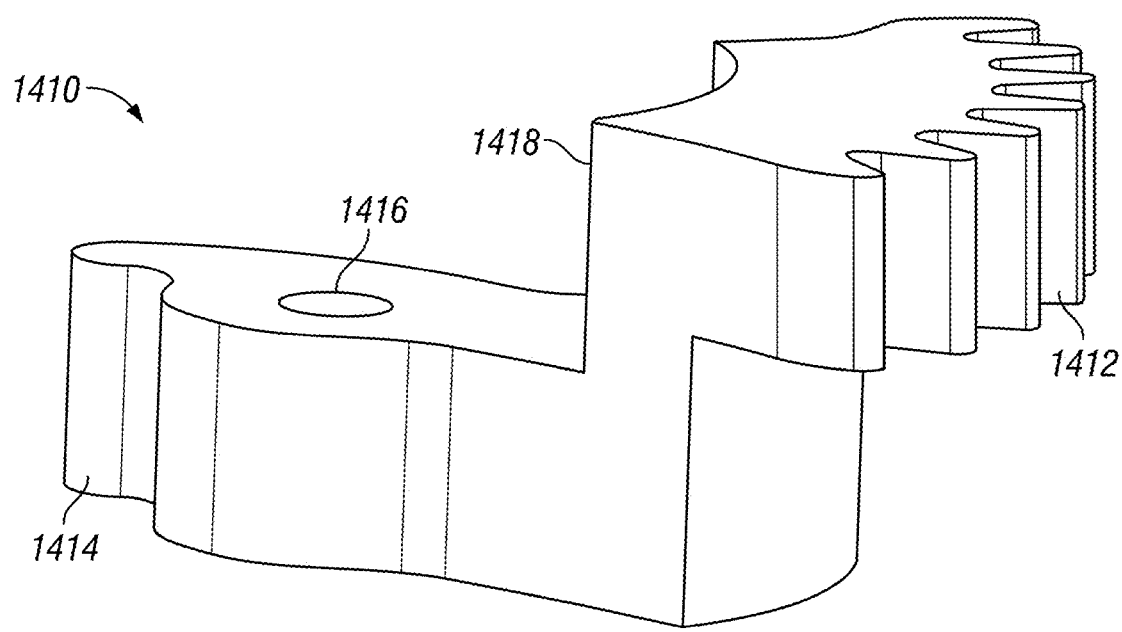
Figure 14E:
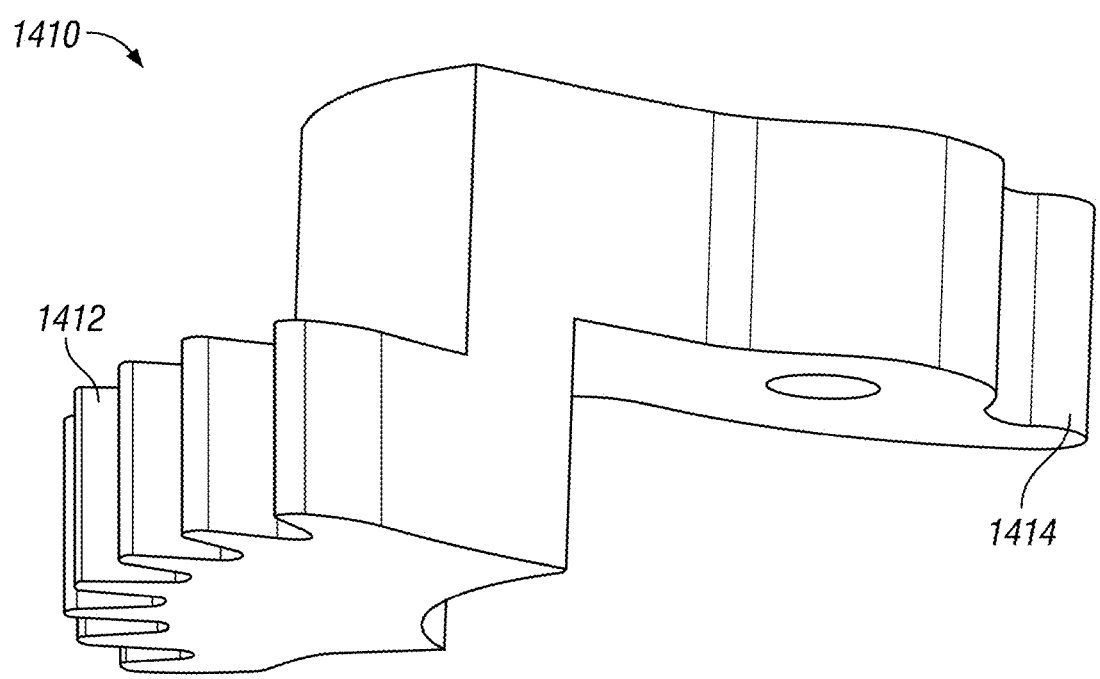

FIGS. 14A-14E are exterior views of a linear rack assembly 1400 including a linear rack 1420 and catch 1410. The linear rack 1420 may be dual sided in that the rack 1422 of one side (see FIG. 14C) is interchangeable with that of the other side. In other words, the rack 1422 of FIG. 14C may be flipped and mated to be symmetric. The linear rack 1420 may include one or more Belleville washers to increase compliance for the catches 1410 (e.g., rotating cam claws). A post may be provided at one end of each rack to allow each rack to press together. A washer 1430 may be disposed between the mating surfaces of the racks 1422 to add compliance and spring resistance. The catch 1410 may include a spur gear 1412 and a cam claw 1414 separated in height by an offset 1418 as illustrated by FIGS. 14D-14E. The catch 1410 may rotate about an axis 1416. The cam claw 1414 may mate with a corresponding surface of the first portion as the catch rotates.

Figure 15A:
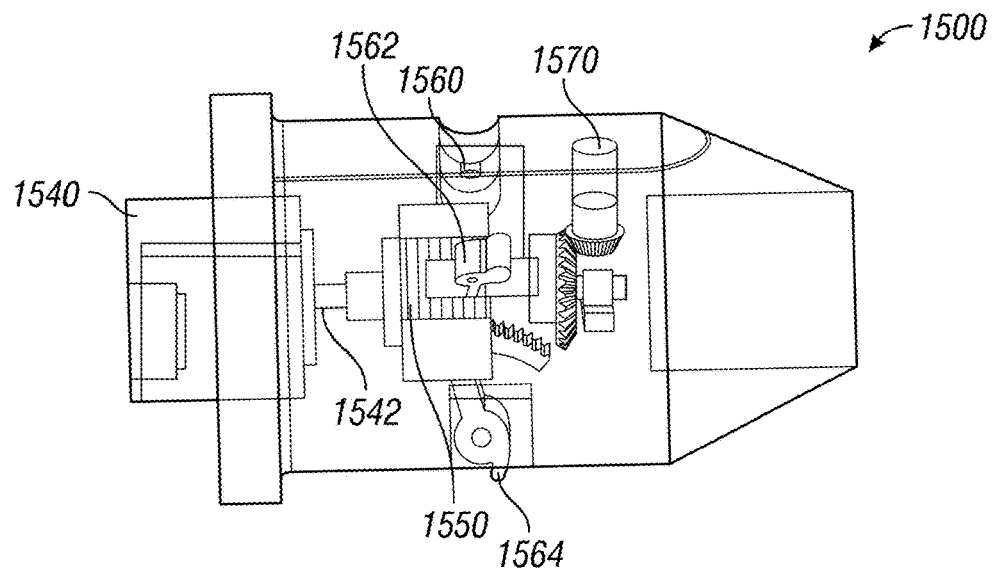
FIG. 15A-FIG. 15C are internal perspective views of a coupler, according to an embodiment.
Figure 15B:
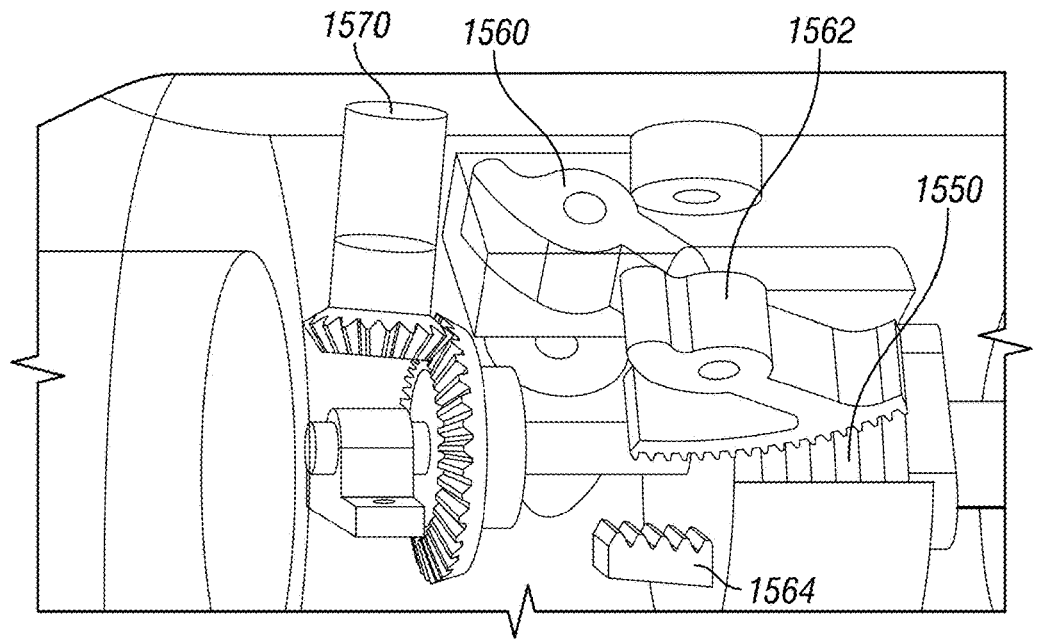
Figure 15C:
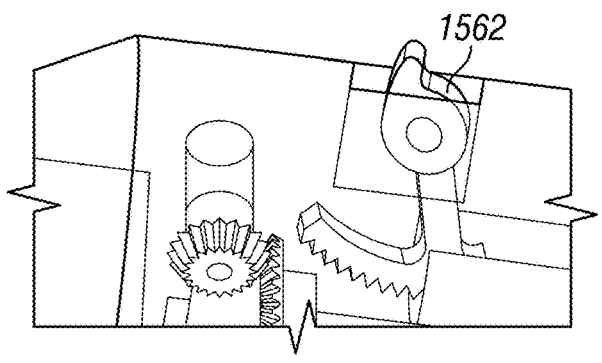

FIGS. 15A-15C are internal perspective views of a coupler 1500, according to an embodiment. In some embodiments, the coupler 1500 may include a set of three catches biased to protrude from the surface of a housing in the first configuration and be recessed into the housing in the second configuration. The catches 1560, 1562, 1564 may be driven by a lead screw 1542 coupled to a motor 1540. As the lead screw 1542 is translated along a Y-axis, a linear rack 1550 coupled to the lead screw 1542 translates along a Y-axis and rotates the catch 1560, 1562, 1564 between the first and second configurations. The coupler 1500 may include an access port 1570 for a user to manually insert a tool (e.g., Allen wrench) to manually backdrive the linear rack 1550 and enable decoupling of the robotic arm from the surgical table. The motor 1540 may be, for example, a brushless DC motor.

Figure 16A:
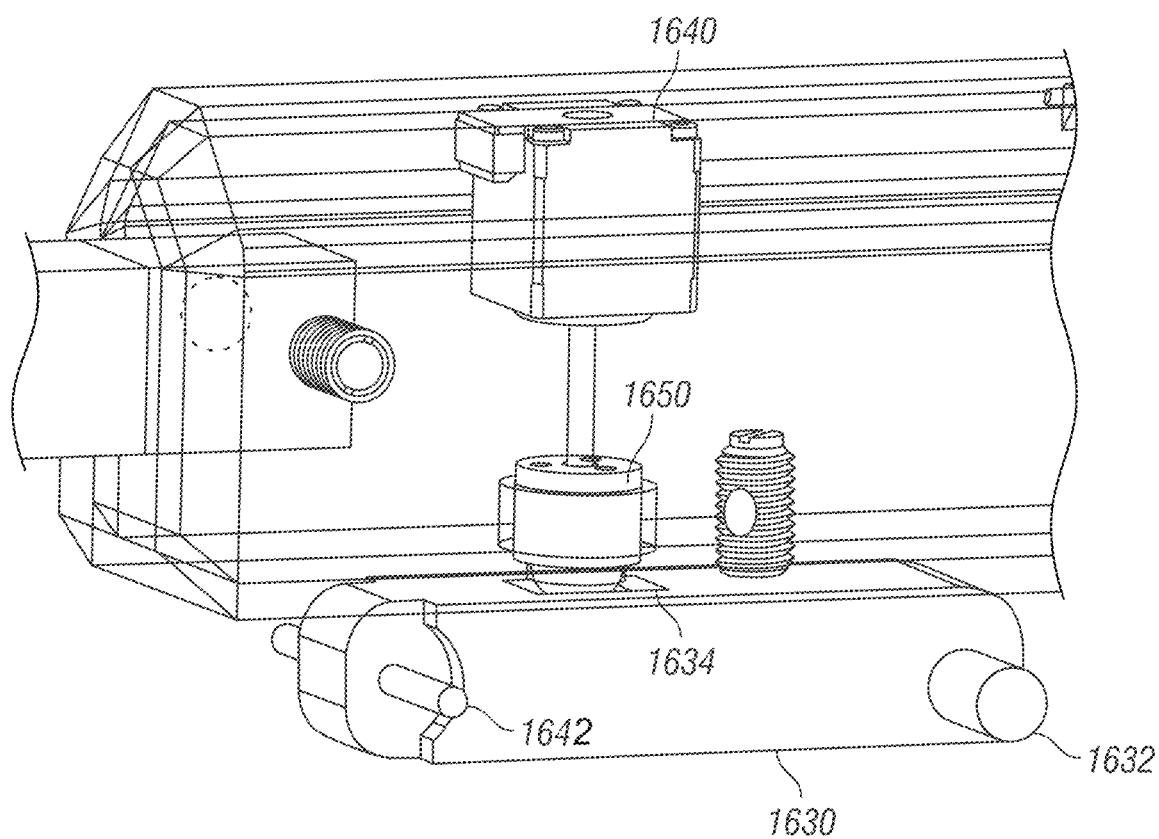
FIG. 16A-FIG. 16B are internal and external views of a coupler, according to an embodiment.
Figure 16B:
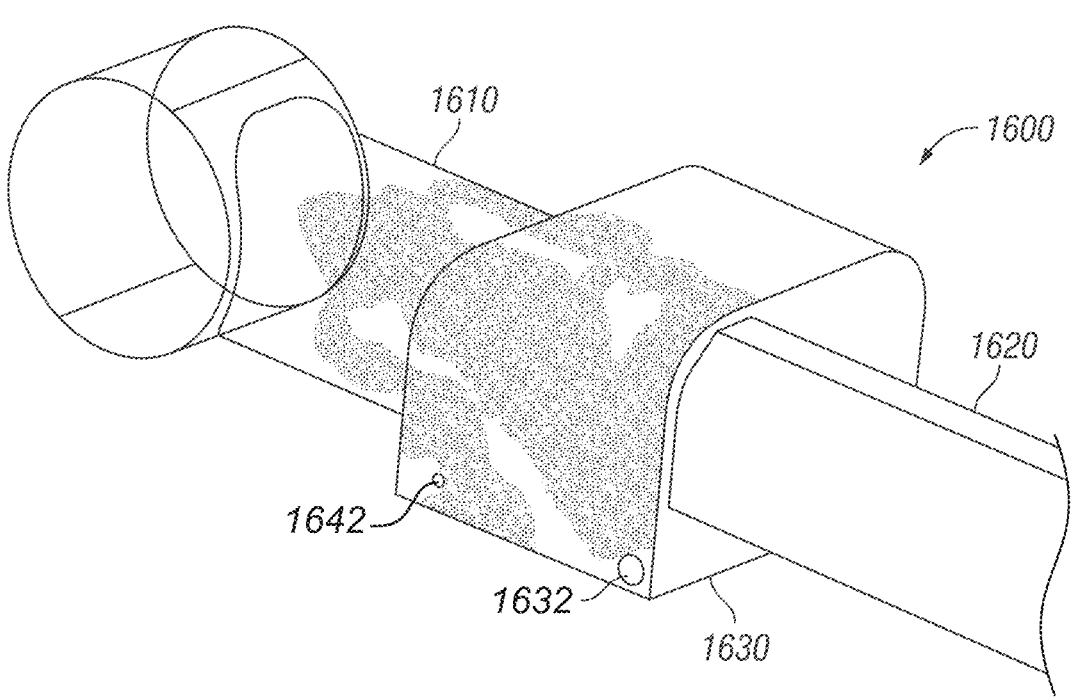

FIGS. 16A-16B is an internal and external view of a coupler 1600 including a motorized locking mechanism. A first portion 1610 may include a motor 1640 coupled to a ball bearing 1650 configured to apply a holding force against a release member 1630 of a second portion 1620. The motor 1640 applies a downward force within a predetermined range and serves as a vibration damper and locking mechanism to apply forces to both the first portion 1610 and second portion 1620 to securely lock them together and form a coupling between the first portion 1610 and the second portion 1620. The release member 1630 includes a bearing surface 1634 configured to contact the ball bearing 1650. The bearing surface 1634 includes a tapered or ramped surface to allow the bearing 1650 to recess into the release member 1630. The release member 1630 may rotate about a hinge 1632. A pin 1640 may secure the release member 1630. However, when the pin 1640 is released, the force of gravity and the downward pressure of the bearing 1650 will cause the release member 1630 to swing open so as to release the contact force between the first portion 1610 and second portion 1620, thereby decoupling the first portion 1610 and the second portion 1620.

FIGS. 17A-17D are schematic side views of a coupler 1700 including a translation mechanism. A first portion 1710 may include a carriage including a set of latches 1730 to secure a post 1722 of a second portion 1720. To couple the first portion 1710 and second portion 1720, the post 1722 is translated into the first portion 1710. To decouple the first portion 1710 and second portion 1720, the post is further translated into the first portion 1710 for a predetermined distance, and then may be retracted to decouple the first portion 1710 and second portion 1720.

Figure 17A:
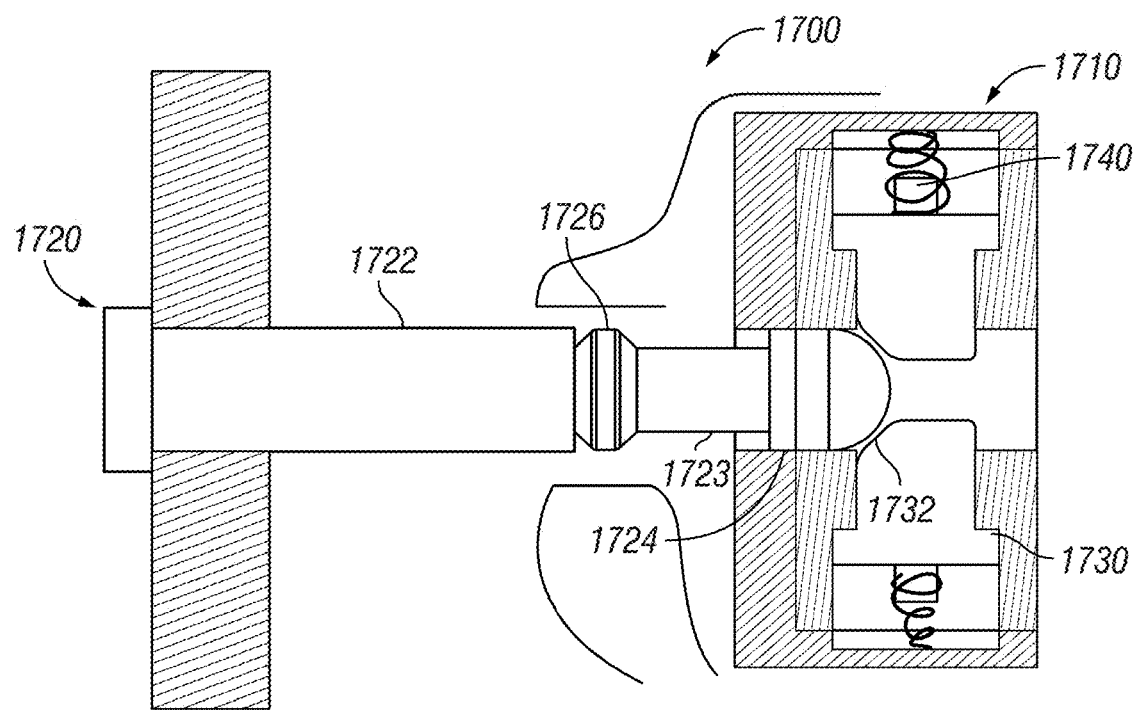
FIGS. 17A-17D are schematic side views of a coupler, according to an embodiment.
Figure 17B:
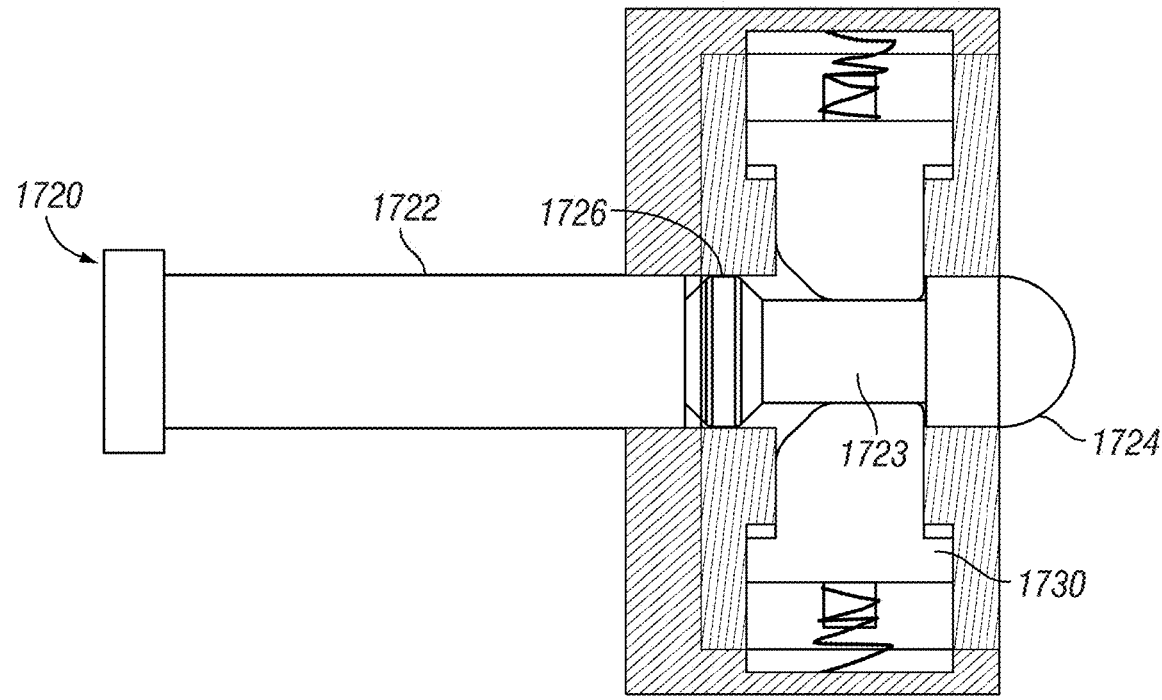

In FIGS. 17A-17B, a distal head 1724 is translated into the first portion 1710 to contact an angled first surface 1732 of the latches 1730. The latches may be coupled to springs 1740 biased to extend toward the other latch. The distal head 1724 slides through the latches such that the latches 1730 contact a second diameter portion 1723 of the post 1722. At this point, the post 1722 is prevented from retracting from the first portion 1710 by the contact between the latch 1730 and proximal end of the distal head 1724. The post 1722 includes a sliding collar 1726 that may slide along the second diameter portion 1723 of the post 1722.

Figure 17C:
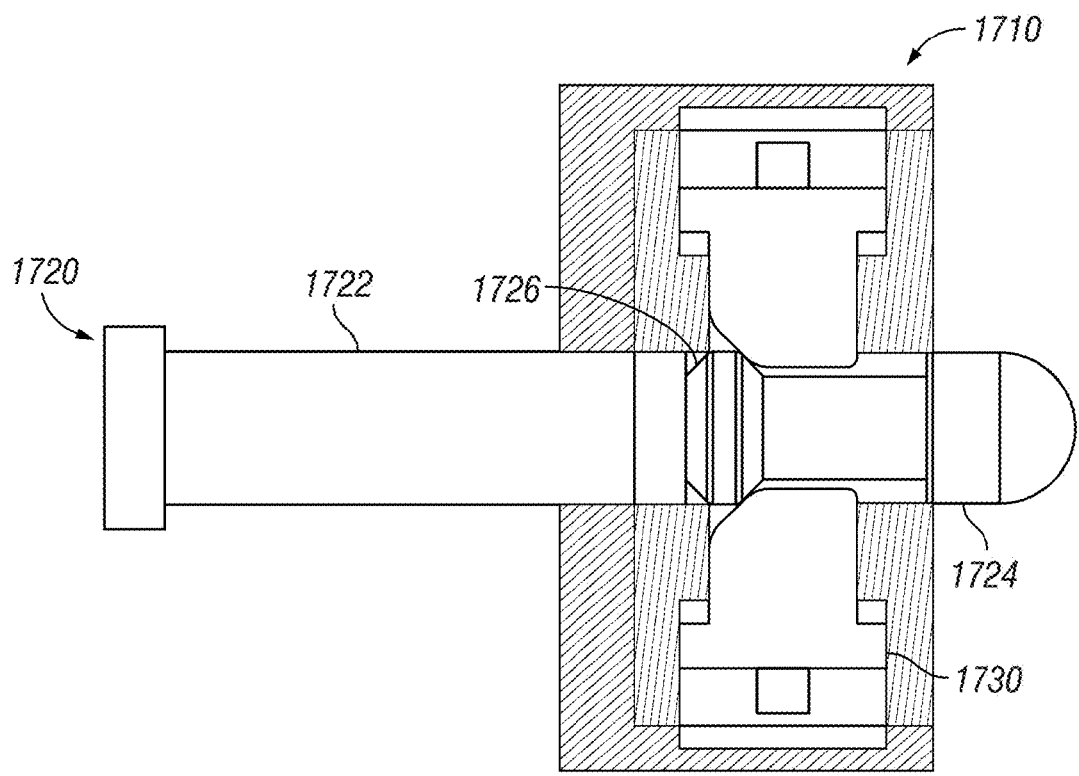
Figure 17D:
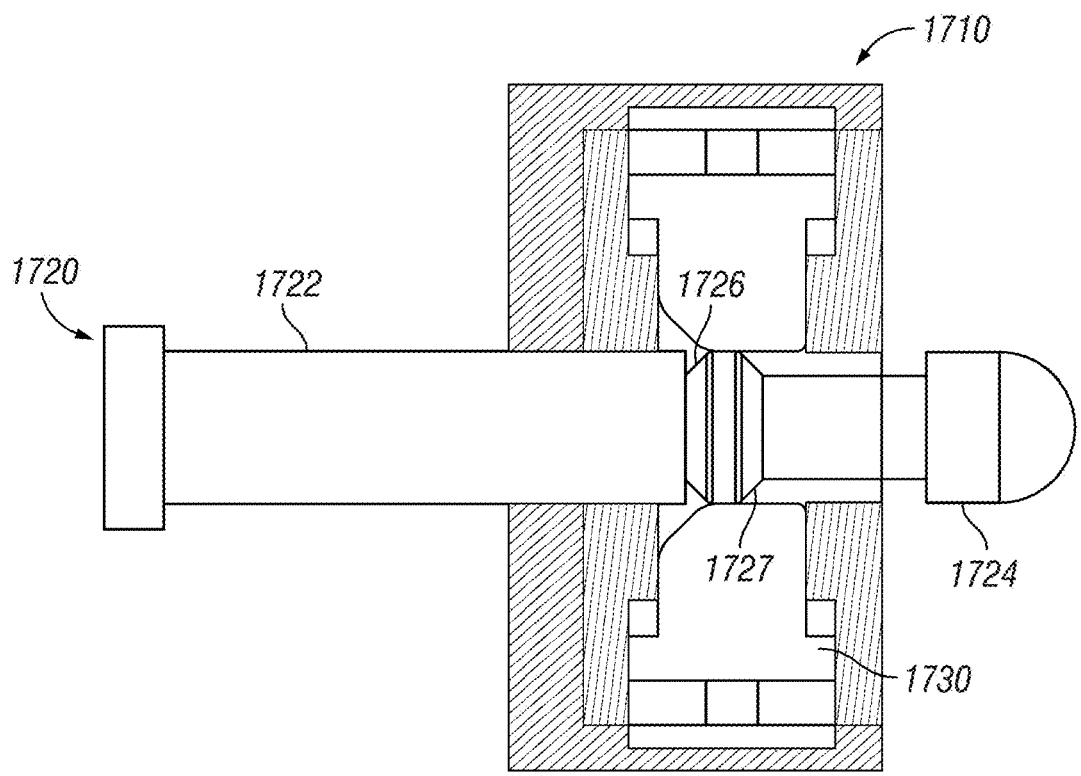

In FIG. 17C-17D, the post 1722 is further translated into the first portion 1710 such that the latch 1730 slides along the second diameter portion 1723. The first surface 1732 of the latch 1730 is configured to slide against the first surface 1927 of the sliding collar 1726 such that the latches 1730 hold the sliding collar 1726 in place. At this point, retraction of the post 1722 away from the first portion 1710 will translate the distal head 1724 in a reverse direction while the sliding collar remains fixed with respect to the latches 1730. In other words, the sliding collar 1726 will slide along the second diameter portion 1723 from a proximal end to a distal end. When the sliding collar 1726 contacts the distal head 1724, the opening of the latches 1730 is of a diameter such that distal head 1724 is not prevented from retracting away from the first portion 1710. In some embodiments, the distal head 1724 at a proximal end may include a recess to hold the sliding collar 1726.

Figure 18A:
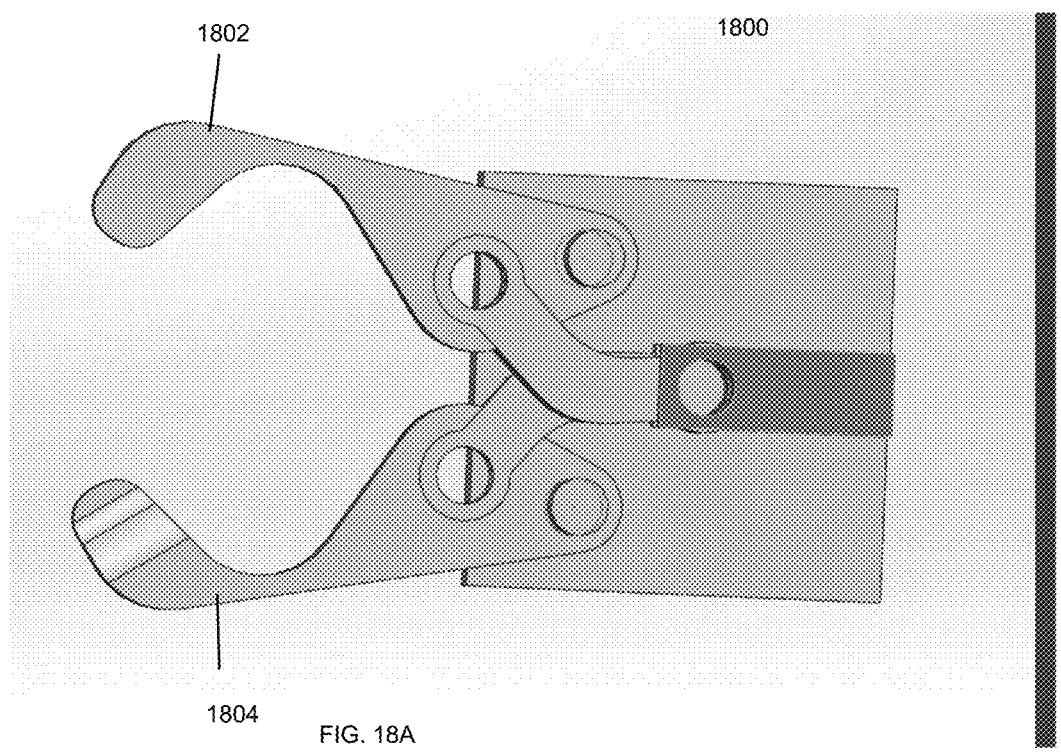
FIG. 18A-18B are side views of a grasper, according to an embodiment.
Figure 18B:
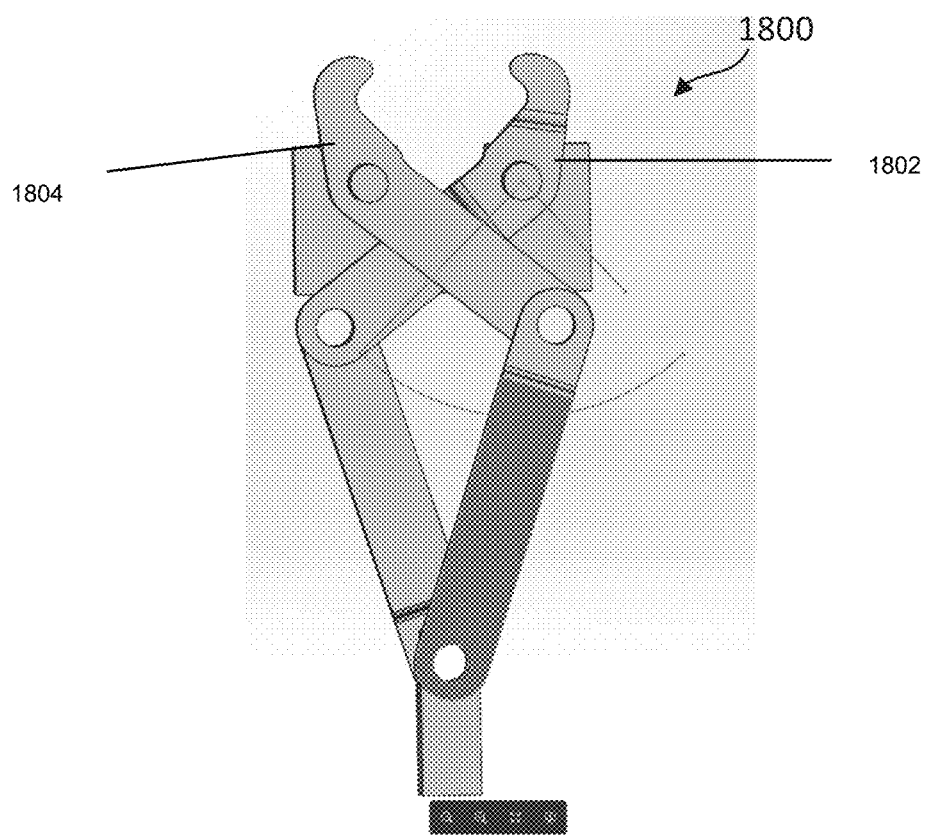

FIGS. 18A-18B are side views of a grasper 1800 configured to surround and grasp a post of a coupler of any of the previous embodiments. The grasper 1800 includes arms 1802, 1804 operable to apply a lateral force to a longitudinal axis of the post (e.g., post 422) of the coupler (e.g., coupler 400).

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. For several of the ideas presented herein, one or more of the parts may be optional. The invention should therefore not be limited by the above described embodiment, method, and examples, but by all embodiments and methods within the scope and spirit of the invention.

What is claimed is:

1. A coupler for coupling a robotic arm to a surgical table, the coupler comprising:
 a first portion configured to couple to a surgical table;
 a second portion configured to couple to a robotic arm, the second portion having a post configured to translate along a first axis of the first portion to couple the second portion to the first portion; and
 a locking mechanism configured to transition a coupling between the first portion and the second portion between a locked position and an unlocked position, wherein the locking mechanism is coupled to an interior cavity of the first portion and comprises a holder, a ball bearing assembly, a cam, and wherein the holder and the ball bearing assembly are configured to engage the post, and a translation of the cam along the first axis causes the holder to translate the post along the first axis between the locked position or the unlocked position, and in the locked position, movement of the first portion relative to the second portion in six degrees of freedom is constrained.

2. The coupler of claim 1, wherein the cam is a first cam, and the locking mechanism further comprises a second cam positioned within the interior cavity of the first portion, and wherein a translation of the first cam and the second cam along the first axis causes the holder to translate the post along the first axis to the locked position or the unlocked position.

3. The coupler of claim 2, wherein each of the first cam and the second cam are face cams having a variable cam surface profile configured to adjust a translation function or an axial force function of the locking mechanism.

4. The coupler of claim 1, wherein the holder comprises a receiving cavity dimensioned to receive the post, and wherein the interior cavity of the first portion comprises an interior contact surface and the post comprises an exterior contact surface, and a ball of the ball bearing assembly contacts the interior contact surface and the exterior contact surface in the locked position.

5. The coupler of claim 1, wherein the locking mechanism further comprises a biasing member configured to apply a biasing force to the ball bearing assembly.

6. The coupler of claim 1, wherein the first portion comprises an axially oriented groove along an outer surface, and the second portion comprises a kinematic mount configured to mate with the groove when the second portion is coupled to the first portion, and where the kinematic mount and the groove are dimensioned to constrain translation or rotation of the first portion with respect to the second portion.

7. The coupler of claim 1, wherein the first portion further comprises an alignment opening, and the second portion comprises an alignment protrusion, the alignment protrusion having an asymmetrical shape configured to mate with the alignment opening in a single orientation and prevent misalignment of the first portion with respect to the second portion.

8. The coupler of claim 1, wherein the post of the second portion is dimensioned to surround the first portion to constrain translation of the first portion with respect to the second portion along the first axis.

9. The coupler of claim 1, wherein the locking mechanism further comprises a shaft and the cam is coupled to a bushing, wherein the cam and the bushing are configured to translate along the shaft to vary a contact force of the ball bearing assembly against the post between the locked position and the unlocked position.

10. The coupler of claim 1, further comprising an electrical interface between the first portion and the second portion, wherein the electrical interface is operable to provide power to a motor for driving the locking mechanism.

11. A coupler for coupling a robotic arm to a surgical table, the coupler comprising:

a first portion having a first end configured to couple to a surgical table and a second end, the second end defining an opening to an interior cavity within the first portion;
a second portion configured to couple to a robotic arm, the second portion having a post configured to be received within the interior cavity and translate along the first axis of the first portion to couple the second portion to the first portion;
a locking mechanism having a holder that translates within the interior cavity along the first axis of the first portion to engage the post, a ball bearing assembly coupled to the holder, a first cam, and a second cam, and wherein a translation of the first cam and the second cam along the first axis causes the holder to translate the post along the first axis to the locked position or the unlocked position; and
a drive mechanism configured to drive an operation of the locking mechanism.

12. The coupler of claim 11, further comprising a connection sensor configured to detect a coupling and a decoupling between the first portion and the second portion.

13. The coupler of claim 11 wherein the ball bearing assembly comprises a set of ball bearings positioned within the interior cavity of the first portion.

14. The coupler of claim 11, wherein the holder comprises a receiving cavity dimensioned to receive the post, and positions the set of ball bearings around the post, and wherein a translation of the holder causes the set of ball bearings to contact an exterior contact surface of the post and an interior contact surface of the interior cavity in the locked position.

15. The coupler of claim 11, wherein each of the first cam and the second cam are face cams having a variable cam surface profile configured to adjust a translation function or an axial force function of the locking mechanism.

16. The coupler of claim 11, wherein the locking mechanism further comprises a biasing member configured to apply a biasing force to the ball bearing assembly.

17. The coupler of claim 11, wherein the first portion comprises an axially oriented groove along an outer surface, and the second portion comprises a kinematic mount configured to mate with the groove when the second portion is coupled to the first portion, and where the kinematic mount and the groove are dimensioned to constrain translation or rotation of the first portion with respect to the second portion.

18. The coupler of claim 11, wherein the first portion further comprises an alignment opening, and the second portion comprises an alignment protrusion, the alignment protrusion having an asymmetrical shape configured to mate with the alignment opening in a single orientation and prevent misalignment of the first portion with respect to the second portion.

19. The coupler of claim 11, wherein the drive mechanism comprises a handle.

20. The coupler of claim 11, wherein the drive mechanism comprises a motor.

* * * * *